United States Patent
Liu et al.

(10) Patent No.: US 11,903,963 B2
(45) Date of Patent: Feb. 20, 2024

(54) SHORT-ACTING HEPARIN-BASED ANTICOAGULANT COMPOUNDS AND METHODS

(71) Applicant: The University of North Carolina at Chapel Hill, Chapel Hill, NC (US)

(72) Inventors: Jian Liu, Chapel Hill, NC (US);
Zhangjie Wang, Changchun (CN);
Po-Hung Hsieh, Pasadena, CA (US);
Yongmei Xu, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/492,858

(22) PCT Filed: Mar. 12, 2018

(86) PCT No.: PCT/US2018/021986
§ 371 (c)(1),
(2) Date: Sep. 10, 2019

(87) PCT Pub. No.: WO2018/165656
PCT Pub. Date: Sep. 13, 2018

(65) Prior Publication Data
US 2021/0137967 A1    May 13, 2021

Related U.S. Application Data

(60) Provisional application No. 62/469,643, filed on Mar. 10, 2017.

(51) Int. Cl.
| | | |
|---|---|---|
| *A61K 31/727* | (2006.01) | |
| *A61K 38/48* | (2006.01) | |
| *C08B 37/00* | (2006.01) | |
| *C12P 19/04* | (2006.01) | |
| *C12P 19/18* | (2006.01) | |
| *A61P 7/02* | (2006.01) | |

(52) U.S. Cl.
CPC ........ *A61K 31/727* (2013.01); *A61K 38/4846* (2013.01); *A61P 7/02* (2018.01); *C08B 37/0075* (2013.01); *C12P 19/04* (2013.01); *C12P 19/18* (2013.01)

(58) Field of Classification Search
CPC .................................................. C08B 37/0075
See application file for complete search history.

(56) References Cited

U.S. PATENT DOCUMENTS

| | | |
|---|---|---|
| 4,554,101 A | 11/1985 | Hopp |
| 4,865,870 A | 9/1989 | Hu et al. |
| 5,527,785 A | 6/1996 | Bevilacqua |
| 5,543,403 A | 8/1996 | Petitou et al. |
| 5,817,487 A | 10/1998 | Kobayashi et al. |
| 5,834,282 A | 11/1998 | Habuchi et al. |
| 5,935,824 A | 8/1999 | Sgarlato |
| 6,255,088 B1 | 7/2001 | Wong et al. |
| 6,861,254 B1 | 3/2005 | Rosenberg et al. |
| 7,101,859 B2 | 9/2006 | Yedgar et al. |
| 7,531,338 B2 | 5/2009 | Liu |
| 9,951,149 B2 | 4/2018 | Liu et al. |
| 10,286,047 B2 | 5/2019 | Spirig et al. |
| 11,203,772 B2 | 12/2021 | Xu et al. |
| 11,633,424 B2 | 4/2023 | Liu et al. |
| 2003/0083294 A1 | 5/2003 | Sullenger |
| 2003/0099967 A1 | 5/2003 | Deangelis |
| 2004/0191870 A1 | 9/2004 | Rosenberg et al. |
| 2004/0259142 A1 | 12/2004 | Chai et al. |
| 2005/0090601 A1 | 4/2005 | Dadalas et al. |
| 2005/0090661 A1 | 4/2005 | Asari et al. |
| 2005/0101532 A1 | 5/2005 | Yang et al. |
| 2005/0191288 A1 | 9/2005 | Bennett et al. |
| 2005/0255562 A1 | 11/2005 | Rosenberg et al. |
| 2005/0282775 A1 | 12/2005 | Kennedy |
| 2006/0165673 A1 | 7/2006 | Liu |
| 2006/0172931 A1 | 8/2006 | San Antonio et al. |
| 2006/0229276 A1 | 10/2006 | Hook et al. |
| 2008/0109236 A1 | 5/2008 | DeAngelis |
| 2009/0035787 A1 | 2/2009 | Liu |
| 2009/0155851 A1 | 6/2009 | Sugiura et al. |
| 2009/0197308 A1 | 8/2009 | Liu |
| 2010/0125052 A1 | 5/2010 | Lu et al. |
| 2010/0298260 A1 | 11/2010 | Sundaram et al. |
| 2010/0305022 A1 | 12/2010 | Shriver |

(Continued)

FOREIGN PATENT DOCUMENTS

| | | |
|---|---|---|
| EP | 0 394 971 | 10/1990 |
| EP | 0 565 863 | 10/1993 |

(Continued)

OTHER PUBLICATIONS

Copeland et al. Using a 3-O-Sulfated Heparin Octasaccharide To Inhibit the Entry of Herpes Simplex Virus Type 1. Biochemistry. 2008;47:5774-5783.*

Chen, Miao, Dissertation: Towards De Novo Synthesis of Structure-Defined Oligosaccharides with Heparan Sulfate Biosynthetic Enzymes, 2008, 167 pages (Year: 2008).*

Office Action corresponding to Chinese Patent Application No. 201880020095.X dated Jun. 8, 2022.

Advisory Action corresponding to U.S. Appl. No. 13/996,930 dated Dec. 9, 2016.

Aikawa et al., "Molecular Cloning and Expression of a Third Member of the Heparan Sulfate/Heparin GlcNAc N-Deacetylase/ N-Sulfotransferase Family," The Journal of Biological Chemistry, vol. 274, No. 5, pp. 2690-2695 (Jan. 29, 1999).

(Continued)

*Primary Examiner* — Bahar Craigo
(74) *Attorney, Agent, or Firm* — Jenkins, Taylor, & Hunt P.A.

(57) ABSTRACT

Heparin compounds and synthetic heparin analogues having short acting anticoagulant activity are provided. Methods of synthesizing such heparin compounds, including chemoenzymatic pathways using sulfotransferase enzymes are provided. Methods of treating subjects in need of anticoagulant activity are provided.

44 Claims, 14 Drawing Sheets

(56) References Cited

U.S. PATENT DOCUMENTS

| | | | |
|---|---|---|---|
| 2011/0054236 | A1 | 3/2011 | Yang et al. |
| 2011/0281819 | A1 | 11/2011 | Kakehi et al. |
| 2012/0064044 | A1 | 3/2012 | Egan |
| 2012/0308546 | A1 | 12/2012 | Kizhakkedathu et al. |
| 2012/0322114 | A1 | 12/2012 | Liu et al. |
| 2012/0322760 | A1 | 12/2012 | Fier et al. |
| 2013/0022647 | A1 | 1/2013 | Kizhakkedathu et al. |
| 2013/0296540 | A1 | 11/2013 | Xu et al. |
| 2013/0338097 | A1 | 12/2013 | Stephens et al. |
| 2016/0122446 | A1* | 5/2016 | Liu ............... C08B 37/0075 514/56 |
| 2021/0169923 | A1 | 6/2021 | Arnold et al. |
| 2021/0260098 | A1 | 8/2021 | Liu et al. |
| 2021/0332076 | A1 | 10/2021 | Liu et al. |
| 2022/0265699 | A1 | 8/2022 | Arnold et al. |
| 2022/0416486 | A1 | 12/2022 | Yamaguchi |

FOREIGN PATENT DOCUMENTS

| | | |
|---|---|---|
| JP | 6670235 | 3/2020 |
| WO | WO 89/04328 | 5/1989 |
| WO | WO93/05167 | 3/1993 |
| WO | WO 96/14425 | 5/1996 |
| WO | WO2003018598 | 3/2003 |
| WO | WO 2004/005475 A2 | 1/2004 |
| WO | WO 2004/009642 | 1/2004 |
| WO | WO 2004/017910 A2 | 3/2004 |
| WO | WO2005/118609 | 12/2005 |
| WO | WO 2006/124801 | 11/2006 |
| WO | WO 2009/079693 A1 | 7/2009 |
| WO | WO 2012/088416 A2 | 6/2012 |
| WO | WO 2012/116048 | 8/2012 |
| WO | WO 2014/204929 | 12/2014 |
| WO | WO 2019/010216 A1 | 1/2019 |
| WO | WO 2019/090203 A1 | 5/2019 |
| WO | WO 2019/246264 | 12/2019 |
| WO | WO 2021/097345 A1 | 5/2021 |
| ZA | 2014800444299 | 5/2021 |

OTHER PUBLICATIONS

Aikawa et al., "Multiple Isozymes of Heparan Sulfate/Heparin GlcNAc N-Deacetylase/GlcN N-Sulfotransferase," The Journal of Biological Chemistry, vol. 276, No. 8, pp. 5876-5882 (Feb. 23, 2001).

Alexander et al., "Syndecan-1 is required for Wnt-1-induced mammary tumorigenesis in mice," Nat. Genet., vol. 25, pp. 329-332 (2000).

Altschul et al., "Basic Local Alignment Search Tool," J. Mol Bio., vol. 1215, pp. 403-410 (1990).

Antoine et al., "Mechanistic biomarkers provide early and sensitive detection of acetaminophen-induced acute liver injury at first presentation to hospital." Hepatology vol. 58, pp. 777-787 (2013).

Applicant-Initiated Interview Summary corresponding to U.S. Appl. No. 13/996,930 dated Jan. 23, 2017.

Arnold et al., "Design of anti-inflammatory heparan sulfate to protect against acetaminophen-induced acute liver failure." Sci. Transl. Med., vol. 12, Article ID eaav8075 (2020).

Arnold et al., "Synthetic anticoagulant heparan sulfate attenuates liver ischemia reperfusion injury." Sci. Reports, vol. 10, Article No. 17187 (10 pages) (2020).

Arungundram, S.; Al-Mafraji, K.; Asong, J.; Leach III, F. E.; Amster, I. J.; Venot, A.; Je, T.; Boons, G. J. "Modular Synthesis of Heparan Sulfate Oligosaccharides for Structure-Activity Relationship Studies," J. Am. Chem. Soc. 2009, 131, 17394.

Atha et al., "Contribution of Monosaccharide Residues in Heparin Binding to Antithrombin III," Biochemistry, vol. 24, pp. 6723-6729 (1985).

Avci et al., "Synthetic oligosaccharides as heparin-mimetics displaying anticoagulant properties," Curr. Pharm. Des., vol. 9, pp. 2323-2335 (2003).

Axelsson et al., "Inactivation of heparan sulfate 2-O-sulfotransferase accentuates neutrolphil infiltration during acute inflammation in mice." Blood, vol. 120, pp. 1742-1751 (2012).

Bailey et al., "Delays during the administration of acetylcysteine for the treatment of paraacetamol overdose." Br. J. Clin. Pharmacol. vol. 62, pp. 1358-1363 (2016).

Balagurunathan et al., Chemoenzymatic Synthesis of Classical and Non-classical Anticoagulant Heparan Sulfate Polysaccharide, J. Biol. Chem., vol. 278, pp. 52613-52621 (2003).

Balagurunathan et al., Enzymatic synthesis of antithrombin III-binding heparan sulfate pentasaccharide, Nat. Biotechnol., vol. 21, pp. 1343-1346 (2003).

Baleux et al. (2009) Nat. Chem. Biol., 5, 743-748.

Bernfield et al., "Heparin-Binding Proteins," Annu. Rev. Biochem., vol. 68, pp. 729-777 (1999).

Bianchi et al., "High-mobility group box 1 protein orchestrates responses to tissue damage via inflammation, innate and adaptive immunity, and tissue repair." Immunol. Rev. vol. 280, pp. 74-82 (2017).

Bitter et al. (1962) Anal. Biochem. 4, 330-334.

Bjornsson, Simultaneous Preparation and Quantitation of Proteoglycans by Preciptation with Alcian Blue, Anal. Biochem., vol. 210, pp. 282-291 (1993).

Blieden et al., "A perspective on the epidemiology of acetaminophen exposure and toxicity in the United States." Expert Rev. Clin. Pharmacol. vol. 7, pp. 341-348 (2014).

Bowman et al., Carbohydrate sulfotransferases: medliators of extracellular Communication, Chemistry & Biology, vol. 6, pp. R9-R22 (Jan. 1999).

Broun et al., "Catalytic plasticity of fatty acid modification enzymes underlying chemical diversity of plant lipids," Science, vol. 282, pp. 1315-1317 (1998).

Brown et al., Drug Research, "Cardenolide analogues. 11. Improved method for the use of Fetizon's reagent in the synthesis of cardiac glycosides", vol. 31, No. 7, pp. 1059-1064 (1981).

Burkart et al., "Regeneration of PAPS for the Enzymatic Synthesis of Sulfated Oligosaccharides," J. Org. Chem., vol. 65, pp. 5565-5574 (2000).

Cai et al., "Towards the chemoenzymatic synthesis of heparan sulfate oligosaccharides: Oxidative cleavage of p-nitrophenyl group with ceric ammonium salts," Tetra. Lett., vol. 54, No. 33, pp. 4471-1474 (2013).

Capila et al., "Heparin—Protein Interactions," Angew. Chem. Int. Ed., vol. 41, pp. 390-412 (2002).

Carfi et al., "Herpes Simplex Virus Glycoprotein D Bound to the Human Receptor HveA," Molecular Cell, vol. 8, pp. 169-179 (Jul. 2001).

Cassinelli et al., "Old and new applications of non-anticoagulant heparin." International Journal of Cardiology, 212S1 pp. S14-S21 (2016).

Casu et al., Heparin-like compounds prepared by chemical modification of capsular polysaccharide from E. coli K5, Carbohydrate Research vol. 263, pp. 271-28 (1994).

Chen et al., "Enzymatic redesigning of biologically active haparan sulfate," JBC, vol. 280, No. 52, pp. 42817-42825 (2005).

Chen et al., "Using an Enzymatic Combinatorial Approach to Identify Anticoagulant Heparan Sulfate Structures," Chemistry and Biology, Current Biology, London, GB, vol. 14., No. 9, pp. 986-993 (Sep. 19, 2007).

Chen et al., "Biosynthesis of 3-O-sulfated heparan sulfate: unique substrate specificity of heparan sulfate 3-O-sulfotransferase isoform 5," Glycobiology, vol. 13, No. 11, pp. 785-794 (Nov. 2003).

Chen et al., "Sterile inflammation: sensing and reacting to damage." Nat. Immunol. vol. 10, pp. 826-837 (2010).

Chen et al., "Tyrosine-Ester Sulfotransferase from Rat Liver: Bacterial Expression and Identificationn," Protein Expression Purif., vol. 3, pp. 421-426 (1992).

Chen, M., et al. (2006) Biochemistry, 45, 12358-12365.

Communication of European publication number and information on the application of Article 67(3) EPC corresponding to European Application No. 14812890.3 dated Mar. 31, 2016.

Communication of the extended European search report corresponding to European Application No. 14812890.3 dated Dec. 21, 2016.

(56) References Cited

OTHER PUBLICATIONS

Conrad, Heparin-Binding Proteins, J. of Medicinal Chemistry, vol. 42, No. 4, pp. 777-778 (1998).
Crowther et al., "Mechanisms responsible for the failure of protamine to inactivate low-molecular-weight heparin," British Journal of Hematology, vol. 116, pp. 178-186 (2002).
Darden, T.; York, D.; Pedersen, L. C. J. Chem. Phys. 1993, 98, 10089.
Das et al., "Synthesis of Conformationally Locked l-Id2uronic Acid Derivatives: Direct Evidence for a Critical Role of the Skew-Boat 2S0 Conformer in the Activation of Antithrombin by Heparin," Chem. Eur. J., vol. 7, No. 22, pp. 4821-4834 (2001).
Davenport, "Review article: Low-molecular-weight heparin as an alternative anticoagulant to unfractionated heparin for routine outpatient haemodialysis treatments," Nephrology, vol. 14, pp. 456-461 (2009).
DeAgostini, A. I.; Dong, J.-C.; de Vantery Arrighi, C.; Ramus, M.-A.; Dentand-Quadri, I.; Thanlmann, S.; Ventura, P.; Ibecheole, V.; Monge, F.; Fischer, A.-M.; HajMohammadi, S.; Shworak, N.; Zhang, L.; Zhang, Z.; Linhardt , R. J. "Human Follicular Fluid Heparan Sulfate Contains Abundant 3-O-Sulfated Chains with Anticoagulant Activity," J. Biol. Chem. 2008, 283, 28115.
Decision to Grant corresponding to Japanese Patent Application No. 2016521505 dated Feb. 3, 2020.
Dementiev et al., "The ternary complex of antithrombin-anhydrothrombin-heparin reveals the basis of inhibitor specificity," Nat. Struct. Biol., vol. 11, pp. 867-863 (2004).
Dooley, T., "Cloning of the human phenol sulfotransferase gene family: three genes implicated in the metabolism of catecholamines, thyroid hormones and drugs," Chemico-Biological Interactions, vol. 109, pp. 29-41 (1998).
Dou et al., "Role of Deacetylase Activity of N-Deacetylase/N-Sulfotransferase 1 in Forming N-Sulfated Domain in Heparan Sulfate", The Journal of Biological Chemistry, vol. 290, No. 33, pp. 20427-20437 (Aug. 14, 2015).
Duncan et al., Biochim. Biophys. Acta, vol. 1671, pp. 34-43 (2004).
Edavettal et al.,, "Crystal Structure and Mutational Analysis of Heparan Sulfate 3-O-Sulfotransferase Isoform 1," J. Biol. Chem., vol. 279, No. 24, pp. 25789-25797 (Jun. 11, 2004).
Edens et al., "Gradient Polyacrylamide Gel Electrophoresis for Determination of Molecular Weights of Heparin Preparations and Low-Molecular-Weight Heparin Derivatives," J. Pharm. Sci., vol. 81, No. 8, pp. 823-827 (Aug. 1992).
Esko et al., "Molecular diversity of heparan sulfate," J. Clin. Invest., vol. 108, pp. 169-173 (2001).
Esko et al., "Order Out of Chaos: Assembly of Ligand Binding Sites in Heparan Sulfate," Annu. Rev. Biochem., vol. 71, pp. 435-471 (2002).
European Search Report corresponding to European Patent Application No. 18764628.6 dated Dec. 2, 2020.
European Search Report corresponding to European Patent Application No. 18873131.9 dated Jul. 12, 2021.
Falany, C., "Introduction: Changing view of sulfation and the cytosolic Sulfotransferases," vol. 11, The FASEB Journal, pp. 1-2 (Jan. 1997).
Feltracco et al., "Perioperative thrombotic complications in liver transplantation." World J. Gastroenterol., vol. 21, pp. 8004-8013 (2015).
Feng et al., "Characteristics Associated with Liver Graft Failure: The Concept of a Donor Risk Index." Am. J. Transplant., vol. 6, pp. 783-790 (2006).
Feyerabend et al., "Heparan sulfate C5-epimerase is essential for heparin biosynthesis in mast cells," Nat. Chem. Biol., vol. 2, No. 4, pp. 195-196 (Apr. 2006).
Fiser, A; Sali, A Methods Enzymol 2003, 374, 461.
Fukuta et al., "Molecular cloning and expression of human chondroitin 6-sulfotransferase," Biochimica et Biophysica Acta, vol. 1399, pp. 57-61 (1998).
Fuster et al., The sweet and sour of cancer: glycans as novel therapeutic targets, Nat. Rev. Cancer, vol. 5, No. 7, pp. 1-27 (Jul. 2005).
Gallagher, "Heparan sulfate: growth control with a restricted sequence menu," J. Clin. Invest., vol. 108, pp. 357-361 (2001).
Gama et al., "Sulfation patterns of glycosaminoglycans encode molecular recognition and activity," Nat. Chem. Biol., vol. 2, No. 9, pp. 467-473 (Sep. 2006).
Gama et al., "Sulfation patterns of glycosaminoglycans encode molecular recognition and activity." Nat. Chem. Biol., vol. 2, pp. 467-473 (2006).
Ganey et al. "Role of the Coagulation System in Acetaminophen-Induced Hepatotoxicity in Mice." Hepatology, vol. 46(4), pp. 1177-1186 (2007).
Genbank Accession No. AAC40135 dated Jun. 17, 1998.
Genbank Accession No. BAA89247 dated Jan. 29, 2000.
Genbank Accession No. NP_005105 dated May 24, 2014.
Genbank Accession No. NP_006032 dated Feb. 26, 2014.
Genbank Accession No. NP_006033 dated Jan. 26, 2014.
Genbank Accession No. NP_056633 dated May 3, 2014.
Genbank Accession No. NP_056635 dated Mar. 3, 2014.
Gribskov,M., Burgess,R.R. and Devereux,J. (1986) Nucl. Acids Res. 14, 327-334.
Guerrini et al., "Oversulfated chondroitin sulfate is a contaminant in heparin associated with adverse clinical events," Nat. Biotechnol., vol. 26, No. 6, pp. 669-675 (Jun. 2008).
Guerrini, M.; Elli, S.; Mourier, P.; Rudd, T. R.; Gaudesi, D.; Casu, B.; Boudier, C.; Torri, G.; Viskov, C. "An unusual antithrombin-binding heparin octasaccharide with an additional 3-O-sulfated glucosamine in the active pentasaccharide sequence," Biochem. J. 2013, 449, 343.
Guerrini, M.; Mourier, P. A.; Torri, G.; Viskov, C. "Antithrombin-binding oligosaccharides: structural diversities in a unique function?," Glycoconj. J. 2014, 31, 409.
Guimond et al.,"Fibroblast growth factor receptor signaling is dictated by specific heparin sulphate saccharides," Curro. Biol., vol. 9, No. 22 pp. 1343-1346 (1999).
Guo et al., "Changes in substrate specificity of the recombinant form of phenol sulfotransferase IV (tyrosine-ester sulfotransferase)," Chem.-Biol. Interact., vol. 92, pp. 25-31 (1994).
Habuchi et al., The Occurrence of Three Isoforms of Heparan Sulfate 6-O-Sulfotransferase Having Different Specificities for Hexuronic Acid Adjacent to the Targeted N-Sulfoglucosamine, J. Biol. Chem., vol. 275, No. 4, pp. 2859-2868 (Jan. 28, 2000).
Habuchi et al., "Molecular Characterization and Expression of Heparan-sulfate 6-Sulfotransferase—Complete cDNA Cloning in Human and Partial Cloning in Chinese Hamster Ovary Cells," The Journal of Biological Chemistry, vol. 273, No. 15, pp. 9208-9213 (Apr. 10, 1998).
HajMohammadi, S.; Enjyoji, K.; Princivalle, M.; Christi, P.; Lech, M.; Beeler, D. L.; Rayburn, H.; Schwartz, J. J.; Barzegar, S.; de Agostini, A. I.; Post, M. J.; Rosenberg, R. D.; Shworak, N. W. J. Clin. Invest. 2003, 111, 989.
Hansen, S. U.; Miller, G. J.; Cole, C.; Rushton, G.; Avizienyte, E.; Jayson, G. C.; Gardiner, J. M. Nat Commun 2013, 4:2016, doi:10. 1038/ncomms3016.
Harada et al., "Dalteparin, a low molecular weight heparin, attenuates inflammatory responses and reduces ischemia-reperfusion-induced liver injury in rats." Crit. Care Med., vol. 34, Article No. 8, (2006).
Harris et al., Endocytic Function, Glycosaminoglycan Specificity, and Antibody Sensitivity of the Recombinant Human 190-kDa Hyaluronan Receptor for Endocytosis (HARE), J. Biol. Chem., vol. 279, No. 35, pp. 36201-36209 (Aug. 27, 2004).
Heard, "Acetylcystein for acetaminophen poisoning." N. Eng. J. Med. Vol. 359, pp. 285-292 (2008).
Hernaiz et al., "Enzymatic Modification of Heparan Sulfate on a Biochip Promotes Its Interaction with Antithrombin III," Biochem. Biophys. Res. Commun., vol. 276, pp. 292-297 (2000).
Hirsch et al., Heparin and Low-Molecular-Weight Heparin The Seventh ACCP Conference on Antithrombotic and Thrombolytic Therapy, CHEST, vol. 126, pp. 188S-203S (2004).

(56) References Cited

OTHER PUBLICATIONS

Hirsh et al., "Beyond Unfractionated Heparin and Warfarin Current and Future Advances," Circulation, vol. 116, pp. 552-560 (2007).
Holmborn et al., "Heparan Sulfate Synthesized by Mouse Embryonic Stem Cells Deficient in NDST1 and NDST2 Is 6-O-Sulfated but Contains No N-Sulfate Groups," J. Biol. Chem., vol. 279, No. 41, pp. 42355-42358 (2004).
Hsieh et al., "Chemoenzymatic synthesis and structural characterization of 2-O-sulfated glucuronic acid containing heparan sulfate hexasaccharides." Glycobiology vol. 24, pp. 681-692 (2014).
Hsieh, P.-H.; Thieker, D. F.; Guerrini, M.; Woods, R. J.; Liu, J. Sci Rep 2016, 6, 29602; doi: 10.1038/srep29602.
Hu, Y.-P.; Lin, S.-Y.; Huang, C.-Y.; Zulueta, M. M. L.; Liu, J.-Y.; Chang, W.; Hung, S.-C. Nat Chem 2011, 3, 557.
Huang, C. C.; Meng, E. C.; Morris, J. H.; Pettersen, E. F.; Ferrin, T. E. Nucleic Acids Res. 2014, 42, w478.
Huebener el al., "The HMGB1/RAGE axis triggers neutrophil-mediated injury amplification following necrosis." J. Clin. Invest. vol. 125, pp. 539-550 (2015).
Humphrey, W.; Dalke, A; Schulten, K. J. Mol. Graph. 1996, 14, 33.
Iba et al., "Advance in the management of sepsis-induced coagulopathy and disseminated intravascular coagulation." J. Clin. Med., vol. 8, Article No. 728 (16 pages) (2019).
Ibrahimi et al., "Kinetic Model for FGF, FGFR, and Proteoglycan Signal Transduction Complex Assembly," Biochemistr, vol. 43, pp. 4724-4730 (2004).
Intention to Grant corresponding to European Patent Application No. 11849994.6 dated Apr. 7, 2021.
Intention to Grant corresponding to European Patent Application No. 11849994.6 dated Sep. 1, 2021.
Intention to Grant corresponding to European Patent Application No. 14812890.3 dated Oct. 27, 2021.
International Preliminary Report on Patentability Corresponding to International application No. PCT/US 2018/021986 dated Sep. 10, 2019.
International Preliminary Report on Patentability corresponding to International application No. PCT/US 2018/059152 dated May 14, 2020.
International Preliminary Report on Patentability corresponding to International Application No. PCT/US2011/066843 dated Jul. 4, 2013.
International Preliminary Report on Patentability corresponding to International Application No. PCT/US2014/042683 dated Dec. 30, 2015.
International Preliminary Report on Patentability Corresponding to International Patent Application No. PCT/US 2020/060581 dated May 27, 2022.
International Search Report and the Written Opinion of the International Searching Authority corresponding to International application No. PCT/US 2018/059152 dated Mar. 6, 2019.
International Search Report and Written Opinion of the International Searching Authority Corresponding to International Patent Application No. PCT/US 2020/060581 dated Feb. 11, 2021.
International Search Report corresponding to International Application No. PCT/US2014/042683 dated Oct. 9, 2014.
International Search Report Corresponding to International application No. PCT/US 2018/021986 dated Aug. 1, 2018.
Jackson et al., "Thromboinflammation: challenges of therapeutically targeting coagulation and other host defense mechanisms." Blood, vol. 133, pp. 906-918 (2019).
Jaeschke et al., "Complement activates Kupffer cells and neutrophils during reperfusion after hepatic ischemia." Am. J. Physiol-Gastroint. Liver Physiol., vol. 264, pp. G801-G809 (1993).
Jaimes et al., "Unfractioned heparin for treatment of sepsis: A randomized clinical trial (The HETRASE Study)." Crit. Care Med., vol. 37, pp. 1185-1196 (2009).
Jemth et al., "Oligosaccharide library-based assessment of heparan sulfate 6-0-sulfotransferase substrate specificity," Journal of Biological Chemistry, vol. 278, No. 27, pp. 24371-24376 (Jul. 4, 2003).

Jin, L.; Abrahams, P.; Skinner, R.; Petitou, M.; Pike, R. N.; Carrell, R. W. Proc. Natl. Acad. Sci. 1997, 94, 14683.
Kakkar et al., "Low Molecular Weight Heparin, Therapy With Dalteparin, and Survival in Advanced Cancer: The Fragmin Advanced Malignancy Outcome Study (FAMOUS)," J. Clin. Oncol., vol. 22, No. 10, pp. 1944-1948 (May 15, 2004).
Kakuta et al., "Heparan sulphate N-sulphotransferase activity: reaction mechanism and substrate recognition," Biochem. Soc. Trans., vol. 31 (pt2), pp. 331-334 (2003).
Kamimura, K.; Rhodes, J. M.; Ueda, R.; McNeely, M.; Shukla, D.; Kimata, K.; Spear, P. G.; Shworak, N. W.; Nakata, H. J. Cell Biol. 2004, 166, 1069.
Kaneko et al., "Coagulation and fibrinolytic profiles and appropriate use of heparin after living-donor liver transplantation." Clin. Transplant., vol. 19, pp. 804-809 (2005).
Kirschner, K. N.; Yongye, A B.; Tschampel, S. M.; Gonzalez-Outeirino, J.; Daniels, C. R.; Foley, B. L.; Woods, R. J. J. Comput. Chem. 2008, 29, 622.
Kisselev, L., "Polypeptide release factors in prokaryotes and eukaryotes: same function, different structure," Structure, vol. 10, pp. 8-9 (2002).
Kollman, P. A; Massova, I.; Reyes, C.; Kuhn, B.; Hua, S.; Chong, L.; Lee, M.; Lee, T.; Duan, Y.; Wang, W.; Donini, O.; Cieplak, P.; Srinivasan, J.; Case, D. A; Cheatham, T. E. r. Acc. Chem. Res. 2000, 33, 889.
Konishi et al., "Hepatic ischemia/reperfusion: mechanisms of tissue injury, repair, and regeneration." Gene Expr., vol. 17, pp. 277-287 (2017).
Kopec et al., "Fibrin(ogen) drives repair after acetaminophen-induced liver injury via leukocyte aMb2 integrin-dependent upregulation of Mmp12." J. Hepatol. vol. 66, pp. 787-797 (2017).
Kreimann, M.; Brandt, S.; Krauel, K.; Block, S.; Helm, C.; Weitschies, W.; Greinacher, A.; Delcea, M. Blood 2014, in press.
Kreuger et al., Interactions between heparan sulfate and proteins: the concept of specificity, J. Cell Biol., vol. 174, No. 3, pp. 323-327 (Jul. 31, 2006).
Krummenacher et al., "The First Immunoglobulin-Like Domain of HveC Is Sufficient To Bind Herpes Simplex Virus gD with Full Affinity, While the Third Domain Is Involved in Oligomerization of HveC," J. Virol., vol. 73, pp. 8127-8137 (Oct. 1999).
Kuberan et al., "Enzymatic synthesis of antithrombin III-binding heparan sulfate pentasaccharide," Nature Biotechnology, vol. 21, No. 11, 1343-1346 (Nov. 2003).
Kuberan et al., "Rapid Two-Step Synthesis of Mitrin from Heparosan: A Replacement for Heparin," J. Am. Chem. Soc., vol. 125, pp. 12424-12425 (2003).
Kuberan. et al., The Journal of Biological Chemistry, "Chemoenzymatic Synthesis of Classic and Non-classical Anticoagulant Heparan Sulfate Polysaccharides", 2003, vol. 278, No. 52, pp. 52613-52621 (Year: 2003).
Kubes et al., "Sterile inflammation in the liver." Gastroenterology, vol. 143, pp. 1158-1172 (2012).
Kyte & Doolittle (1982) A Simple Method for Displaying the Hydropathic Character of a Protein. J. Mol Biol,157: 105-132.
Langdown, J.; Belzar, K. J.; Savory, W. J.; Baglin, T. P.; Huntington, J. A. J. Mo/. Biol. 2009, 386, 1278.
Laurent et al., "The Molecular-Weight-Dependence of the Anti-Coagulant Activity of Heparin," Biochem. J., vol. 175, pp. 691-701 (1978).
Ledin et al., "Heparan Sulfate Structure in Mice with Genetically Modified Heparan Sulfate Production," J. Biol. Chem., vol. 279, No. 41, pp. 42732-42741 (2004).
Lee, M.K., and Lander, A.D., (1991) Proc. Natl. Acad. Sci. USA 88, 2768-2772.
Lee, "Acetaminophen toxicity: changing perceptions on a social/medical issue." Hepatology, vol. 46, pp. 966-970 (2007).
Li et al., "Biosynthesis of Heparin/Heparan Sulfate cDNA Cloning and Expression of D-Glucuronyl C5-Epimerase From Bovine Lung," J. Biol. Chem., vol. 272, No. 4, pp. 28158-28163 (Oct. 31, 1997).
Liliensiek et al., "Receptor for advanced glycation end products (RAGE) regulates sepsis but not the adaptive immune response." J. Clin. Invest. vol. 113, pp. 1641-1650 (2004).

(56) References Cited

OTHER PUBLICATIONS

Lin et al., "Colorimetric Determination of the Purity of 39-Phospho Adenosine 59-Phosphosulfate and Natural Abundance of 39-Phospho Adenosine 59-Phosphate at Picomole Quantities," Anal. Biochem., vol. 264, pp. 111-117 (1998).
Lin et al., "Enzymatic Synthesis and Regeneration of 3'-Phosphoadenosine 5'Phosphosulfate (PAPS) for Regioselective Sulfation of Oligosaccharides," J. Am. Chem. So., vol. 117, pp. 8031-8032 (1995).
Lindahl et al., "Regulated Diversity of Heparan Sulfate," The Journal of Biological Chemistry, vol. 273, No. 39, pp. 24979-24982 (Sep. 25, 1998).
Lindahl et al., "Generation of "Neoheparin" from *E. coli* K5 Capsular Polysaccharide," J. Med. Chem., vol. 48, pp. 349-352 (2005).
Lindahl, U.; Backstrom, G.; Thunberg, L.; Leder, I. G. Proc. Natl. Acad. Sci. 1980, 77, 6551.
Linhardt et al., "Production and Chemical Processing of Low Molecular WQeight Heparins," Seminars in Thrombosis and Hemostasis, vol. 25, Suppl.3, pp. 5-16 (1999).
Linhardt, R. J., J. Med. Chem., vol. 46, pp. 2551-2564 (2003).
Liu et al., "Anticoagulant heparan sulfate: structural specificity and biosynthesis," Appl Microbiol Biotechnol., vol. 74, pp. 263-272 (2007).
Liu et al., "Cell Surface Heparan Sulfate and Its Roles in Assisting Viral Infections," Medicinal Research Reviews, vol. 22, No. 1, pp. 1-25 (2002).
Liu et al., "Characterization of a Heparan Sulfate Octasaccharide that Binds to Herpes Simplex Virus Type 1 Glycoprotein D," The Journal of Biological Chemistry, vol. 277, No. 36, pp. 33456-33467 (Sep. 6, 2002).
Liu et al., "Expression of Heparan Sulfate D-Glucosaminyl 3-O-Sulfotransferase Isoforms Reveals Novel Substrate Specificities," The Journal of Biological Chemistry, vol. 274, No. 8, pp. 5185-5192 (Feb. 19, 1999).
Liu et al., "Heparan Sulfate D-Glucosaminyl 3-O-Sulfotransferase-3A Sulfates N-Unsubstituted Glucosamine Residues," The Journal of Biological Chemistry vol. 274, No. 53, pp. 38155-38162 (Dec. 31, 1999).
Liu et al., "Purification of Heparan Sulfate D-Glucosaminyl 3-O-Sulfotransferase," The Journal of Biological Chemistry, vol. 271, No. 43, pp. 27072-27082 (Oct. 25, 1996).
Liu et al., Chemoenzymatic Design of Heparan Sulfate Oligosaccharides, J Biol Chem, vol. 285, No. 44, pp. 34240-34249 (Oct. 29, 2010).
Liu et al., "Enzymatic Placement of 6-O-Sulfo Groups in Heparan Sulfate," Biochemistry 2011, 50, 4382-4391.
Liu et al., "Lessons learned from the contamination of heparin," Nat. Prod. Rep., vol. 26, pp. 313-321 (2009).
Liu, J. et al., Royal Society of Chemistry, "Chemoenzymatic synthesis of heparan sulfate and heparin", vol. 31, pp. 1676-1685 (Year: 2014).
Loganathan et al., "Structural Variation in the Antithrombin III Binding Site Region and Its Occurrence in Heparin from Different Sources," Biochemistry, vol. 29, pp. 4362-4368 (1990).
Lu et al., "Innate Immune Regulations and Liver Ischemia-Reperfusion Injury." Transplantation, vol. 100, pp. 2601-2610 (2016).
Lundbäck et al., "A novel high mobility group box 1 neutralizing chimeric antibody attenuates drug-induced liver injury and postinjury inflammation in mice." Hepatology vol. 64, pp. 1699-1710 (2016).
Maccarana et al., J. Biol. Chem., vol. 268, pp. 23898-23905 (1993).
Mackman, "Triggers, targets and treatments for thrombosis," Nature, vol. 451, No. 21, pp. 914-918 (Feb. 21, 2008).
Mahe, I.; Chidac, J.; Helfer, H.; Nobel, S. J. Thromb. Haemost. 2016, 14, 2107.
Man et al., "Tolerance of the liver to intermittent pringle maneuver in hepatectomy for liver tumors." JAMA Sirgery, vol. 134, pp. 533-539 (1999).
Marcus et al. Anal. Biochem., vol. 107, pp. 296-304 (1980).

Marshall et al., "A review of the effects of manipulation of the cysteine residues of rat aryl sulfotransferase IV," Chem. Biol. Interact., vol. 109, pp. 107-116 (1998).
Marshall et al., "Control of Activity through Oxidative Modification at the Conserved Residue Cys66 of Aryl Sulfotransferase IV," J. Biol. Chem., vol. 272, No. 14, pp. 9153-9160 (Apr. 14, 1997).
Martinez-Gonzalez et al., "New Challenges for a Second-Generation Low-Molecular-Weight Heparin: Focus on Bemiparin," Expert Rev. Cardiovasc. Ther., vol. 8, No. 5, pp. 625-634 (2010).
Mazany et al., "Human chondroitin 6-sulfotransferase: cloning, gene structure, and chromosomal localization," Biochimica et Biophysica Acta, vol. 1407, pp. 92-97 (1998).
McGowan, K. E.; Makari, J.; Diamantouros, A.; Bucci, C.; Rempel, P.; Selby, R.; Geerts, W. Blood 2016, 127, 1954.
Monneau et al., "The sweet spot: how GAGs help chemokines guide migrating cells." J. Leukoc. Biol. vol. 99, pp. 935-953 (2016).
Moon et al., "Dissecting the substrate recognition of 3-0-suflotransferase for the biosynthesis of anticoagulant heparin," Proceedings of the National Academy of Sciences, vol. 109, No. 14, pp. 5265-5270 (2012).
Moon et al., "Structural Analysis of the Sulfotransferase (3-O-Sulfotransferase Isoform 3) Involved in the Biosynthesis of an Entry Receptor for Herpes Simplex Virus 1," J. Biol. Chem., vol. 279, No. 43, pp. 45185-45193 (2004).
Mossanen et al., "Acetaminophen-induced acute liver injury in mice." Lab. Anim. vol. 49, pp. 30-36 (2015).
Mousa, "Drug Discovery and Evaluation: Pharmacological Assays" (ed. Vogel, H.), 393-456 (Springer-Verlag Berlin, Heidelberg, New York (2008).
Mousa, "Heparin and Low-Molecular Weight Heparins in Thrombosis and Beyond," Meth. Mol. Biol., vol. 663, pp. 109-132 (2010).
Mousa, "In Vitro Methods of Evaluating Antithrombotics and Thrombolytics," Meth. Mol. Biol., vol. 663, pp. 1-28 (2010).
Munoz et al., "Enzymatic synthesis of heparin related polysaccharides on sensor chips: Rapid screening of heparin-protein interactions," Biochemical and Biophysical Research Communications, Academic Press Inc., Orlando, FL, US, vol. 339, No. 2, pp. 597-602 (Jan. 13, 2006).
Nam et al., "Syndecan-1 Limits the Progression of Liver Injury and Promotes Liver Repair in Acetaminophen-Induced Liver Injury in Mice." Hepatology, vol. 66(5), pp. 1601-1615, doi: 10.1002/hep. 29265 (2017).
Nastuk et al., "Expression Cloning and Characterization of NSIST, a Novel Sulfotransferase Expressed by a Subset of Neurons and Postsynaptic Targets," The Journal of Neuroscience, vol. 18, No. 18, pp. 7167-7177 (Sep. 15, 1998).
Needleman et al., "A General Method Applicable to the Search for Similarities in the Amino Acid Sequence of Two Proteins," J. Mol. Biol., vol. 48, pp. 443-453 (1970).
Nicola et al., Structure-Function Analysis of Soluble Forms of Herpes Simplex Virus Glycoprotein D., J. Virol., vol. 70, No. 6, pp. 3815-3822 (1996).
Noti et al., "Chemical Approaches to Define the Review Structure-Activity Relationship of Heparin-like Glycosaminoglycans," Chemistry & Biology, vol. 12, pp. 731-756 (Jul. 2005).
Notice of Allowance and Interview Summary corresponding to U.S. Appl. No. 14/898,865 dated Dec. 15, 2017.
Notice of Allowance corresponding to U.S. Appl. No. 13/996,930 dated Aug. 11, 2021.
Notice of Issuance corresponding to Chinese Patent Application No. 201480044429.9 dated May 7, 2021.
Notification Concerning of Transmittal of International Preliminary Report on Patentability for International Application No. PCT/US2006/018778 (dated Nov. 22, 2007).
Notification of Transmittal of the International Search Report and the Written Opinion of the International Searching Authority, or the Declaration corresponding to International Application No. PCT/US2008/008945 (dated Feb. 20, 2009).
Notification of Transmittal of the International Search Report and the Written Opinion of the International Searching Authority, or the Declaration corresponding to International Application No. PCT/US2011/066843 dated Aug. 22, 2012.

(56) References Cited

OTHER PUBLICATIONS

Notification of Transmittal of the International Search Report and the Written Opinion of the International Searching Authority, or the Declaration for International Application No. PCT/US06/18778 (dated Feb. 21, 2007).
Oduah et al., "Heparin: Past, present, and future." Pharmaceuticals (Basel), vol. 9, Article No. 38 (2016).
Office Action (Restriction Requirement) corresponding to U.S. Appl. No. 16/761,159 dated Jun. 10, 2022.
Office Action corresponding to Chinese Patent Application No. 201480044429.9 dated Apr. 9, 2019.
Office Action corresponding to Chinese Patent Application No. 201480044429.9 dated Aug. 30, 2018.
Office Action corresponding to Chinese Patent Application No. 201480044429.9 dated Mar. 3, 2020.
Office Action corresponding to Chinese Patent Application No. 201880020095.X dated Sep. 22, 2021.
Office Action corresponding to European Patent Application No. 11849994.6 dated Jan. 22, 2020.
Office Action corresponding to European Patent Application No. 11849994.6 dated May 24, 2018.
Office Action corresponding to European Patent Application No. 14812890.3 dated Jun. 23, 2020.
Office Action corresponding to Japanese Patent Application No. 2016-521505 dated Jul. 19, 2018.
Office Action corresponding to Japanese Patent Application No. 2016-521505 dated Jun. 21, 2019.
Office Action corresponding to Japanese Patent Application No. 2019-549419 dated Mar. 28, 2022.
Office Action corresponding to U.S. Appl. No. 12/178,434 dated Apr. 19, 2011.
Office Action corresponding to U.S. Appl. No. 12/178,434 dated Jan. 26, 2011.
Office Action corresponding to U.S. Appl. No. 12/178,434 dated Oct. 28, 2011.
Office Action corresponding to U.S. Appl. No. 13/996,930 dated Dec. 21, 2017.
Office Action corresponding to U.S. Appl. No. 13/996,930 dated Jul. 30, 2018.
Office Action corresponding to U.S. Appl. No. 13/996,930 dated May 26, 2016.
Office Action corresponding to U.S. Appl. No. 13/996,930 dated Nov. 22, 2019.
Office Action corresponding to U.S. Appl. No. 13/996,930 dated Oct. 8, 2015.
Official Action corresponding to U.S. Appl. No. 11/920,319 dated Apr. 28, 2010.
Official Action corresponding to U.S. Appl. No. 14/898,865 dated Mar. 23, 2017.
Oliveira et al., "Neutrophils: a cornerstone of liver ischemia and reperfusion injury." Lab. Invest., vol. 98, pp. 51-62 (2018).
Ong et al., "Expression Cloning of a Human Sulfotransferase that Directs the Synthesis of the HNK-1 Glycan on the Neural Cell Adhesion Molecule and Glycolipids," The Journal of Biological Chemistry, vol. 273, No. 9, pp. 5190-5195 (Feb. 27, 1998).
Onufriev, A; Bashford, D.; Case, D. A Proteins 2004, 55, 383.
Ornitz et al., "Receptor Specificity of the Fibroblast Growth Factor Family," J. Biol. Chem., vol. 271, No. 25, pp. 15292-15297 (1996).
Ouyang et al., "Molecular Cloning and Expression of Human and Mouse Tyrosylprotein Sulfotransferase-2 and a Tyrosylprotein Sulfotransferase Homologue in Caenorhabditis elegans," The Journal of Biological Chemistry, vol. 273, No. 38, pp. 24770-24774 (Sep. 18, 1998).
Ozawa et al., "Nucleotide sequence of a full-length cDNA (PST-1) for aryl sulfotransferase from rat liver," Nucleic Acids Res., vol. 18, No. 13, p. 4001 (1990).
Park et al., "Cell surface heparan sulfate proteoglycans: selective regulators of ligand-receptor encounters." J. Biol. Chem. vol. 275, pp. 29923-29926 (2000).
Patel, V. N.; Lombaert, I. M.A.; Cowherd, S. N.; Shworak, N.; Xu, Y.; Liu, J.; Hoffman, M. P. Developmental Cell 2014, 29, 662.
Pempe, et al., "Probing Structural Selectivity of Synthetic Heparin Binding to Stabilin Protein Receptors," Journal of Biol. Chem., vol. 287, No. 25, pp. 20774-20783 (Jun. 15, 2012).
Petitou et al., "A Synthetic Antithrombin III Binding Pentasaccharide Is Now a Drug! What Comes Next?" Angew. Chem. Int. Ed., vol. 43, pp. 3118-3133 (2004).
Petitou et al., "Synthesis of thrombin-inhibiting heparin mimetics without side effects." Nature, vol. 398, pp. 417-422 (Apr. 1, 1999).
Pettersen, E. F.; Goddard, T. D.; Huang, C. C.; Couch, G. S.; Greenblatt, D. M.; Meng, E. C.; Ferrin, T. E. J. Comp. Chem. 2004, 25, 1605.
Pierce et al., "Inflammatory response to trauma: implications for coagulation and resuscitation." Curr. Opin. Anesthesio., vol. 27, pp. 246-252 (2014).
Pinhal et al., "Enzyme interactions in heparan sulfate biosynthesis: Uronosyl 5-epimerase and 2-O-sulfotransferase interact in vivo.," Proc. Natl. Acad. Sci. U. S. A., vol. 98, No. 23, pp. 12984-12989 (Nov. 6, 2001).
Proudfoot et al., "Glycosaminoglycan binding and oligomerization are essential for the in vivo activity of certain chemokines." Proc. Natl. Acad. Sci. USA vol. 100, pp. 1885-1890 (2003).
Pye et al., "Heparan Sulfate Oligosaccharides Require 6-O-Sulfation for Promotion of Basic Fibroblast Growth Factor Mitogenic Activity," J. Biol. Chem., vol. 273, No. 36, pp. 22936-22942 (Sep. 4, 1998).
Raman, R.; Venkataraman, G.; Ernst, S.; Sasisekharan, R. Proc. Natl. Acad. Sci. 2003, 100, 2357.
Razi et al., "Structural and functional properties of heparin analogues obtained by chemical sulphation of *Escherichia coli* K5 capsular polysaccharide," Biochem. J., vol. 389, pp. 465-472 (1995).
Reizes et al., "Transgenic Expression of Syndecan-1 Uncovers a Physiological Control of Feeding Behavior by Syndecan-3," Cell, vol. 106, pp. 105-116 (Jul. 13, 2001).
Rosenberg et al., "Heparan Sulfate Proteoglycans of the Cardiovascular System Specific Structures Emerge But How Is Synthesis Regulated?" J. Clin. Invest., vol. 99, No. 9, pp. 2062-2070 (May 1997).
Saeki et al., "Molecular Cloning, Expression, and Characterization of a Novel Mouse Liver SULT1B1 Sulfotransferase," J. Biochem., vol. 124, pp. 55-64 (1998).
Sala et al., "UDP-N-trifluoroacetylglucosamine as an alternative substrate in N-acetylglucosaminyltransferase reactions", Carbohydrate Research, vol. 306, pp. 127-136 (1998).
Saribas et al., "Production of N-sulfated 1-38 polysaccharides using yeast-expressed N-deacetylase/N-sulfotransferase-1 (NDST-I)," Glycobiology, vol. 14, pp. 1217-1228 (2004).
Sarris et al., "Inflammatory chemokines direct and restrict leukocyte migration within live tissues as glycan-bound gradients." Curr. Biol. vol. 22, pp. 2375-2382 (2012).
Sasisekharan et al., "Roles of Heparan-Sulphate Glycosaminoglycans in Cancer," Nat. Rev. Cancer, vol. 2, pp. 521-528 (Jul. 2002).
Sattelle, B. M.; Almond, A. Glycobiology 2011, 21, 1651.
Sattelle, B. M.; Hansen, S. U.; Gardiner, J. M.; Almond, A. J Am Chem Soc 2010, 132, 13132.
Schroeder et al., "Protamine neutralization of low molecular weight heparins and their oligosaccharide components," Anal Bioanal Chem, vol. 399, pp. 763-771 (2011).
Schwartz et al., "Virogenic BrdU and BrdU-sensitive DNA sequences are disproportionately concentrated in the template-active chromatin of rat embryo cells," Nuc Acids Res., vol. 6, No. 2, pp. 745-755 (Feb. 1979).
Schworer, R.; Zubkova, O. V.; Turnbull, J. E.; Tyler, P. C. Chem. Eur. J. 2013, 19, 6817.
Sheng et al., "Influenced of Phenylalanines 77 and 138 on the Stereospecifity of Aryl Sulfotransferase IV," Drug Metabol. Dispos., vol. 32, No. 5, pp. 559-565 (2004).
Sheng et al., "The Dominating Role of N-Deacetylase/N-Sulfotransferase 1 in Forming Domain Structures in Heparan Sulfate," The Journal of Biological Chemistry, vol. 286, No. 22, pp. 19768-19776 (Jun. 3, 2011).

(56) References Cited

OTHER PUBLICATIONS

Shively et al., "Formation of Anhydrosugars in the Chemical Depolymerization of Heparin," Biochemistry, vol. 15, No. 18, pp. 3932-3942 (1976).
Shriver et al., "Glycomics: A Pathway to a Class of New and Improved Therapeutics," Nat. Rev. Drug Discov., vol. 3, pp. 863-873 (Oct. 2004).
Shukla et al., "A Novel Role for 3-O-Sulfated Heparan Sulfate in Herpes Simplex Virus 1 Entry," Cell, vol. 99, pp. 13-22 (Oct. 1, 1999).
Shukla et al., "Herpes viruses and heparan sulfate: an intimate relationship in aid of viral entry," The Journal of Clinical Investigation, vol. 108, No. 4, pp. 503-510 (Aug. 2001).
Shworak et al., "Molecular Cloning and Expression of Mouse and Human cDNAs Encoding Heparan Sulfate D-Glucosaminyl 3-O-Sulfotransferase," The Journal of Biological Chemistry, vol. 272, No. 44), pp. 28008-28019 (1997).
Singh, A; Tessier, M. B.; Pederson, K.; Wang, X.; Venot, A P.; Boons, G.-J.; Prestegard, J. H.; Woods, R. J. Can. J. Chem. 2016, 10.1139/cjc.
Sismey-Ragatz, et al, "Chemoenzymatic Synthesis with Distinc Pasteurella Heparosan Synthases," J. Biol. Chem., vol. 282, No. 39, pp. 28321-28327 (Jul. 11, 2007).
Smeds et al., "Substrate specificities of mouse heparan sulphate glucosaminyl 6-O-sulphotransferases," Biochem. J, vol. 372, pp. 371-380 (2003).
Smith et al., "Comparison of Biosequences," Adv. Appl. Math, vol. 2, pp. 482-489 (1981).
STN record for Chen et al., dissertation, "Towards de novo synthesis of structure-defined oligosaccharides with heparan sulfate u biosynthetic enzymes", entered into STN: Apr. 20, 2009. 1 page.
Sundaram, M. et al., "Rational design of low-molecular weight heparins with improved in vivo activity," Proc. Natl. Acad. Sci., vol. 100, No. 2, pp. 651-656 (Jan. 21, 2003).
Supplemental Notice of Allowability and Interview Summary corresponding to U.S. Appl. No. 14/898,865 dated Jan. 12, 2018.
Szajek et al., "The US regulatory and pharmacopeia responses to the global heparin contamination crisis." Nat. Biotechnol. vol. 34, pp. 625-630 (2016).
Tecle, E.; Diaz-Balzac, C. A.; Bulow, H. E. G3 (Bethesda) 2013, 3, 541.
Teng et al., "Molecular functions of syndecan-1 in disease." Matrix Biol., vol. 31, pp. 3-16 (2012).
Thacker, B. E.; Seamen, E.; Lawrence, R.; Parker, M. W.; Xu, Y.; Liu, J.; Vander, K. C. W.; Eska, J. D. ACS Chem. Biol. 2016, 11, 971.
Thompson et al., "CLUSTAL W: improving the sensitivity of progressive multiple sequence alignment through sequence weighting, position-specific gap penalties and weight matrix choice," Nucleic Acids Res., vol. 22, No. 22, pp. 4673-4680 (1994).
Tohu et al., Anti-Xa and Anti-IIa Drugs Alter International Normalized Ratio Measurements: Potential Problems in the Monitoring of Oral Anticoagulants Clin. Appl. Thrombos Hemostas, vol. 10, pp. 301-309 (2004).
Tsau, C.; Ito, M.; Gromova, A.; Hoffman, M. P.; Meech, R.; Makarenkova, H. P. Development 2011, 138, 3307.
Tsung et al., "HMGB1 release induced by liver ischemia involves Toll-like receptor 4-dependent reactive oxygen species production and calcium-mediated signaling." J. Exp. Med., vol. 204, pp. 2913-2923 (2007).
Tsung et al., "The nuclear factor HMGB1 mediates hepatic injury after murine liver ischemia-reperfusion." J. Exp. Med., vol. 201, pp. 1135-1143 (2005).
Uchimura et al., "Molecular Cloning and Characterization of an N-Acetylglucosamine-6-O-sulfotransferase," The Journal of Biological Chemistry, vol. 273, No. 35, pp. 22577-22583 (Aug. 28, 1998).
Vann et al., "The Structure of the Capsular Polysaccharide (K5 Antigen) of Urinary-Tract-Infective *Escherichia coli* 010 : K5 : H4 A Polymer Similar to Desulfo-Heparin," Eur. J. Biochem, vol. 116, pp. 359-364 (1981).
Venereau et al., "HMGB1 as biomarker and drug target." Pharmacol. Res. vol. 111, pp. 534-544 (2016).
Wang et al., "*E. coli* K5 fermentation and the Preparation of Heparosan, a Bioengineered Heparin Precursor," Biotechnol. Bioeng, vol. 107, No. 7, pp. 968-977 (Dec. 15, 2010).
Wang et al., "Edothelial heparan sulfate deficiency impairs L-selectin- and chemokine-mediated neutrophil trafficking during inflammatory responses." Nat. Immunol. vol. 6, pp. 902-910 (2005).
Weber et al., "Renal dysfunction in liver transplant recipients: Evaluation of the critical issues." Liver Transplant., vol. 18, pp. 1290-1301 (2012).
Weitz et al, "Beyond heparin and warfarin: the new generation of anticoagulants," Expert Opin. Investig. Drugs, vol. 16, No. 3, pp. 271-282 (2007).
Weitz, "Potential of new anticoagulants in patients with cancer," Thromb. Res., vol. 125 (Suppl 2), pp. S30-S35 (2010).
Wildhagen et al., "Nonanticoagulant heparin prevents histone-mediated cytotoxicity in vitro and improves survival in sepsis." Blood vol. 123, pp. 1098-1101 (2014).
Willis et al., "Examination of the Kinetics of Herpes Simplex Virus Glycoprotein D Binding to the Herpesvirus Entry Mediator, Using Surface Plasmon Resonance," J. Virol., vol. 72, pp. 5938-5947 (Jul. 1998).
Wishart et al., "A single mutation converts a novel phosphotyosine binding domain into a dual-specificity phosphatase," J. Biol. Chem., vol. 270, No. 45, pp. 26782-26785 (1995).
Witkowski et al., "Conversion of b-ketoacyl synthase to a Malonyl Decarboxylase by replacement of the active cysteine with glutamine," Biochemistry, vol. 38, pp. 11643-11650 (1999).
Written Opinion of the International Searching Authority Corresponding to International Application No. PCT/US 2018/021986 dated Aug. 1, 2018.
WuDunn et al., "Initial interaction of herpes simplex virus with cells is binding to heparan sulfate," J. Virol., vol. 63, No. 1, pp. 52-58 (1989).
Xia et al., "Heparan Sulfate 3-O-Sulfotransferase Isoform 5 Generates Both an Antithrombin-binding Site and an Entry Receptor for Herpes Simplex Virus, Type 1," J. Biol. Chem., vol. 277, No. 40, pp. 37912-37919 (2002).
Xu et al., "Characterization of heparan sulphate 3-O-sulphotransferase isoform 6 and its role in assisting the entry of herpes simplex virus type 1," Biochem. J., vol. 385, pp. 451-459 (2005).
Xu et al., Chemoenzymatic Synthesis of Homogeneous Ultralow Molecular Weight Heparins, Science, vol. 334, pp. 498-501 (Oct. 2011).
Xu et al., "Heparan sulfate is essential for high mobility group protein 1 (HMGB1) signaling by the receptor for advanced glycation end products (RAGE)." J. Biol. Chem. vol. 286, pp. 41736-41744 (2011).
Xu et al., "Homogeneous low-molecular-weight heparins with reversible anticoagulant activity." Nat. Chem. Biol. vol. 10, pp. 248-250 (2014).
Xu et al., Synthetic oligosaccharides can replace animal-sourced low-molecular weight heparins Sci. Transl. Med. vol. 9, eaan5954 (2017).
Xu, D. et al., "Engineering sulfotransferases to modify heparan sulfate," Nat Chem Biol, vol. 4, No. 3, pp. 200-202 (Mar. 2008).
Xu, D.; Esko, "Demystifying Heparan Sulfate-Protein Interactions," J. Annu Rev Biochem. 2014, 83, 129.
Xu, D.; Olson, J.; Cole, J. N.; van Wijk, X. M.; Brinkmann, V.; Zychlinsky, A.; Nizet, V.; Eska, J. D.; Chang, Y. C. Infect. Immun. 2015, 83, 3648.
Xu, et. al., "Homogeneous low-molecular-weight heparins with reversible anticoagulant activity," Nat Chem Biol., vol. 10, pp. 248-252 (2014).
Yang et al. Effects of 3'-phosphoadenosine 5'-phosphate on the activity and folding of phenol sulfotransferase. Chem.-Biol. Interact. 109: 129-135 (1998).

(56) References Cited

OTHER PUBLICATIONS

Yang et al., "Two Phenol Sulfotransferase Species from One cDNA: Nature of the Differences," Protein Expression Purif, vol. 8, pp. 423-429 (1996).
Yang, J.; Hsieh, P.; Liu, X.; Zhou, W.; Zhang, X.; Zhao, J.; Xu, Y.; Zhang, F.; Linhardt, R. J.; Liu, J. Chem Comm 2017, 53, 1743.
Yang, Z.; Lasker, K.; Schneidman-Duhovny, D.; Webb, B.; Huang, C. C.; Pettersen, E. F.; Goddard, T. D.; Meng, E. C.; Sali, A; Ferrin, T. E. J. Struct. Biol. 2012, 179, 269.
Yoshinari et al., "Molecular Cloning, Expression, and Enzymatic Characterization of Rabbit Hydroxysteroid Sulfotransferase AST-RB2 (ST2A8)," J. Biochem., vol. 123, pp. 740-746 (1998).
Zhang et al., "6-O-Sulfotransferase-1 Represents a Critical Enzyme in the Anticoagulant Heparan Sulfate Biosynthetic Pathway*," J. Biol. Chem., vol. 276, pp. 42311-42321 (2001).
Zhang et al., "Solution Structures of Chemoenzymatically Synthesized Heparin and Its Precursors," J. Am. Chem. Soc., vol. 130, pp. 12998-13007 (2008).
Zhang et al., "The Effect of Precursor Structures on the Action of Glucosaminyl 3-O-Sulfotransferase-1 and the Biosynthesis of Anticoagulant Heparan Sulfate," J. Biol. Chem., vol. 276, No. 31, pp. 28806-28813 (2001).
Zhao et al. "Enzymatic route to preparative-scale synthesis of UDP-GlcNAc/GalNAc, their analogues and GDP-fucose," Nat. Protoc., vol. 5, No. 4, pp. 636-646 (2010).
Zhou et al. "Expression of heparin sulfate sulfotransferases in Kluyveromyces lactis and preparation of 3'-phsphoadenosie-5'-phosphosulfate," Glycobiology, vol. 21, No. 6, pp. 771-780 (2011).
Zitvogel et al., "Decoding cell death signals in inflammation and immunity." Cell, vol. 140, pp. 798-804 (2010).
Zong, C.; Huang, R.; Condac, E.; Chiu, Y.; Xiao, W.; Li, Z. Q.; Lu, W.; Ishihara, M.; Wang, S.; Ramiah, A.; Stickney, M.; Azadi, P.; Amster, I. J.; Moremen, K. W.; Wang, L.; Sharp, J. S.; Boons, G.-J. J. Am. Chem. Soc. 2016, 138, 13059.
Belot, F. et al., "Syntheses of chondroitin 4- and 6-sulfate pentasaccharide derivatives having a methyl beta-D-glucopyranosiduronic acid at the reducing end" Carbohyd. Res., vol. 326, pp. 88-97. (Year: 2000).
Beeson et al., "Inhibition of Binding of Malaria-Infected Erythrocytes by a Tetradecasaccharide Fraction from Chondroitin Sulfate A," Infection and Immunity vol. 66 No. 7 pp. 3397-3402 (Year: 1998).
Bourgeaux et al., "Two-step enzymatic synthesis of UDP-N-acetylgalactosamine." Bioorg. Med. Chem. Lett., vol. 15, pp. 5459-5462 (2005).
Bradbury et al., "Chondroitinase ABC promotes functional recovery after spinal cord injury." Nature, vol. 416, pp. 636-640 (2002).
Brinkmann V, Reichard U, Goosmann C, Fauler B, Uhlemann Y, Weiss DS, et al. Neutrophil extracellular traps kill bacteria. Science. 2004;303:1532-5.
Brown et al., "A sulfated carbohydrate epitope inhibits axon regeneration after injury." Proc. Natl. Acad. Sci. USA, vol. 109, pp. 4768-4773 (2012).
Chan et al., "Regulation of PfEMP1-VAR2CSA translation by a Plasmodium translation-enhancing factor." Nature Microbiology, vol. 2, Article No. 17068 (2017).
Clark SR, Ma AC, Tavener SA, McDonald B, Goodarzi Z, Kelly MM, et al. Platelet TLR4 activates neutrophil extracellular traps to ensnare bacteria in septic blood. Nat Med. 2007;13:463-9.
Coutant et al., "2-Deoxy-2-trichloroacetamido-D-glucopyranose derivatives in oligosaccharide synthesis: from hyaluronic acid to chondroitin 4-sulfate trisaccharides" J Chem Soc Perkin Trans 1 (1995) 1573-1581 (Year: 1995).
Eller et al., "Automated Solid-Phase Synthesis of Chondroitin Sulfate Glycosaminoglycans." Angew. Chem. Int. Ed., vol. 52, pp. 5858-5861 (2013).
Extended European Search Report Corresponding to European Patent Application No. 19822610.2 dated Mar. 29, 2022.
Freeman et al., "The accumulation of circulating histones on heparan sulphate in the capillary glycocalyx of the lungs." Biomater., vol. 34, pp. 5670-5676 (2013).
Fried et al., "Designing a VAR2CSA-based vaccine to prevent placental malaria." Vaccine, vol. 33, pp. 7483-7488 (2015).
Goddard-Borger et al., "An Efficient, Inexpensive and Shelf-Stable Diazotransfer Reagent: Imidazole-1-sulfonyl Azide Hydrochloride." Org. Lett., vol. 9, pp. 3797-3800 (2007).
Habuchi et al., "Purification of Chondroitin 6-Sulfotransferase Secreted from Cultured Chick Embryo Chondrocytes," The Journal of Biological Chemistry, vol. 268(29), pp. 21968-21974 (1993).
International Preliminary Report on Patentability corresponding to International Application No. PCT/US2018/040774 dated Jan. 16, 2020.
International Preliminary Report on Patentability corresponding to International Application No. PCT/US2019/037993 dated Oct. 18, 2019.
International Search Report corresponding to International Application No. PCT/US2019/037993 dated Oct. 18, 2019.
Laremore, T. et al "Ionic liquid matrix for direct UV-MALDI-TOF-MS Analysis of Dermatan Sulfate and Chondroitin Sulfate Oligosaccharides." Anal. Chem., vol. 79, pp. 1604-1610. (Year: 2007).
Li et al., "Enzymatic Synthesis of Homogeneous Chondroitin Suifate Oligosaccharides." Angew. Chemie., vol. 129(39), pp. 11946-11949 (2017).
Li et al., "Enzymatic synthesis of homogenous chondroitin suifate e oligosaccharides." Glycobiol., vol. 28(12) (2018).
Lopin et al., "From Polymer to Size-Defined Oligomers: An Expeditious Route for the Preparation of Chondroitin Oligosaccharides." Angew. Chem. Int. Ed., vol. 45, pp. 2574-2578 (2006).
Lopin-Bon et al., "Stereocontroiled preparation of biotinylated chondroitin sulfate E di-, tetra-, and hexasaccharide conjugates." Carbohydr. Res., vol. 402, pp. 35-43 (2015).
Ly et al., "The proteoglycan bikunin has a defined sequence." Nat. Chem. Biol, vol. 7. pp. 827-833 (2011).
Macchione et al., "Synthesis of chondroitin suifate oligosaccharides using N-tetrachlorophthaloyl and N-triffuoroacetyl galactosamine building blocks," European Journal of Organic Chemistry, pp. 3868-3884 (2014).
Maza et al., "Synthesis of chondroitin/dermatan sulfate-like oligosaccharides and evaluation of their protein affinity by fluorescence polarization." Org. Biomol. Chem., vol. 11, pp. 3510-3525 (2013).
Miyachi et al., "Syntheses of chondroitin sulfate tetrasaccharide structures containing 4,6-disulfate patterns and analysis of their interaction with glycosaminoglycan-binding protein." Bioorg. Med. Chem. Lett., vol. 25, pp. 1552-1555 (2015).
Miyata et al., "Persistent cortical plasticity by upregulation of chondroitin 6-sulfation." Nat. Neurosci., vol. 15, pp. 414-422 (2012).
Mizumoto et al., "Molecular interactions between chondroitin—dermatan sulfate and growth factors/receptors/matrix proteins." Curr. Opin. Struct. Biol, vol. 34, pp. 35-42 (2015).
Nadanaka et al., "Characteristic Hexasaccharide Sequences in Octasaccharides Derived from Shark Cartilage Chondroitin Sulfate D with a Neurite Outgrowth Promoting Activity," The Journal of Biological Chemistry, vol. 273(6), pp. 3296-3307 (1998).
Nagano et al., "Chondroitin sulfate protects vascular endothelial cells from toxicities of extracellular histones." Eur. J. Pharmacol., vol. 826, pp. 48-55 (2018).
Office Action (Final) corresponding to U.S. Appl. No. 16/625,342 dated Nov. 4, 2022.
Office Action (Restriction Requirement) corresponding to U.S. Appl. No. 16/625,342 dated Dec. 16, 2021.
Office Action corresponding to U.S. Appl. No. 16/625,342 dated Dec. 20, 2019.
Office Action (Restriction Requirement) corresponding to U.S. Appl. No. 17/254,145 dated Nov. 26, 2021.
Office Action (Decision of Rejection) corresponding to Chinese Patent Application No. 20180020095.X dated Dec. 1, 2022.
Office Action corresponding to U.S. Appl. No. 16/625,342 dated Mar. 21, 2022.
Office Action corresponding to U.S. Appl. No. 17/254,145 dated Feb. 16, 2022.

(56) References Cited

OTHER PUBLICATIONS

Pulsipher et al., "Directing Neuronal Signaling through Cell-Surface Glycan Engineering." J. Am. Chem. Soc., vol. 136, pp. 6794-6797 (2014).
Rohrmann et al., "Two N-acetylgalactosaminyltransferase are involved in the biosynthesis of chondroitin sulfate," European Journal of Biochemistry, vol. 148, pp. 463-469 (1985).
Roman-Blas et al., "The combined therapy with chondroitin sulfate plus glucosamine sulfate or chondroitin sulfate plus glucosamine hydrochloride does not improve joint damage in an experimental model of knee osteoarthritis in rabbits." Eur. J. Pharmacol, vol. 794, pp. 8-14 (2017).
Shiori et al., "Sequence determination of synthesized chondroitin sulfate dodecasaccharides." Glycobiology, vol. 26, pp. 592-606 (2016).
Solera et al., "Chondroitin sulfate tetrasaccharides: synthesis, three-dimensional structure and interaction with midkine." Chemistry, vol. 22, pp. 2356-2369 (2016).
Stabler et al., "Chondroitin sulphate inhibits NF-κB activity induced by interaction of pathogenic and damage associated molecules." Osteoarthritis and Cartilage, Voi. 25, pp. 166-174 (2017).
Sugigura et al., "Molecular dissection of placental malaria protein VAR2CSA interaction with a chemo-enzymatically synthesized chondroitin sulfate library." Glycoconj. J., vol. 33, pp. 985-994 (2016).
Sugigura et al., "Sequential synthesis of chondroitin oligosaccharides by immobilized chondroitin polymerase mutants." Glycoconj. J., vol. 25, pp. 521-530 (2008).
Sugiura et al., "Baculovirus Enveiope Protein ODV-E66 Is a Novel Chondroitinase with Distinct Substrate Specificity." J. Biol. Chem., vol. 286, pp. 29026-29034 (2011).
Sugiura et al., "Construction of a Chondroitin Sulfate Library with Defined Structures and Analysis of Molecular Interactions." J. Biol. Chem., vol. 287, pp. 43390-43400 (2012).
Sugumaran et al., "Simultaneous Sulfation of endogenous Chondroitin Suifate and Chondroitin-derived Oligosaccharides" The Journal of Biological Chemistry vol. 261 No. 27 pp. 12659-12664 (Year: 1986).
Takagaki et al., "Enzymatic Reconstruction of a Hybrid Glycosaminoglycan Containing 6-Sulfated, 4-Sulfated, and Unsulfated N-Acetylgalactosamine" Biochemical and Biophysical Research Communications vol. 258 pp. 741-744 (Year: 1999).
Tamura et al., "Synthesis of chondroitin sulfate E octasaccharide in a repeating region involving an acetamide auxiliary." Carbohydr. Res., vol. 343, pp. 39-47 (2008).
Wildhagen KC, Garcia de Frutos P, Reuteiingsperger CP, Schrijver R, Aresté C, Ortega-Gómez A, et al. Nonanticoagulant heparin prevents histone-mediated cytotoxicity in vitro and improves survival in sepsis. Blood. 2014;123:1098-101.
Written Opinion corresponding to International Application No. PCT/US2019/037993 dated Oct. 18, 2019.
Xu J, Zhang X, Monestier M, Esmon NL, and Esmon CT. Extracellular histones are mediators of death through TLR2 and TLR4 in mouse fatal liver injury. J Immunol. 2011;187:2626-31.
Xu J, Zhang X, Pelayo R, Monestier M, Ammollo CT, Semeraro F, et al. Extracellular histones are major mediators of death in sepsis. Nat Med. 2009;15:1318-21.
Xue et al., "Impact of donor binding on polymerization catalyzed by KfoC by regulating the affinity of enzyme for acceptor." Biochim. Biophys. Acta, vol. 1860, pp. 844-855 (2016).
Yang et al., "An Approach to Synthesize Chondroitin Suifate-E (CS-E) Oligosaccharide Precursors." J. Organic Chem., vol. 83, pp. 5897-5908 (2018).
Yang et al., "Middle region of the Borrelia burgdorferi surface-located protein 1 (Lmp1) interacts with host chondroitin-6-sulfate and independently facilitates infection." Cell Microbiology, vol. 18, 97-110 (2016).
Yu et al., "Highly Efficient Chemoenzymatic Synthesis of Beta1-3-Linked Galactosides," Chemical Communications, vol. 46(40), pp. 7507-7509 (2010).

Li et al., "Enzymatic Synthesis of Homogeneous Chondroitin Sulfate Oligosaccharides." Angew. Chemie., vol. 129(39), pp. 11946-11949 (2017).
Li et al., "Enzymatic synthesis of homogenous chondroitin sulfate e oligosaccharides." Glycobiol., vol. 28(12) (2018).
Lopin-Bon et al., "Stereocontrolled preparation of biotinylated chondroitin sulfate E di-, tetra-, and hexasaccharide conjugates." Carbohydr. Res., vol. 402, pp. 35-43 (2015).
Macchione et al., "Synthesis of chondroitin sulfate oligosaccharides using N-tetrachlorophthaloyl and N-trifluoroacetyl galactosamine building blocks," European Journal of Organic Chemistry, pp. 3868-3884 (2014).
Stabler et al., "Chondroitin sulphate inhibits NF-κB activity induced by interaction of pathogenic and damage associated molecules." Osteoarthritis and Cartilage, vol. 25, pp. 166-174 (2017).
Sugiura et al., "Baculovirus Envelope Protein ODV-E66 Is a Novel Chondroitinase with Distinct Substrate Specificity." J. Biol. Chem., vol. 286, pp. 29026-29034 (2011).
Sugumaran et al., "Simultaneous Sulfation of endogenous Chondroitin Sulfate and Chondroitinderived Oligosaccharides" The Journal of Biological Chemistry vol. 261 No. 27 pp. 12659-12664 (Year: 1986).
Wildhagen KC, García de Frutos P, Reutelingsperger CP, Schrijver R, Aresté C, Ortega-Gómez A, et al. Nonanticoagulant heparin prevents histone-mediated cytotoxicity in vitro and improves survival in sepsis. Blood. 2014;123:1098-101.
Yang et al., "An Approach to Synthesize Chondroitin Sulfate-E (CS-E) Oligosaccharide Precursors." J. Organic Chem., vol. 83, pp. 5897-5908 (2018).
Yusa et al., "N-Linked Oligosaccharides on Chondroitin 6-Sulfotransferase-1 Are Required for Production of the Active Enzyme, Golgi Localization, and Sulfotransferase Activity toward Keratan Sulfate." J. Biol. Chem., vol. 281, pp. 20393-20403 (2006).
Office Action corresponding to Japanese Patent Application No. 2019-549419 dated Dec. 23, 2022 with pending claims.
Arnold, Biomedicines 2020, 8, 0503. (Year: 2020).
Communication of European publication number corresponding to European Patent application No. 20887629.2 dated Jul. 20, 2022.
Frank, Thromb Haemost 2006; 96:802-6. (Year: 2006).
International Search Report and the Written Opinion of the International Searching Authority Corresponding to International Application No. PCT/US2018/040774 dated Sep. 18, 2018.
Li et al., "Enzymatic synthesis of homogenous chondroitin sulfate e oligosaccharides," Abstract of Glycobiol., vol. 28(12) (2018) [Abstract].
Li J, Su W, and Liu J. "Enzymatic synthesis of homogeneous chondroitin sulfate oligosaccharides." Angew Chem Int Ed. 2017;56:11784-7.
Notice of Allowance corresponding to U.S. Appl. No. 17/254,145 dated Dec. 8, 2022.
Notice of Publication Corresponding to European Patent application No. 18764628.6 dated Nov. 20, 2019.
Notice of Publication Corresponding to European Patent Application No. 18873131.9 dated Jul. 15, 2020.
Office Action corresponding to Chinese Patent Application No. 2018800850125 dated Jan. 20, 2023.
Office Action corresponding to U.S. Appl. No. 16/761,159 dated Jan. 11, 2023.
Yang, "Inflammation plays a dual role in acetaminophen hepatotoxicity," Translational Medicine Journal,vol. 5, No. 3, pp. 129-133 (Jun. 2016).
Office Action corresponding to Japanese Patent Application No. 2020-544568 dated Jan. 10, 2023.
Office Action (Notice of Reasons for Rejection) corresponding to Japanese Patent Application No. 2020-570916 dated Jun. 20, 2023.
Office Action corresponding to Chinese Patent Application No. 2019800446973 dated Jul. 7, 2023.
Office Action corresponding to Chinese Patent Application No. 202080092892 dated Jun. 21, 2023.
Office Action corresponding to European Patent Application No. 18873131.9-1112 dated Aug. 14, 2023.
Office Action corresponding to U.S. Appl. No. 16/625,342 dated Jun. 15, 2023.

(56) References Cited

OTHER PUBLICATIONS

Shiver et al., (2012) "Heparin and Heparan Sulfate: Analyzing Structure and Microheterogeneity," Handb Exp. Pharmacol. (207): pp. 159-176.
Decision to Grant corresponding to Japanese Patent Application No. 2019549419 dated Jul. 11, 2023 with machine translation and set of allowed claims.
Notice of Allowance and Interview Summary corresponding to U.S. Appl. No. 17/254,145 dated Jan. 30, 2023.
Office Action corresponding to Chinese Patent Application No. 20180020095.X dated Apr. 18, 2023 with modified machine translation and set of pending claims.
Office Action corresponding to Chinese Patent Application No. 202310342719.2 dated May 8, 2023 with machine translation.
Office Action Corresponding to Japanese Patent Application No. 2020-544568 dated Sep. 26, 2023.

* cited by examiner

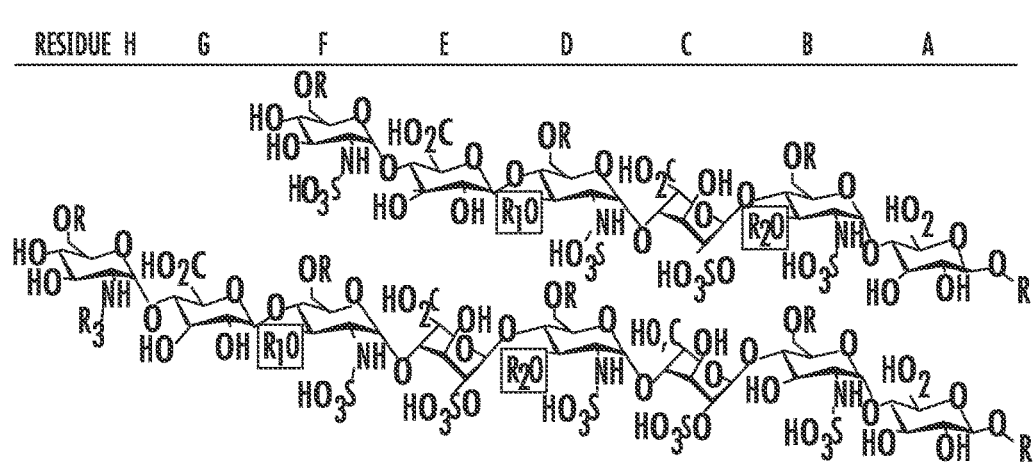

R = -H, -CH$_3$, -CH$_2$CH$_3$ OR 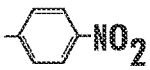

HEXASACCHARIDES (6-MERS):
COMPOUND 1: R = R$_1$ = -H; R$_2$ = -SO$_3$H
COMPOUND 2: R$_1$ = -H; R = R$_2$ = -SO$_3$H
COMPOUND 3: R = R$_1$ = R$_2$ = -SO$_3$H
COMPOUND 7: R = R$_1$ = R$_2$ = -H
COMPOUND 8: R = R$_1$ = -SO$_3$H; R$_2$ = -H

OCTASACCHARIDES (8-MERS):
COMPOUND 4: R = R$_1$ = -H; R$_2$ = -R$_3$ = -SO$_3$H
COMPOUND 5: R$_1$ = -H; R = R$_2$ = -R$_3$ = -SO$_3$H
COMPOUND 6: R = R$_1$ = R$_2$ = R$_3$ = -SO$_3$H
COMPOUND 9: R = R$_1$ = R$_2$ = -H; R$_3$ = -Ac
COMPOUND 10: R = R$_3$ = -SO$_3$H; R$_1$ = -R$_2$ = -H
COMPOUND 11: R$_2$ = -H; R$_1$ = -SO$_3$H; R$_3$ = -Ac R = -SO$_3$H

FIG. 1A

COMPOUND 3, MW = 1871.47

R = -H, -CH₃, -CH₂CH₃ OR

COMPOUND 4, MW = 2048.63

R = -H, -CH₃, -CH₂CH₃ OR

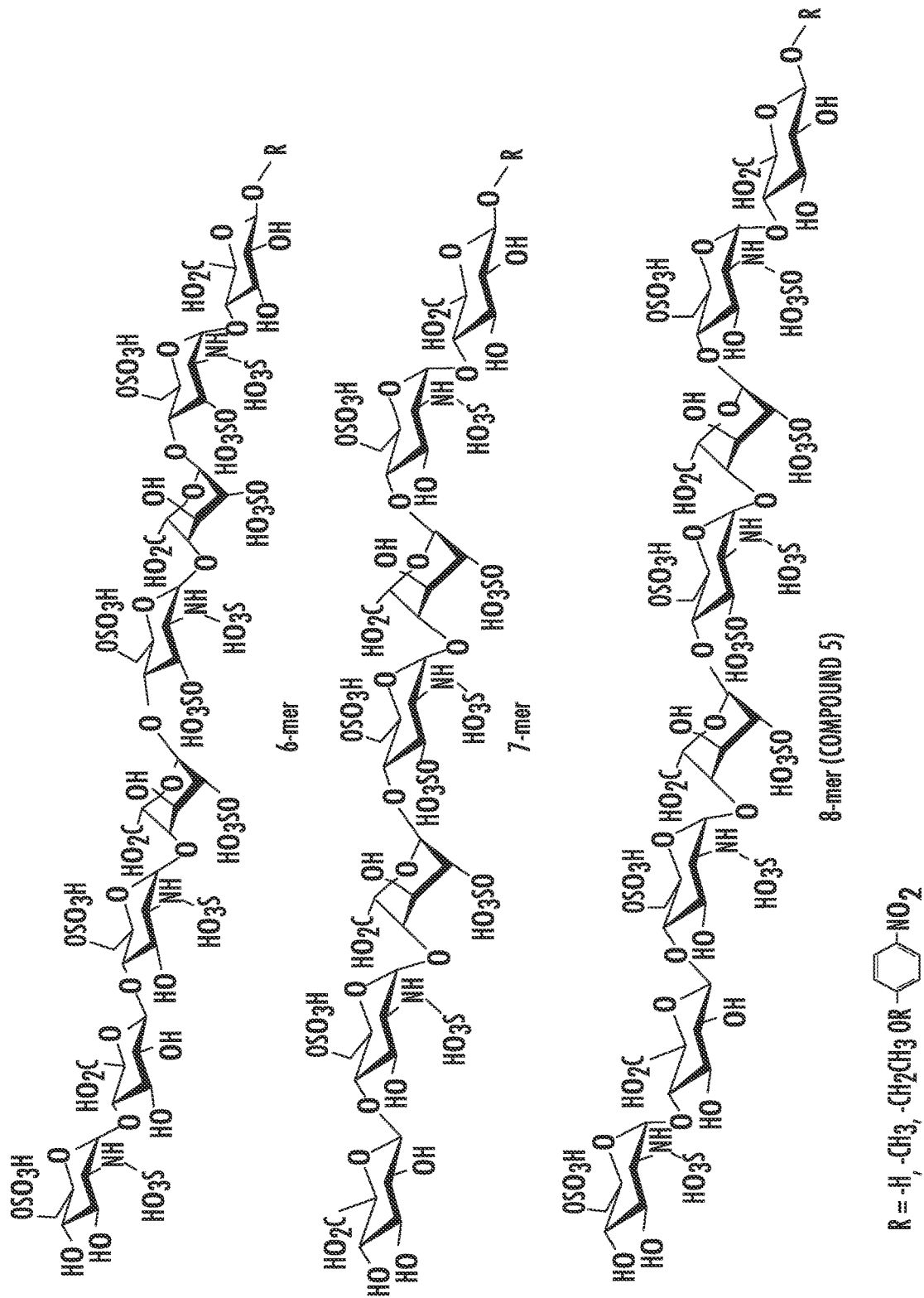

SHORT-ACTING HEPARIN-BASED ANTICOAGULANT COMPOUNDS AND METHODS

CROSS-REFERENCE TO RELATED APPLICATIONS

This application is a national phase patent application under 35 U.S.C. Section 371 of PCT International Patent Application No. PCT/US2018/021986, filed Mar. 12, 2018, which claims benefit of U.S. Provisional Patent Application Ser. No. 62/469,643, filed Mar. 10, 2017, herein incorporated by reference in its entirety.

GRANT STATEMENT

This invention was made with government support under Grant Numbers GM102137, HL094463, CA207824 and GM103390 awarded by the National Institutes of Health. The government has certain rights in the invention.

TECHNICAL FIELD

The subject matter disclosed herein relates generally to synthesis of heparin compounds. More particularly, the subject matter disclosed herein relates to chemoenzymatic synthesis of heparin compounds and synthetic heparin analogues having short acting anticoagulant activity.

BACKGROUND

Heparan sulfate (HS) is a ubiquitous component of the cell surface and extracellular matrix. It regulates a wide range of physiologic and pathophysiologic functions, including embryonic development and blood coagulation, and can facilitate viral infection (Esko and Selleck (2002) *Annu. Rev. Biochem.* 71, 435-471; Liu and Thorp (2002) *Med. Res. Rev.* 22, 1-25). HS exerts its biological effects by interacting with the specific proteins involved in a given process (Capila and Lindhardt (2002) *Angew. Chem. Int. Ed.* 41, 390-412). HS is a highly charged polysaccharide comprising 1→4-linked glucosamine and glucuronic/iduronic acid units that contain both N- and O-sulfo groups. Unique saccharide sequences within HS can determine the specificity of the binding of HS to its target proteins (Linhardt (2003) *J. Med. Chem.* 46, 2551-2564). Heparin, a specialized form of HS, is a commonly used anticoagulant drug. Thus, new methods for the synthesis of heparin compounds and HS attract considerable interest for those developing anticoagulant and other HS-related drugs having improved pharmacological effects.

Heparin has been successfully used as an anticoagulant drug for over 50 years (Mackman, 2008). It is currently marketed in three forms: unfractionated (UF) heparin ($MW_{avg}$~14000 Da); a low molecular weight heparin ($MW_{qvg}$~6000 Da); and the synthetic ULMW heparin pentasaccharide ARIXTRA® (MW 1508.3 Da). UF heparin is used in surgery and kidney dialysis due to its relatively short half-life and its safety for renal impaired patients (Hirsh et al., 2007).

The synthesis of HS oligosaccharides and related anticoagulant compounds remains a challenge. Cost-effective methods and approaches for synthesizing new synthetic heparins are highly desirable.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, provided herein are synthetic heparin analogues, comprising a 3-O-sulfated oligosaccharide comprising six to eight saccharide units, at least one disaccharide unit sulfated by a 3-OST-3 enzyme, and at least one IdoA2S-GlcNS3S or IdoA2S-GlcNS3S6S disaccharide unit. In some embodiments such synthetic heparin analogues can have an anticoagulant activity. In some embodiments such synthetic heparin analogues can have a binding affinity to antithrombin ranging from about 5 nM to about 30 nM. In some embodiments such synthetic heparin analogues can have anti-Xa activity ranging from about 10 ngml$^{-1}$ to about ngml$^{-1}$ IC$_{50}$.

In some aspects, the synthetic heparin analogues provided herein can contain at least one IdoA2S-GlcNS3S6S disaccharide unit, and be devoid of a GlcA-GlcNS3S6S disaccharide unit. In some embodiments such synthetic heparin analogues can have a clearance rate about 50% to about 100% faster than that of other heparin compounds. In some embodiments such synthetic heparin analogues do not cause heparin-induced thrombocytopenia (HIT). In some embodiments such synthetic heparin analogues are reversible by andexanet alfa at a rate of 50% or more in the presence of 20 ug/ml or less of andexanet alfa.

In some embodiments provided herein are methods of synthesizing a synthetic heparin analogue, comprising providing a saccharide substrate, elongating the saccharide substrate to a saccharide of a desired or predetermined length, and performing at least one sulfation reaction using a 3-OST-3 isoform of a 3-O-sulfotransferase (3-OST) enzyme, whereby a synthetic heparin analogue is synthesized. In some aspects the saccharide substrate comprises at least one IdoA2S-GlcNS3S disaccharide unit. In some aspects the saccharide substrate comprises a IdoA2S-GlcNS3S±6S disaccharide unit, wherein the method further comprises a 6-O-sulfation step using a 6-O-sulfotransferase (6-OST), wherein a 3-O-sulfation by 3-OST-3 occurs prior to the 6-O-sulfation step. In some aspects the saccharide substrate comprises a GlcA-GlcNS3S6S disaccharide unit, wherein the method further comprises a 6-O-sulfation step using a 6-O-sulfotransferase (6-OST), wherein a 3-O-sulfation by 3-OST-1 occurs prior to the 6-O-sulfation step.

In some aspects the elongation step comprises employing a glycosyl transferase. In some embodiments the glycosyl transferase is selected from the group consisting of N-acetyl glucosaminyl transferase of *E. coli* K5 (KfiA) and/or heparosan synthase-2 (pmHS2) from *Pasteurella multocida*. In some embodiments the elongation step comprises employing one or more monosaccharides selected from the group consisting of: glucuronic acid (GlcUA), N-acetylated glucosamine (GlcNAc), and N-trifluoroacetyl glucosamine (GlcNTFA). In some aspects the method of synthesizing the synthetic heparin analogue has a yield of greater than about 20% to about 50%.

Also provided herein are methods of treating a subject in need of anticoagulant therapy, the methods comprising providing a subject in need of anticoagulant therapy, administering to the subject a synthetic heparin analogue having anticoagulant activity, wherein the synthetic heparin analogue comprises at least one disaccharide unit sulfated by a 3-OST-3 enzyme, and at least one IdoA2S-GlcNS3S or IdoA2S-GlcNS3S6S disaccharide unit. In some embodiments such methods further comprise monitoring the subject for heparin-induced thrombocytopenia, and administering to the subject an antidote to reverse the anticoagulant activity of the synthetic heparin analogue if the subject suffers from heparin-induced thrombocytopenia. In some embodiments the antidote to reverse the anticoagulant activity of the synthetic heparin analogue is andexanet alfa. In some embodiments the subject is a human subject.

In such methods of treating a subject the synthetic heparin analogue can have a clearance rate about 50% to about 100% faster than that of other heparin compounds. The synthetic heparin analogue can comprise an anticoagulant activity of less than about 10% at 4 hours post-administration. In such methods the subject can have an elevated risk of bleeding.

Provided herein are pharmaceutical compositions comprising a synthetic heparin compound as disclosed herein.

The synthetic heparin analogues as disclosed herein, including methods of making and/or using the same, can comprise a structure, including for example:

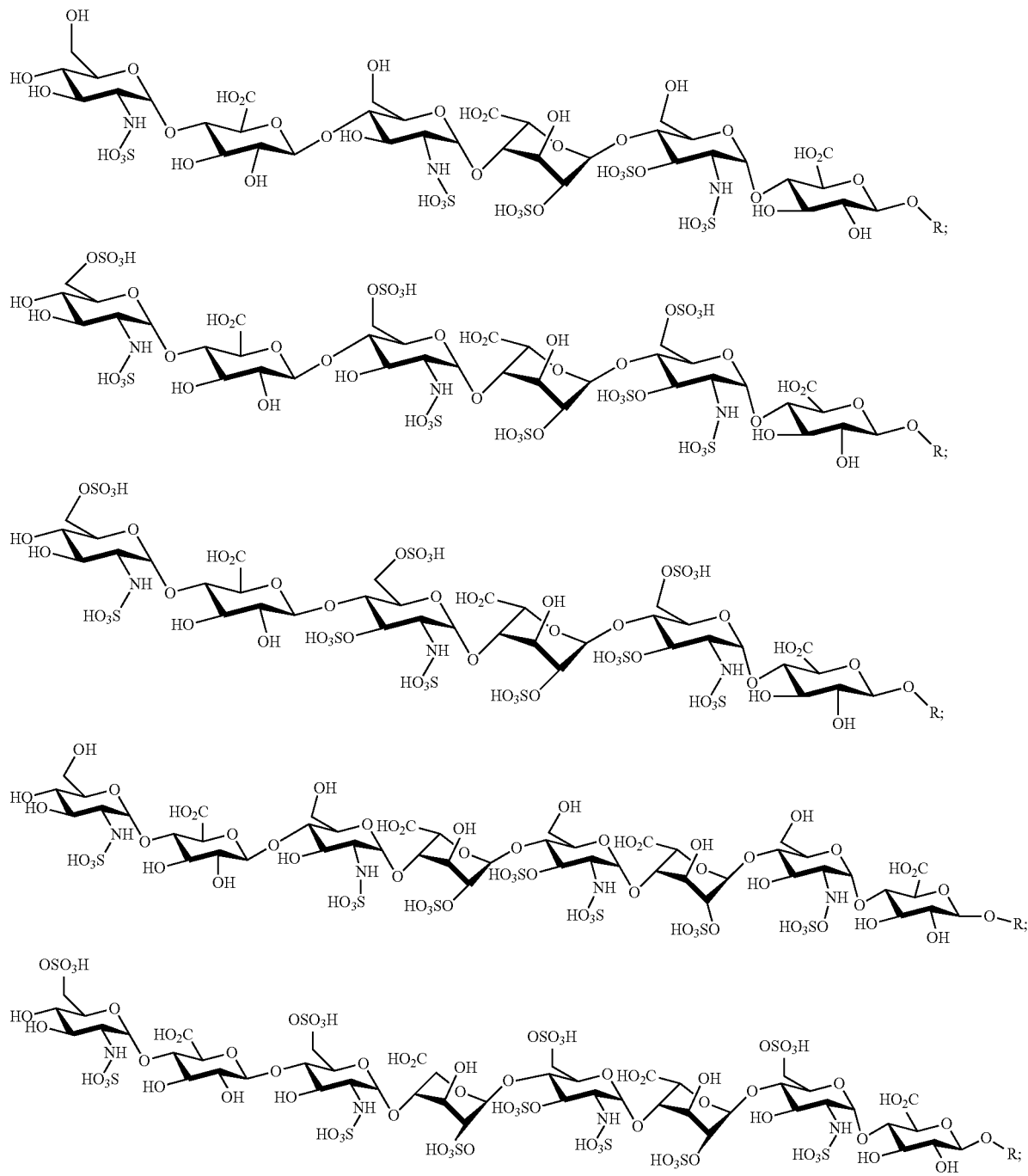

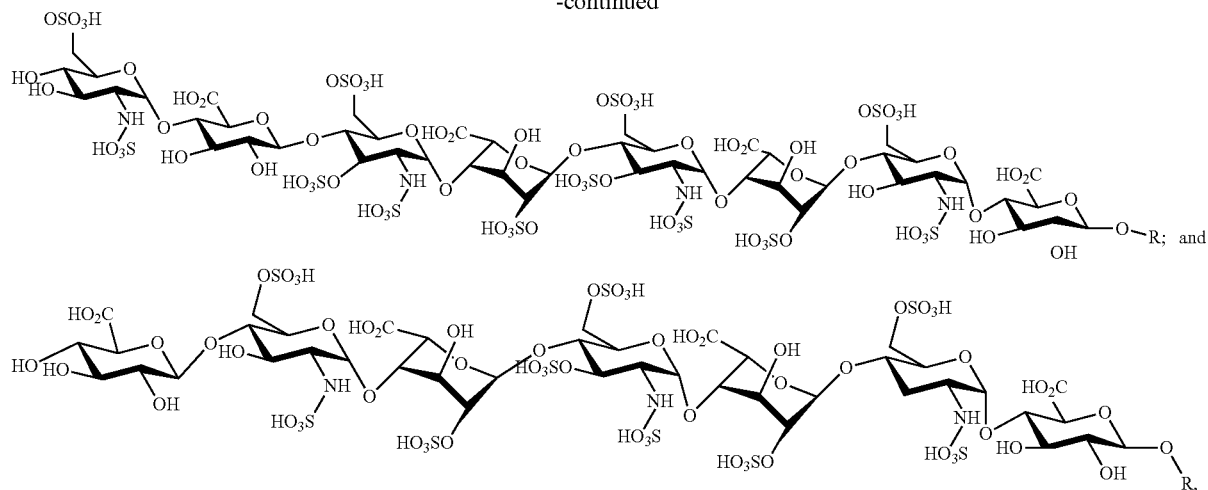

wherein R is selected from the group consisting of —H, alkyl (such as but not limited to —CH₃ or —CH₂CH₃), substituted alkyl, aryl, and substituted aryl (such as but not limited to a p-nitrophenyl group).

Accordingly, it is an object of the presently disclosed subject matter to provide short-acting heparin-based anticoagulant compounds and methods, including a new form of synthetic heparin.

This and other objects are achieved in whole or in part by the presently disclosed subject matter. Further, an object of the presently disclosed subject matter having been stated above, other objects and advantages of the presently disclosed subject matter will become apparent to those skilled in the art after a study of the following description, Drawings and Examples.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which:

FIGS. 1A through 1C illustrate the synthesis of hexasaccharides and octasaccharides disclosed and tested herein, including FIG. 1A which a schematic illustration of hexasaccharides and octasaccharides disclosed herein, FIG. 1B which is a schematic illustration of an exemplary method of synthesizing hexasaccharides and octasaccharides disclosed herein, and FIG. 1C illustrates chemical structures of pyranose rings of IdoA2S residues of hexasaccharides and octasaccharides disclosed herein;

FIGS. 5A and 5B are bar graphs showing the substrate requirements for 3-OST-1 and 3-OST-3, where FIG. 5C illustrates the chemical structures of the different sized oligosaccharides;

FIGS. 8A through 8C depict results of the analysis of a 7-mer HS compound disclosed herein, with FIG. 8A being a graphical summary of data showing the 7-mer has anti-Xa activity, FIG. 8B schematically comparing the chemical structural of the 7-mer to a 6-mer and 8-mer as disclosed herein, and FIG. 8C illustrating the synthetic pathway for synthesizing the 7-mer.

DETAILED DESCRIPTION

Figure 1B:
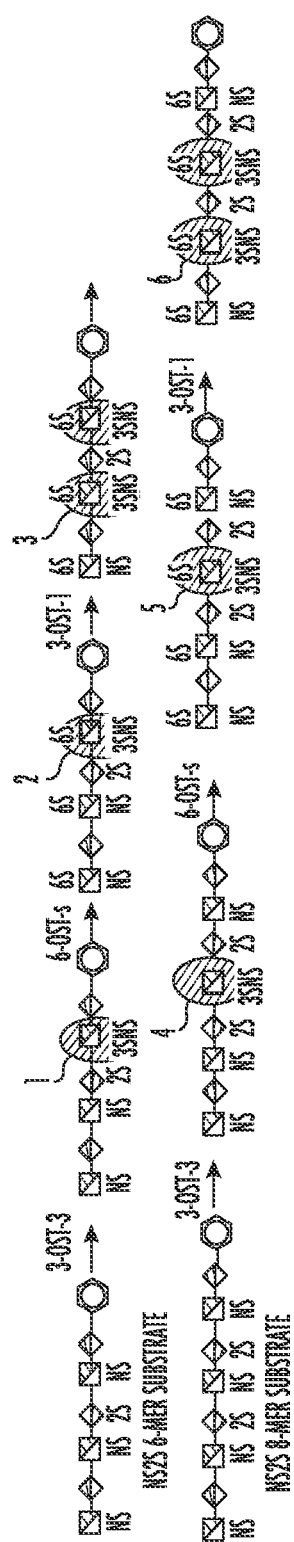

The presently disclosed subject matter now will be described more fully hereinafter, in which some, but not all embodiments of the presently disclosed subject matter are described. Indeed, the disclosed subject matter can be embodied in many different forms and should not be construed as limited to the embodiments set forth herein; rather, these embodiments are provided so that this disclosure will satisfy applicable legal requirements.

The sulfation at the 3-OH position of glucosamine is at least one important modification in forming structural domains for heparan sulfate to enable its biological functions. Seven 3-O-sulfotransferase isoforms in the human genome are involved in the biosynthesis of 3-O-sulfated heparan sulfate. As a rare modification present in heparan sulfate, the availability of 3-O-sulfated oligosaccharides is very limited. Disclosed herein is a novel chemoenzymatic synthetic approach to synthesize six 3-O-sulfated oligosaccharides, including three hexasaccharides and three octasaccharides. The synthesis was achieved by rearranging the enzymatic modification sequence to accommodate the substrate specificity of 3-O-sulfotransferase 3. The impact of 3-O-sulfation on the conformation of the pyranose ring of 2-O-sulfated iduronic acid using NMR, and on the correlation between ring conformation and anticoagulant activity, was studied. From this a novel octasaccharide that interacts with antithrombin and displays anti-factor Xa activity was discovered. Interestingly, the octasaccharide displays a faster clearance rate than fondaparinux, an approved pentasaccharide drug, in a rat model, making this octasaccharide a potential short-acting anticoagulant drug candidate that could reduce bleeding risk. The disclosed 3-O-sulfated oligosaccharides also provide for new heparan sulfate-based therapeutics.

Heparan sulfate (HS) is a polysaccharide comprising disaccharide repeating units of a glucuronic acid (GlcA) or iduronic acid (IdoA) residue linked to a glucosamine (GlcN) residue, with each capable of being modified by sulfation. HS exhibits important physiological and pathological functions, including regulating embryonic development, inflammatory responses, blood coagulation and viral/bacterial infections[1-3]. Most notably, heparin, a highly sulfated form of HS, is a widely used anticoagulant drug in clinics for the treatment of patients with thrombotic disorders[4].

The functional selectivity of HS and heparin can be governed, at least in part, by the sulfation types and the location of GlcA and IdoA residues. Sulfation is found at the 2-OH of IdoA (to a lesser extent GlcA) and the N—, 3-OH and 6-OH positions of GlcN residues. Moreover, the conformation of the IdoA and IdoA2S residues adopt both chair ($^1C4$) and skew boat ($^2SO$) conformations[6]. The conformations of GlcA, GlcA2S and GlcN residues exist in the chair ($^4C1$) conformation[7,8]. The conformational flexibility of IdoA2S residues can allow for binding to antithrombin to display anticoagulant activity[9] and fibroblast growth factors to regulate cell growth[10].

The synthesis of HS oligosaccharides remains a challenge. A number of oligosaccharides can be synthesized via a purely organic synthetic approach, but it is still very difficult to synthesize oligosaccharides larger than hexasaccharides with complex sulfation patterns. As an alternative approach, a chemoenzymatic method to synthesize HS oligosaccharides using HS biosynthetic enzymes involving glycosyltransferases, C5-epimerase, and sulfotransferases exists[16,17]. The method can offer high-efficiency synthesis for a wide range of oligosaccharide sequences; however, the synthesis of certain oligosaccharide sequences is not yet possible due to a lack of understanding of the substrate specificities of HS biosynthetic enzymes.

The 3-O-sulfation occurs infrequently in HS, but this sulfation type is believed to be intimately linked to its biological functions. The 3-O-sulfation can be important for anticoagulant activity[9], facilitates the entry of herpes simplex virus into host cells to establish infection[20], regulates axon guidance and growth of neurons[18] and controls the progenitor cell expansion for salivary gland development[3]. Precisely how the 3-O-sulfated glucosamine (GlcNS3S±6S) residues play roles in contributing to the biological activity of HS is currently unknown. The GlcNS3S±6S residue is shown to be surrounded by other monosaccharide residues to form a unique sulfated saccharide sequence domain, enabling HS to exert its biological effects. For example, the GlcNS3S±6S residue existing in a pentasaccharide domain enables HS to bind to antithrombin (AT). An octasaccharide carrying the GlcNS3S±6S residue interacts with herpes simplex virus glycoprotein D. Seven isoforms of 3-OST are present in the human genome that may potentially be used to prepare different 3-O-sulfated oligosaccharides[26].

Disclosed herein are schemes using the chemoenzymatic approach to prepare a 3-O-sulfated oligosaccharide library. It is demonstrated herein that the 3-OST-3 modification, to synthesize oligosaccharides comprising the -IdoA2S-GlcNS3S- or -IdoA2S-GlcNS3S6S- disaccharide unit, must precede the 6-O-sulfation step, whereas 3-OST-1 modification can occur only after 6-O-sulfation in order to generate the -GlcA-GlcNS3S6S- disaccharide unit. There were no interactions between 3-OST-3 and the 6-O-sulfo groups from the tetrasaccharide substrate, consistent with the conclusion that oligosaccharide substrates for 3-OST-3 do not require 6-O-sulfation. In contrast, interactions between 3-OST-1 and the 6-O-sulfo groups from the heptasaccharide substrate were observed, suggesting that 6-O-sulfation is required to bind to 3-OST-1. The distinct and unique substrate requirements between 3-OST-1 and 3-OST-3, as disclosed for the first time herein, reveal that 3-O-sulfated HS modified by different isoforms of 3-OST are biosynthesized through different pathways.

It was widely accepted that the 3-OST-1 enzyme is responsible for synthesizing anticoagulant HS, whereas the 3-OST-3 enzyme is not[34,35]. The AT-binding sequences isolated so far all comprise the -GlcA-GlcNS3S6S- disaccharide repeating unit, which is a product of 3-OST-1 enzyme modification[33,39]. This long-held belief is disputed by the instant disclosure, based on the discovery that oligosaccharides developed by the disclosed methods and are products of 3-OST-3 enzyme modification bind to AT and displays anticoagulant activity. These findings indicated that 3-OST-3 is capable of synthesizing anticoagulant HS, as long as the HS comprises the structural domain similar to that of compounds disclosed herein, including for example but not limited to compound 5.

Also disclosed herein is the discovery that some of the develop HS compounds, or oligosaccharides, have an unexpectedly fast clearance. The fast clearance of such compounds offers a potential new short-acting anticoagulant drug candidate with reduced bleeding risk. A short-acting anticoagulant drug, which can be cleared from the circulation quickly before major bleeding effects developed, would be particularly beneficial to those patients with high bleeding risk, or an elevated risk of bleeding as compared to a normal or healthy patient/subject. Although unfractionated heparin is an anticoagulant with a short half-life, the concern is that the drug causes heparin-induced thrombocytopenia (HIT), a life-threatening side effect[42]. It has been found that short oligosaccharides smaller than 12-mers[43] do not bind to platelet factor 4, and thus display no risk of HIT. As hexasaccharides and octasaccharide, the compounds disclosed herein, including for example compound 5, are expected to have very low risk of HIT.

A HS compound, or synthetic heparin analogue, as disclosed herein can in some embodiments comprise a 3-O-sulfated oligosaccharide comprising six to eight disaccharide units, at least one disaccharide unit is sulfated by a 3-OST-3 enzyme, and at least one IdoA2S-GlcNS3S or IdoA2S-GlcNS3S6S disaccharide unit. As illustrated in the working examples herein, such a synthetic heparin analogue has anticoagulant activity, including a binding affinity to antithrombin ranging from about 5 nM to about 30 nM and anti-Xa activity ranging from about 10 ngml$^{-1}$ to about 40 ngml$^{-1}$ IC$_{50}$. The structure or makeup of such synthetic heparin analogues is exemplified by compounds 1 to 11, and particularly 1-6, including in FIGS. 6A through 6F.

As discussed further herein, in some embodiments the synthetic heparin analogues can have an unexpectedly rapid clearance rate, particularly as compared to heparin and heparin-like compounds. For example, the clearance rate of compound 5 is at least about 50%, 75% or 100% faster than that of fondaparinux in a rat or mouse model, or about 50% to about 100%, about 60% to about 90%, about 70% to about 80%, about 50% to about 75%, or about 75% to about 100%. Such rapid clearance can make such compounds suitable as short-acting anticoagulant compounds, which can be particularly suitable for applications and/or subjects at higher risk of bleeding. Such compounds are also shown not to cause heparin-induced thrombocytopenia (HIT).

Methods of synthesizing the synthetic heparin analogues are illustrated (see, e.g. FIGS. 1A, 1B and 8C) and discussed further herein, but can in some aspects include providing a saccharide substrate, elongating the saccharide substrate to a saccharide of a desired or predetermined length, performing at least one sulfation reaction using a 3-OST-3 isoform of a 3-O-sulfotransferase (3-OST) enzyme, whereby a synthetic heparin analogue is synthesized. The saccharide substrate may comprise at least one IdoA2S-GlcNS3S disaccharide unit.

The disclosed methods of synthesizing the synthetic heparin analogues can provide surprisingly high yields of the heparin compounds. By way of example and not limitation, the disclosed methods of synthesizing the synthetic heparin analogues can have yields of greater than about 20%, greater than about 30%, greater than about 40%, greater than about 50%, about 20% to about 50%, about 30% to about 50%, or about 40% to about 50%.

Where the saccharide substrate comprises a IdoA2S-GlcNS3S±6S disaccharide unit, such a method can further comprise a 6-O-sulfation step using a 6-O-sulfotransferase (6-OST), wherein a 3-O-sulfation by 3-OST-3 occurs prior to the 6-O-sulfation step. In contrast, where the saccharide substrate comprises a GlcA-GlcNS3S6S disaccharide unit, such a method can further comprise a 6-O-sulfation step using a 6-O-sulfotransferase (6-OST), wherein a 3-O-sulfation by 3-OST-1 occurs prior to the 6-O-sulfation step.

The development of the presently disclosed heparin compounds and synthetic heparin analogues also provides for treatments and methods of treating subjects using the same. For example, in some embodiments methods of treating subjects in need of anticoagulant therapy are provided. Such methods can comprise providing a subject in need of anticoagulant therapy and administering to the subject a synthetic heparin analogue having anticoagulant activity, wherein the synthetic heparin analogue comprises at least one disaccharide unit sulfated by a 3-OST-3 enzyme, and at least one IdoA2S-GlcNS3S or IdoA2S-GlcNS3S6S disaccharide unit. Where needed the subject can also be monitored for heparin-induced thrombocytopenia, and if detected the subject can be administered an antidote to reverse the anticoagulant activity of the synthetic heparin analogue if the subject suffers from heparin-induced thrombocytopenia. Such reversal of anticoagulant activity can be achieved, for example, by andexanet alfa (AndexXa®, Portola Pharmaceuticals, South San Francisco, Calif., United States of America) at a rate of 50% or more in the presence of 20 ug/ml or less of andexanet alfa.

Thus, in accordance with some embodiments of the presently disclosed subject matter, provided is a method of treating a subject in need of anticoagulant therapy. In some embodiments, the method comprises: providing a subject in need of anticoagulant therapy; administering to the subject a synthetic heparin analogue having anticoagulant activity, wherein the synthetic heparin analogue comprises at least one disaccharide unit sulfated by a 3-OST-3 enzyme, and at least one IdoA2S-GlcNS3S or IdoA2S-GlcNS3S6S disaccharide unit.

In some embodiments, the presently disclosed subject matter provides a synthetic heparin analogue having anticoagulant activity, wherein the synthetic heparin analogue comprises at least one disaccharide unit sulfated by a 3-OST-3 enzyme, and at least one IdoA2S-GlcNS3S or IdoA2S-GlcNS3S6S disaccharide unit, for use in treating and/or preventing a disease or disorder wherein anticoagulant activity is advantageous. By way of example and not limitation, such diseases or disorders can include patients and individuals, including cancer patients, with high risk of deep vein thrombosis.

In yet another embodiment, the present disclosure provides the use of a synthetic heparin analogue having anticoagulant activity, wherein the synthetic heparin analogue comprises at least one disaccharide unit sulfated by a 3-OST-3 enzyme, and at least one IdoA2S-GlcNS3S or IdoA2S-GlcNS3S6S disaccharide unit, for the preparation of a pharmaceutical composition for in treating and/or preventing a disease or disorder wherein anticoagulant activity is advantageous.

Example synthetic heparin analogues, or HS compounds, are disclosed herein, including for example in FIGS. 1A and 6A through 6F. In the structures shown "R" can comprise a proton (—H), —CH$_3$, —CH$_2$CH$_3$, or other substituted group similar to p-nitrophenyl. Such groups can also comprise, and/or be referred to as alkyl or lower alkyl. Other substituted groups similar to p-nitrophenyl can in some embodiments comprise aryl or substituted aryl. Alternatively or in addition, in some embodiments "R" can comprise a detectable tag or detectable moiety.

Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, dose, sequence identity (e.g., when comparing two or more nucleotide or amino acid sequences), mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

A structure represented generally by a formula such as:

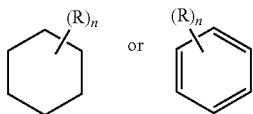

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure:

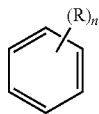

wherein n is an integer from 0 to 2 comprises compound groups including, but not limited to:

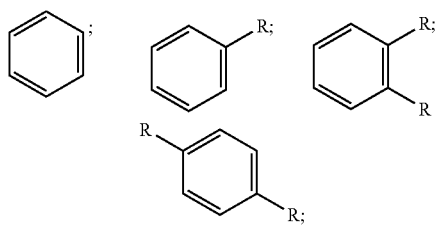

and the like.

"Cyclic" and "cycloalkyl" refer to a non-aromatic mono- or multicyclic ring system of about 3 to about 10 carbon atoms, e.g., 3, 4, 5, 6, 7, 8, 9, or carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "heterocycle" refers to a non-aromatic or aromatic, monocyclic or multicyclic ring system of about 3 to about 14 atoms, wherein at least one of the atoms is a heteroatom (e.g., oxygen, nitrogen, or sulfur). The term "N-heterocycle" refers to a heterocycle wherein at least one of the heteroatoms is a nitrogen atom. Examples of N-heterocycles include, but are not limited to, azetidine, pyrrolidine, pyrrole, pyrroline, piperidine, pyridine, piperazine, pyrazine, pyrimidine, pyridazine, morpholine, and thiazine.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

As used herein, the term "acyl" refers to an organic carboxylic acid group wherein the —OH of the carboxyl group has been replaced with another substituent (i.e., as represented by RC(═O)—, wherein R is an alkyl, substituted alkyl, aralkyl, aryl or substituted aryl group as defined herein). As such, the term "acyl" specifically includes arylacyl groups, such as an acetylfuran and a phenacyl group. Specific examples of acyl groups include acetyl and benzoyl.

"N-acyl" refers to a group having the structure —N—C(═O)—R, wherein R is as defined for acyl. These groups can also be referred to as amides. Modified N-acyl groups include compounds wherein the oxygen of the N-acyl has been replaced by S or NH, as well as to compounds wherein the carbonyl group (i.e., the —C(═O)—) is attached to a second heteroatom in addition to the nitrogen. For example, the carbonyl can be attached to a second nitrogen atom to form a urea linkage (i.e., —NH—C(═O)—NH—R).

The term "amino" refers to the —NH$_2$, the —NHR, and the —NR$_2$ groups, wherein each R is independently alkyl, substituted alkyl, aryl, substituted aryl, or aralkyl, as well as to amino and ammonium functionalities in N-heterocycles (e.g., morpholine, etc). As used herein the term "amino" can also refer to substituents that provide quaternary ammonium cations, such as —$^+$NH$_3$, —$^+$NH(R)$_2$, and —$^+$N(R)$_3$ groups, wherein each R is independently alkyl, substituted alkyl, aryl, substituted aryl or aralkyl.

The term "ester" refers to a moiety comprising an —O—C(═O)—R group, wherein R can be alkyl, substituted alkyl, aralkyl, aryl, or substituted aryl. In some embodiments, the R group can include an amino substituent and the ester is an amino ester.

The term "amide" refers to a moiety comprising a —N(R')—C(═O)—R group, wherein R is selected from alkyl, substituted alkyl, aralkyl, aryl or substituted aryl and R' is H, alkyl, substituted alkyl, aralkyl, aryl, or substituted aryl.

The term "urea" as used herein can refer to a moiety comprising a —N(R')—C(═O)—N(R')— group, wherein each R' is independently H, alkyl, substituted alkyl, aralkyl, aryl, or substituted aryl.

The term "hydroxyl" refers to the —OH group.

When the term "independently selected" is used, the substituents being referred to (e.g., R groups, such as groups R$_1$ and R$_2$, or groups X and Y), can be identical or different. For example, both R$_1$ and R$_2$ can be substituted alkyls, or R$_1$ can be hydrogen and R$_2$ can be a substituted alkyl, and the like.

Subjects

The subject treated, screened, tested, or from which a sample is taken, is desirably a human subject, although it is to be understood that the principles of the disclosed subject matter indicate that the compositions and methods are effective with respect to invertebrate and to all vertebrate species, including mammals, which are intended to be included in the term "subject". Moreover, a mammal is understood to include any mammalian species in which screening is desirable, particularly agricultural and domestic mammalian species.

The disclosed methods, compounds and treatments are particularly useful in the testing, screening and/or treatment of warm-blooded vertebrates. Thus, the presently disclosed subject matter concerns mammals and birds.

More particularly, provided herein is the testing, screening and/or treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, provided herein is the treatment of livestock, including, but not limited to, domesticated swine (pigs and hogs), ruminants, horses, poultry, and the like.

In some embodiments, the subject to be used in accordance with the presently disclosed subject matter is a subject in need of treatment and/or diagnosis. In some embodiments, a subject can be in need of anticoagulant therapy or related condition or phenotype. In some embodiments, the subject in need of anticoagulant therapy can be a subject with a high risk of bleeding.

Formulations

The compositions of the presently disclosed subject matter comprise in some embodiments a composition that includes a pharmaceutically acceptable carrier. Any suitable pharmaceutical formulation can be used to prepare the adenovirus vectors for administration to a subject.

For example, suitable formulations can include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS, mannitol or another sugar, and phosphate-buffered saline (PBS).

It should be understood that in addition to the ingredients particularly mentioned above the formulations of this presently disclosed subject matter can include other agents conventional in the art having regard to the type of formulation in question. For example, sterile pyrogen-free aqueous and non-aqueous solutions can be used.

Administration

Administration of the compositions of the presently disclosed subject matter can be by any method known to one of ordinary skill in the art, including, but not limited to intravenous administration, intrasynovial administration, transdermal administration, intramuscular administration, subcutaneous administration, topical administration, rectal administration, intravaginal administration, intratumoral administration, oral administration, buccal administration, nasal administration, parenteral administration, inhalation, and insufflation. In some embodiments, suitable methods for administration of a composition of the presently disclosed subject matter include, but are not limited to intravenous. Alternatively, a composition can be deposited at a site in need of treatment in any other manner. The particular mode of administering a composition of the presently disclosed subject matter depends on various factors.

Dosage

An effective dose of a composition of the presently disclosed subject matter is administered to a subject in need thereof. A "therapeutically effective amount" is an amount of the composition sufficient to produce a measurable response (e.g., anticoagulation). In some embodiments, a therapeutically effective amount is an amount sufficient to prevent coagulation, i.e. anticoagulation. In some embodiments, a therapeutically effective amount is an amount sufficient to improve the health, well-being, prognosis and/or survivability of a subject requiring anticoagulant therapy.

Actual dosage levels of active ingredients in the compositions of the presently disclosed subject matter can be varied so as to administer an amount of the active compound(s) that is effective to achieve the desired therapeutic response for a particular subject. The selected dosage level can depend upon the activity of the therapeutic composition, the route of administration, combination with other drugs or treatments, the severity of the condition being treated, and the condition and prior medical history of the subject being treated. However, it is within the skill of the art to start doses of the compositions at levels lower than required to achieve the desired therapeutic effect and to gradually increase the dosage until the desired effect is achieved.

After review of the disclosure of the presently disclosed subject matter presented herein, one of ordinary skill in the art can tailor the dosages to an individual patient, taking into account the particular formulation, method for administration to be used with the composition, and severity of the condition. Further calculations of dose can consider patient height and weight, severity and stage of symptoms, and the presence of additional deleterious physical conditions. Such adjustments or variations, as well as evaluation of when and how to make such adjustments or variations, are well known to those of ordinary skill in the art of medicine.

EXAMPLES

The following Examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Materials and Methods

Expression and Purification of Enzymes

The expression of 6-O-sulfotransferase 1 (6-OST-1) and 6-O-sulfotransferase 3 (6-OST-3) was carried out in the Sf9 cells (Invitrogen) using Sf-900™ III SFM (Life Technologies). Insect cells at a concentration of $2.0 \times 10^6$ cells/mL were infected by the recombinant virus expressing mouse 6-OST-1 and human 6-OST-3 and were allowed to incubate in the shaker at 27° C. for 96 h. The culture solution was centrifuged at 4,000 RPM for 10 min to pellet the cells. The supernatant containing 1 mM phenylmethanesulfonyl fluoride (PMSF, a 100 mM stock solution was freshly made in 95% ethanol), 0.05% Triton X-100 and 0.2% glycerol was then centrifuged at 8000 RPM for 30 min and filtered through a 1.5 µm membrane. The resultant medium was then mixed with an equal volume of 40 mM 3-(N-morpholino) propanesulfonic acid (MOPS) buffer containing 0.05% Triton-100 and 2% Glycerol, pH 7.0). Heparin Toyopearl gel (Tosoh Bioscience) column was used to purify the 6-OST-1 and 3 with two buffers: buffer A contained 20 mM MOPS, pH 7.0, 100 mM NaCl, 2% glycerol and 0.1% reduced triton X-100 (Sigma); and buffer B contained 20 mM MOPS, pH 7.0, 1 M NaCl, 2% glycerol and 0.1% reduced triton X-100. After loading the medium, buffer A was used to wash the column until UV absorbance at 280 nm reached baseline at a flow rate of 4 mL/min. A gradient elution of 0-100% B in 60 min was applied, and the column was eluted with additional 60 min with 100% B at a flow rate of 1.5 mL/min. The purification of enzyme was performed at 4° C.

The expression of 3-OST-1 and 3-OST-3 was performed in *Escherichia coli* using BL21 cells. The transformed cells were grown in LB medium containing 50 µg/L kanamycin for 3-OST-1 and 3-OST-3 and incubated at 37° C. until the OD600 reached 0.6-0.8. Isopropylthiogalactopyranoside (IPTG) at a final concentration of 0.2 mM was added to induce the expression of 3-OST-1 and 3. The bacteria culture was kept shaking at 22° C. overnight. The bacterial cells were harvested by spinning at 3400 RPM for 15 min. The cells were resuspended in 25 mL of buffer solution containing 25 mM Tris, pH 7.5, 30 mM imidazole, and 500 mM NaCl. The suspension was sonicated and centrifuged at 14,000 RPM for 30 min. The supernatant was filtered through a 0.45 µm membrane before purification. Nickel-agarose (GE Healthcare) column was used to purify the proteins with two buffers: buffer C contained 25 mM Tris, pH 7.5, 30 mM imidazole, and 500 mM NaCl; buffer D contained 25 mM Tris, pH 7.5, 300 mM imidazole, and 500 mM NaCl. After loading the medium, buffer C was used to wash the column until UV absorbance at 280 nm reached baseline at a flow fate of 2 mL/min. Buffer D was then applied to elute the protein.

Chemoenzymatic Synthesis of Oligosaccharides (Compounds 1 to 6)

The synthesis of compound 1 to 3 was initiated from a hexasaccharide (GlcNS-GlcA-GlcNS-IdoA2S-GlcNS-GlcA-pNP), designated as "NS2S 6-mer substrate". To synthesize compound 1, the substrate (25 mg) was incubated with 1.8 mM 3'-phosphoadenosine 5'-phosphosulfate (PAPS) in a buffer containing 50 mM MOPS (pH 7.0), 10 mM MnCl2, 7 mM MgCl2, and 2 mL 3-OST-3 (0.11 mg/mL) in a total volume of 100 mL. The reaction mixture was incubated at 37° C. overnight. The completion of the reaction was monitored by injecting a small amount of reaction mixture to anion exchange HPLC (TSKgel DNA-NPR-column (4.6 mm×7.5 cm, 2.5 µm, from Tosoh Bioscience)). If reaction was <60% complete, additional 3-OST-3 enzyme and PAPS were added, and the reaction mixture was kept at 37° C. for another 18-24 hours. If the reaction was completed, the reaction mixture was subjected to Q-Sepharose chromatography (GE Healthcare).

To synthesize compound 2, compound 1 (5 mg) was incubated with 6-OST-1, 6-OST-3 enzymes and 1.3 mM PAPS in a buffer containing 100 mM MOPS (pH 7.0), and 1 mL enzyme cocktails of 6-OST-1 and 3 in a total volume of 100 mL at 37° C. overnight. The completion of the reaction was monitored by injecting a small amount of reaction mixture to anion exchange HPLC, and the product was purified by Q-Sepharose. To synthesize compound 3, compound 2 (4 mg) was incubated with 1.3 mM PAPS in a buffer containing 18 mM MOPS (pH 7.0), 5 mM MnCl2, 5 mM MgCl2, and 6 mL 3-OST-1 (4 µg/mL) in a total volume of 100 mL. The reaction mixture was incubated at 37° C. overnight. The completion of the reaction was monitored by injecting a small amount of reaction mixture to anion exchange HPLC, and the product was purified by Q-Sepharose.

The synthesis of compound 4 to 6, an octasaccharide (GlcNS-GlcA-GlcNS-IdoA2S-GlcNS-IdoA2S-GlcNS-GlcA-pNP), designated as NS2S 8-mer substrate, was used as the starting material. To synthesize compound 4, 30 mg of the substrate was incubated with 2 mM PAPS in a buffer containing 33 mM MOPS (pH 7.0), 10 mM MnCl2, 5 mM MgCl2, and 4 mL 3-OST-3 (0.11 mg/mL) in a total volume of 90 mL. The reaction mixture was incubated at 37° C. overnight. The completion of the reaction was monitored by injecting a small amount of the reaction mixture to anion exchange HPLC. If reaction was <60% complete, additional 3-OST-3 enzyme and PAPS were added, and the reaction mixture was kept at 37° C. for another 18-24 hours. If the reaction was completed, the reaction mixture was subjected to Q-Sepharose chromatography (GE Healthcare).

To synthesis of compound 5, compound 4 (22 mg) was incubated with 6-OST-1, 6-OST-3 enzymes and 0.8 mM PAPS in a buffer containing 100 mM MOPS (pH 7.0), and 3 mL a mixture of 6-OST-1 and 3 in a total volume of 100 mL at 37° C. overnight. The completion of the reaction was monitored by injecting a small amount of reaction mixture to anion exchange HPLC, and the product was purified by Q-Sepharose. To synthesize compound 6, compound 5 (6.5 mg) was incubated with 1.3 mM PAPS in a buffer containing 18 mM MOPS (pH 7.0), 5 mM MnCl2, 5 mM MgCl2, and 4.5 mL 3-OST-1 in a total volume of 100 mL (4 µg/mL). The reaction mixture was incubated at 37° C. overnight. The completion of the reaction was monitored by injecting a small amount of reaction mixture to anion exchange HPLC, and the product was purified by Q-Sepharose.

Substrate Specificities of 3-OST-1 and 3-OST-3

To determine the substrate requirements for 3-OST-1 and 3-OST-3, different sizes of structurally homogeneous oligosaccharides were used. These oligosaccharides included N-sulfated and 2-O-sulfated 6-mers to 12-mers (6-mer2S to 12-mer2S) and N-sulfated, 2-O-sulfated and 6-O-sulfated 6-mers to 12-mers (6-mer2S6S to 12-mer2S6S). These oligosaccharides were prepared by the chemoenzymatic method 1, and their structures are displayed in FIG. 5C. Oligosaccharides (0.033 mM) were incubated in the 100 µL reaction buffer containing 50 mM MOPs (pH 7.0), 10 mM MnCl2, 5 mM MgCl2, 2.5 µL 3-OST-1 or 3-OST-3, and 30 µM of PAPS mixed with [35S] PAPS ($1\text{-}3\times10^5$ cpm) at 37° C. for 1 h. To the reaction mixture, 900 µL 3 M urea containing 1.4 mM EDTA, 50 mM sodium acetate and 150 mM NaCl was added to quench the reaction. The reaction mixture was then purified using the DEAE-column.

Kinetic Analysis of 3-OST-3 Towards Different Oligosaccharide Substrates

The enzyme kinetic was characterized by incubating the mixture of 30 µL of purified 3-OST-3 for oligosaccharides with N-sulfation and 2-O-sulfation or 60 µL of purified 3-OST-3 for oligosaccharides with N-sulfation, 2-O-sulfation and 6-O-sulfation. PAPS (120 µM) was mixed with $1\times10^5$ cpm of [35S] PAPS as sulfate donor and oligosaccharides at various concentrations from 0-200 µM at 37° C.

for 1 h. The reaction was loaded on a DEAE column to purify the 35S-labeled oligosaccharide product. The amount of 35S-labeled oligosaccharide products were plotted against concentrations of substrate followed by curve-fitting for Michalis-Menten graph using Sigma Plot software to obtain Km and Vmax values.

Purification of Compound 1 to 6 by Q-Sepharose

The purification of sulfated oligosaccharide was performed with Q-Sepharose column. Mobile phase A was 25 mM Tris, pH 7.5. Mobile phase B contained 25 mM Tris and 1 M NaCl, pH 7.5. The elution gradient was based on the sulfate group numbers of synthesized oligosaccharides with a flow rate of 1 mL/min. The absorption at 310 nm and 260 nm was scanned and recorded. After purification, the sample was dialyzed twice using 1000 MWCO membrane against a buffer containing 5 mM sodium phosphate dibasic (pH 7.5).

HPLC Analysis of Synthesized Oligosaccharides

TSKgel DNA-NPR-column was applied to detect the degree of completion of the reaction and the purity of synthesized oligosaccharide after purification. Mobile phase A was 25 mM Tris, pH 7.5. Mobile phase B was 25 mM Tris and 1 M NaCl, pH 7.5. The gradient step was 0-100% B in 100 min with a flow rate of 0.4 mL/min. The absorption at 310 nm and 260 nm was used to monitor the eluent.

ESI-MS Analysis of Oligosaccharides

Molecular weight conformation of synthesized oligosaccharides was determined by the ESI-MS (Thermo LCQ-Deca). ESI-MS analysis was performed in the negative ion mode and with the following parameters: 1 Spray voltage at 3.0 kV, curved desolvation line temperature at 120° C. The mass range was set at 300-1000.

Preparation of 3-O-[34S]Sulfated Compound 3

To synthesize 3-O-[34S] sulfated compound 4, the substrate NS2S 8-mer (2 mg) was incubated with 3-OST-3 enzyme (0.11 mg/mL) and 0.1 mM [34S]PAPS in a buffer containing 38 mM MOPS (pH 7.0), 10 mM MnCl2, 5 mM MgCl2, and 6 mL 3-OST-3 in a total volume of 20 mL. The reaction mixture was incubated at 37° C. overnight. The purification of product was performed with Q-Sepharose column.

Tandem MS Analysis of 3-OST-3 Modified Octasaccharide

The tandem mass spectra analysis was acquired on a Thermo LTQ-FT instrument in negative ion mode with the following instrument parameters: I spray voltage (kV), −3.5 kV; capillary voltage (kV), −40 kV; tube lens (V), −50 V and capillary temperature at 275° C. For the tandem mass, the selected precursor ions were performed with the following parameters: Iso Width (m/z): 3.0, Normalized Collision Energy (%): 50.0, Act. Q: 0.250, Act. Time: 30, Max. Inject Time (ms): 500.000. The MS and MS/MS data were recorded and processed by using Xcalibur 2.2 software.

Structural Analysis of Compound 1 to 6 by NMR

NMR experiments were performed at 298 K on Bruker Avance 700 MHz and 850 MHz spectrometer with Topsin 3.2 software. Samples (0.5 to 3.0 mg) were each dissolved in 0.5 ml $D_2O$ (99.996%, Sigma-Aldrich) and lyophilized three times to remove the exchangeable protons. The samples were re-dissolved in 0.5 ml $D_2O$ and transferred to NMR microtubes (O.D. 5 mm, Norrell). Chemical shifts are referenced to external 2,2-dimethyl-2-silapentane-5-sulfonate sodium salt (DSS, Sigma, Co.). Deuterated EDTA (Sigma, Co.) was added to remove the effect of paramagnetic ions. 1D 1H-NMR experiments "zg" pulse sequence were performed with 64 scans and an acquisition time of 3.8 sec. 1D 13C-NMR experiments "zgdc30" pulse sequence were performed with 10,000 scans and an acquisition time of 1.0 sec. 2D 1H-13C HSQC experiments "hsqcgpph" pulse sequence were performed with 48 scans, 512 increments, 1.5 sec relaxation delay, and 120 msec acquisition time. 2D spectra were recorded with GARP carbon decoupling. 48 dummy scans were used prior to the start of acquisition. 2048 total points were collected in f2. $^{13}C$ transmitter offset was set at 90.0 ppm.

Molecular Dynamics Pre-Processing

An existing crystal structure of the AT-pentasaccharide complex (PDB ID: 3EVJ) was employed as a starting structure of the system[47]. Amino acid residues 25-33 and 396 were not resolved in the crystal structure, so were generated with the Chimera interface to Modeller[48-51]. The N-glycans were removed, as they are distal (>15 Å) from the fondaparinux ligand. The original ligand was modified for the various simulations with tleap and manually adjusted with Chimera. Parameters for the amino acids and carbohydrate residues were obtained from the ff14SB7 and GLYCAM06 (J-1) force fields[53,54]. The system was neutralized with Na+ ions, and solvated with the TIP3P water model in a truncated octahedral box 12 Å around the complex.

Molecular Dynamics Protocol

Figure 4A:
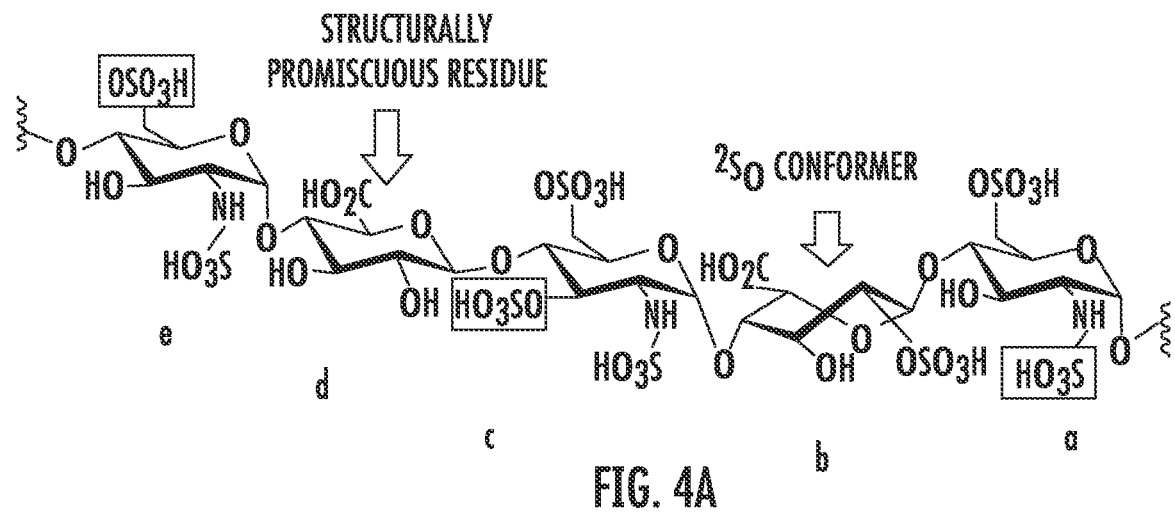
FIG. 4A schematic of the chemical structure of the AT-binding site with FIG. 4B graphically depicting results of molecular dynamics (MD) simulations of AT in complex.

Energy minimizations and MD simulations were performed using the pmemd.cuda module from AMBER14[52]. The Cα atoms of the protein backbone were restricted with cartesian restraints (10 kcal/mol Å²) throughout every step of the process. Two of the simulations required internal restraints on IdoA2S residue d (FIG. 4A) to maintain a $^1C_4$ or $2S_O$ conformation, and were implemented according to settings described previously[55]. The systems were minimized using the steepest descent method for the initial 1000 cycles before switching to conjugate gradient for the remaining 24,000 cycles. To aid in generating a stable configuration for the AT-oligosaccharide complexes, two minimizations were performed with varying atomic restraints. Initially, every solute atom was restrained. Subsequently, the restraints on the ligand and side chains of the protein were removed. Electrostatic interactions were treated with the Particle-Mesh Ewald algorithm[56] and an 8 Å cutoff for non-bonded interactions was employed. The SHAKE algorithm was applied to hydrogen-containing bonds, enabling an integration time step of 2 fs. The system was heated to 300 K under NVT conditions over 60 ps by employing the Berendsen thermostat with a coupling time constant of 1 ps, and allowed to equilibrate for a total of 50 ns under NPT conditions. Post-equilibration data sets were collected for an additional 150 ns, also under NPT conditions.

Simulation Data Analysis

Interaction energies were calculated with the single-trajectory Molecular Mechanics-Generalized Born Solvent Accessible Surface Area (MM-GBSA) method[57] using the MPBSA.py.MPI module[52]. Before the analyses, all water molecules and ions were removed from each complex, and the contribution from desolvation energy approximated through the GB implicit solvation model (igb=2)[58]. The simulation was divided into 5 ns bins and average interaction energy contributions computed from an ensemble of 100 snapshots evenly distributed within each bin. Statistical analysis was performed with GraphPad Prism for Windows version 5.04. Significance was determined based upon a p-value≤0.0001 according to t-test analysis. Images were created with the Visual Molecular Dynamics program[59].

Determination of Anti-FXa Activity In Vitro

Factor Xa (Enzyme Research Laboratories, South Bend, Ind.) was diluted to 60 nM with PBS containing 1 mg/mL bovine serum albumin (BSA). Human antithrombin (AT) (from Cutter Biological) was prepared in PBS containing 1 mg/mL BSA at a concentration of 0.65 µM. The chromogenic substrate S-2765 (Diapharma) was dissolved in water to make a 1 mg/mL stock solution. The oligosaccharides were made up of different concentration (10-200 nM) with PBS. The solution was a mixture of 60 µL of AT and 15 µL sample solution, which was vortexed and incubated at room temperature for 2 min. Factor Xa (90 µL) was then added and incubated at room temperature for 4 min, following which 30 µL S-2765 was added. The reaction mixture was measured based on their absorbance at 405 nm continuously for 2 min. The calculation of $IC_{50}$ values was plotted as a function of sample concentrations versus the initial reaction rates.

Determination of Anti-FXa Effect In Vivo

All studies were performed under an Institutional Animal Care and Use Committee (IACUC)-approved protocol at the University of North Carolina, following Public Health Service guidelines for laboratory animal care and use. Sixteen 400-g Lewis rats were equally divided into four groups. Each group was intravenously administered with either endotoxin-free fondaparinux (0.46 µM kg-1), compound 11 (0.43 µM kg$^{-1}$), compound 5 (0.42 µM kg$^{-1}$) or saline. Blood was then drawn at specified time points (0.5, 1, 2, 4, 8 hours) after the compounds had been administered, with one sample taken just before administration. 0.8 mL of blood was drawn from the contralateral femoral/saphenous vein into 150 mM citrate at 0.5, 1, 2, 4 and 8 hours following injection of the compounds, with one sample drawn immediately prior to injection. The samples were centrifuged to obtain approximately 400 µL of plasma. The blood samples were subjected to FXa activity analysis. Saline was given periodically subcutaneously to maintain fluid volume.

Determination of the Clearance of Oligosaccharides from the Drug-Treated Animals Using a calibration curve generated for each compound, the concentration of compound in the reaction mixture was read off for each corresponding FXa activity percentage. The average plasma concentration and standard deviation between the 4 rats in each group were calculated for each time point; these values were used to plot a graph of plasma concentration against time.

Example 1

Chemoenzymatic Synthesis of Oligosaccharides Carrying GlcNS3S and GlcNS3S6S Residues The synthesis of hexasaccharides (compound 1 to 3, FIG. 1A) and octasaccharides (compound 4 to 6, FIG. 1A) was accomplished in the current study. Two 3-O-sulfotransferase (3-OST) isoforms, 3-OST-1 and 3-OST-3, were employed to install the GlcNS3S±6S residue into different saccharide sequences. The 3-OST-1 enzyme introduces a sulfation to form a GlcNS3S6S residue that is linked to a GlcA residue at the nonreducing end, forming the disaccharide unit of -GlcA-GlcNS3S6S-; whereas the 3-OST-3 enzyme introduces a sulfation to form a GlcNS3S residue that is linked to an IdoA2S residue at the nonreducing end, forming the disaccharide unit of -IdoA2S-GlcNS3S-. Although 3-OST-1 has been successfully used to synthesize oligosaccharides in numerous studies[16,17,27,28], the use of 3-OST-3 to synthesize oligosaccharides comprising the -IdoA2S-GlcNS3S- disaccharide units has not been reported.

Figure 5A:
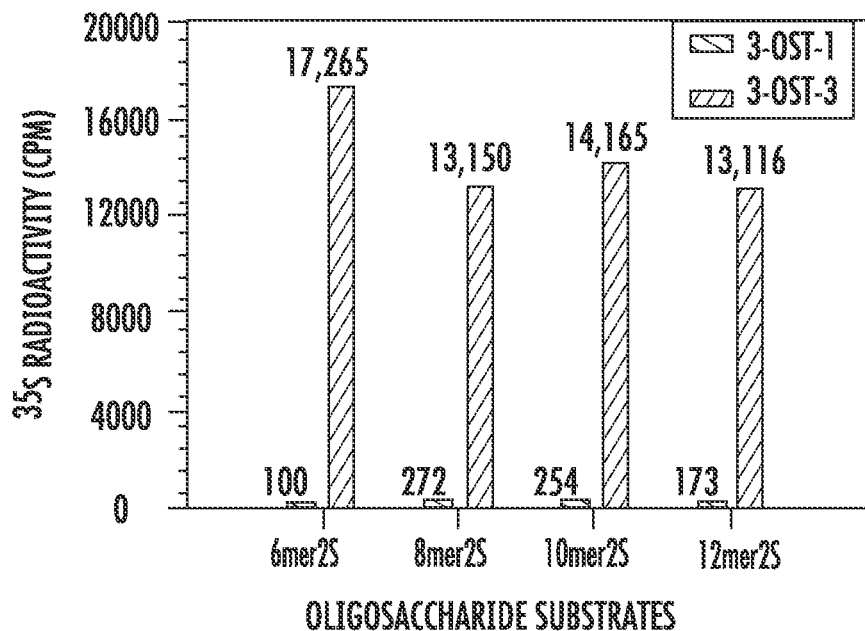
FIGS. 5A through 5C illustrate the substrate requirements for 3-OST-1 and 3-OST-3 using different sizes of structurally homogeneous oligosaccharides, where
Figure 5B:
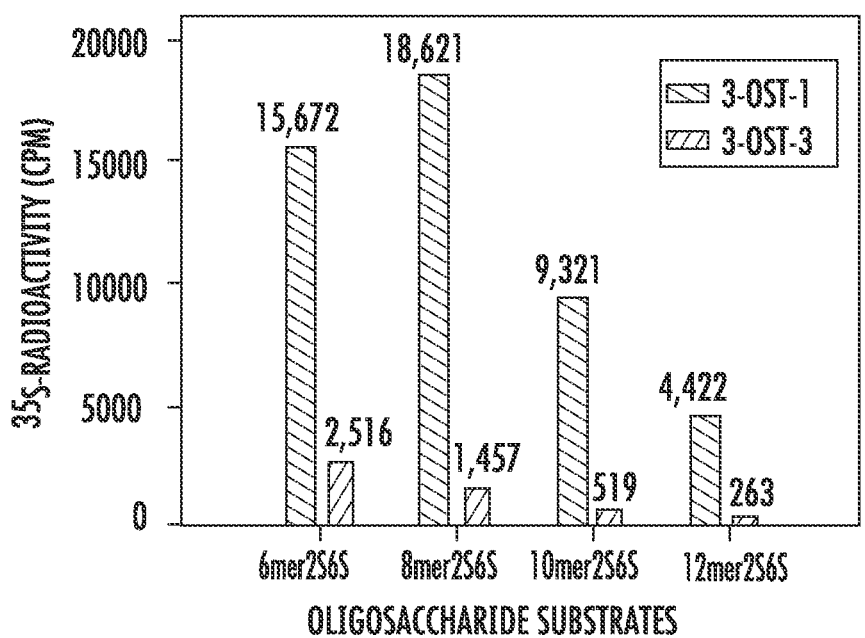
Figure 5C:
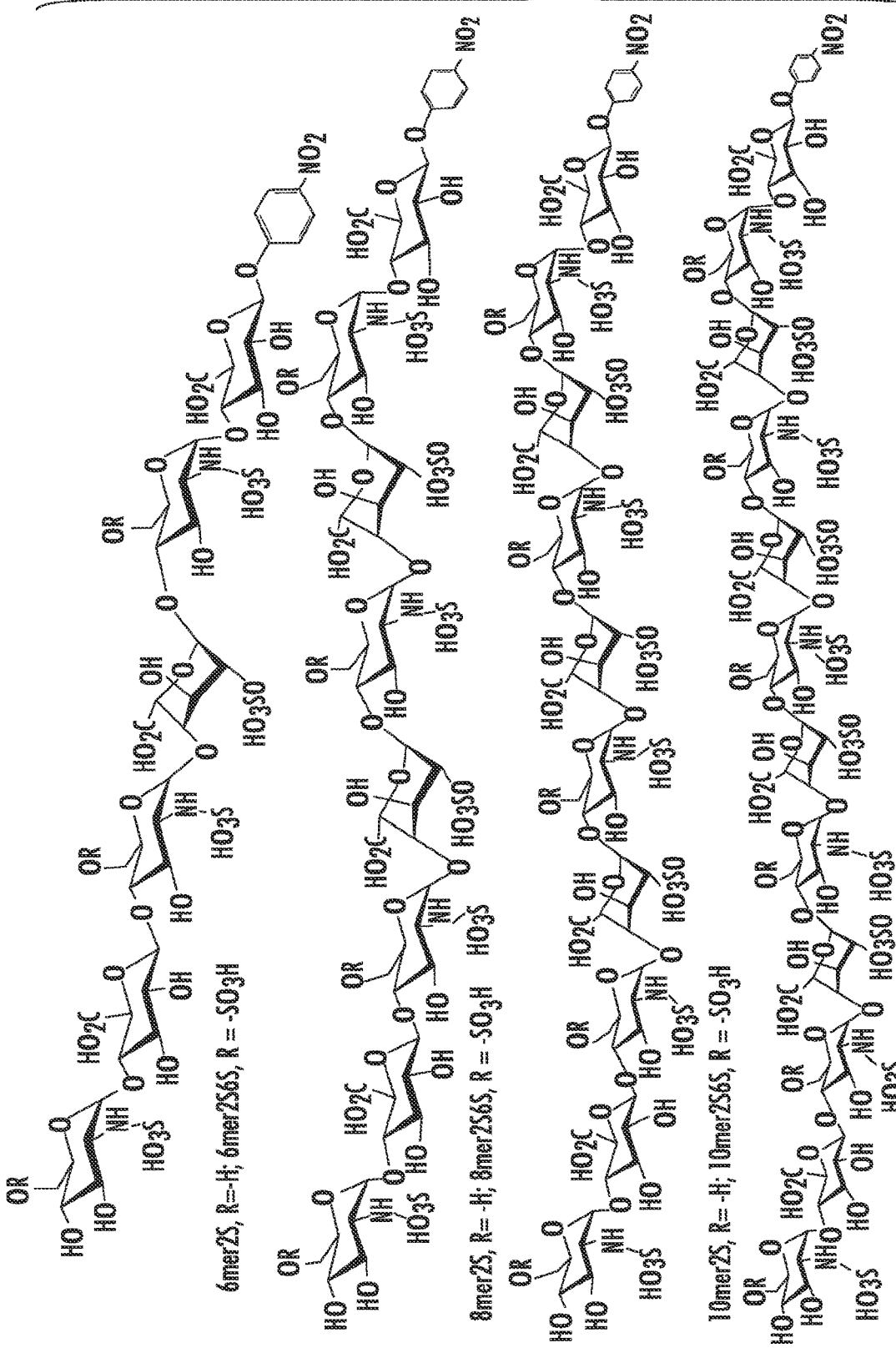

Disclosed herein is the discovery that 3-OST-3 and 3-OST-1 have different substrate requirements. The 3-OST-1 enzyme sulfates oligosaccharide substrates that carry 6-O-sulfation, while displaying very low reactivity towards the oligosaccharide substrates that lack 6-O-sulfation (FIGS. 5A and 5B), which is consistent with the conclusions described previously[16]. In contrast, 3-OST-3 preferentially sulfates oligosaccharides that do not carry 6-O-sulfation (FIGS. 5A and 5B), but the reactivity of those 6-0-sulfated oligosaccharide substrates to 3-OST-3 modification was low (FIGS. 5A, 5B and 5C). Results from kinetic analysis demonstrate that 3-OST-3 has higher catalytic efficiency for oligosaccharide substrates without 6-O-sulfation as determined by the values of kcat/Km (Table 1).

TABLE 1

Kinetic parameters of 3-OST-3 towards oligosaccharide substrates

|  | 6mer2s | 6mer2S6S | 8mer2S | 8mer2S6S | 10mer2s | 10mer2S6S | 12mer2S | 12mer2S6S |
| --- | --- | --- | --- | --- | --- | --- | --- | --- |
| $K_m$ (µM) | 364.5 | 20.7 | 86.9 | 23.1 | 44.1 | 16.6 | 31.4 | 7.7 |
| $k_{cat}$ (min$^{-1}$) | 0.49 | 0.018 | 0.73 | 0.095 | 0.49 | 0.05 | 0.61 | 0.03 |
| $k_{cat}/K_m$ $10^5 \times$ (M $\times$ min)$^{-1}$ | 0.013 | 0.0086 | 0.084 | 0.041 | 0.1 | 0.03 | 0.2 | 0.04 |

The discovery of distinct substrate requirements for 3-OST-1 and 3-OST-3 led to the development, as disclosed herein, of two separate schemes to synthesize oligosaccharides that contain different 3-O-sulfated saccharide sequences. For the synthesis of oligosaccharides containing the IdoA2S-GlcNS3S±6S disaccharide unit (compound 1, 2, 4 and 5, depicted in FIGS. 6A, 6B, 6D and 6E, respectively), 3-O-sulfation by 3-OST-3 was introduced prior to the 6-O-sulfation step (FIG. 1B), whereas for the synthesis of oligosaccharides containing the GlcA-GlcNS3S6S disaccharide unit, the 3-O-sulfation by 3-OST-1 was performed after the 6-O-sulfation step (FIG. 1B) (compound 3 and 6, depicted in FIGS. 6C and 6F). The AT-binding domain comprises a pentasaccharide unit of -GlcNS(or Ac)6S-GlcA-GlcNS3S±6S-IdoA2S-GlcA-GlcNS6S-, of which the 3-O-sulfation is can be needed for high binding affinity[24,29]. Among all the oligosaccharides tested in this study, only compound 8 and 11 contain the pentasaccharide unit.

Example 2

Structural and Conformational Analysis of Oligosaccharides

Figure 2A:
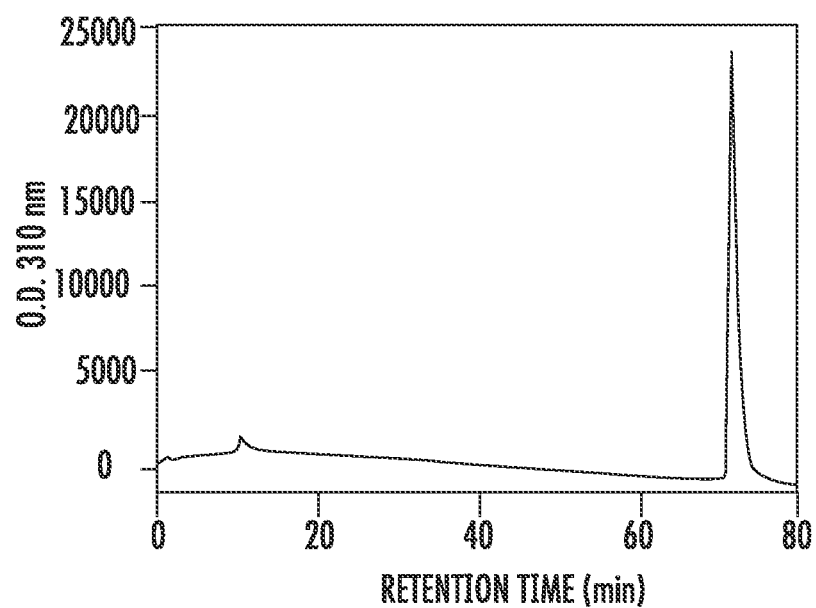
FIG. 2A is a graphical depiction of results of high resolution anion exchange HPLC.
Figure 2B:
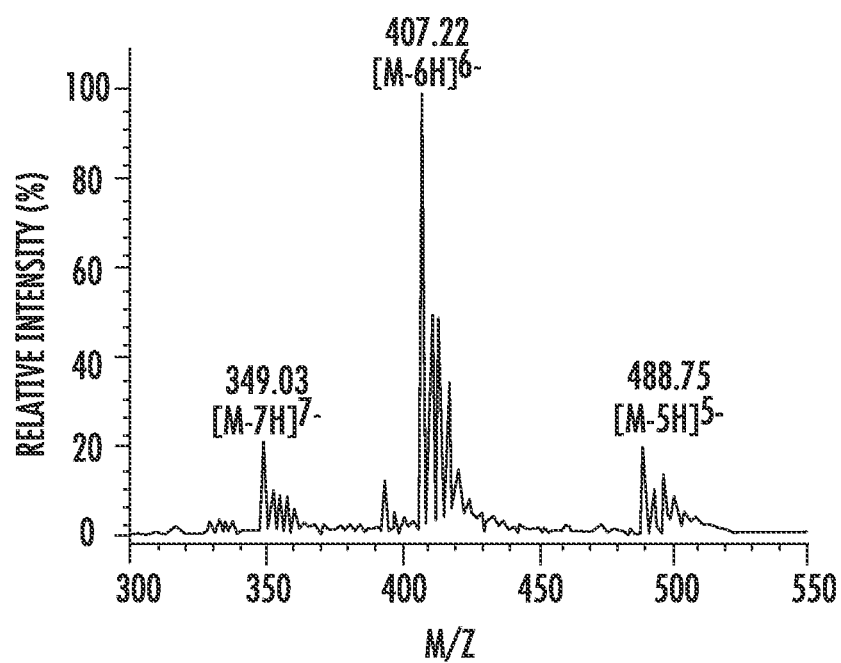
FIG. 2B shows the results of electrospray ionization mass spectrometry (ESI-MS), both conducted on compound 6 to demonstrate the purity and structural analysis of the oligosaccharides disclosed herein.
Figure 6A:
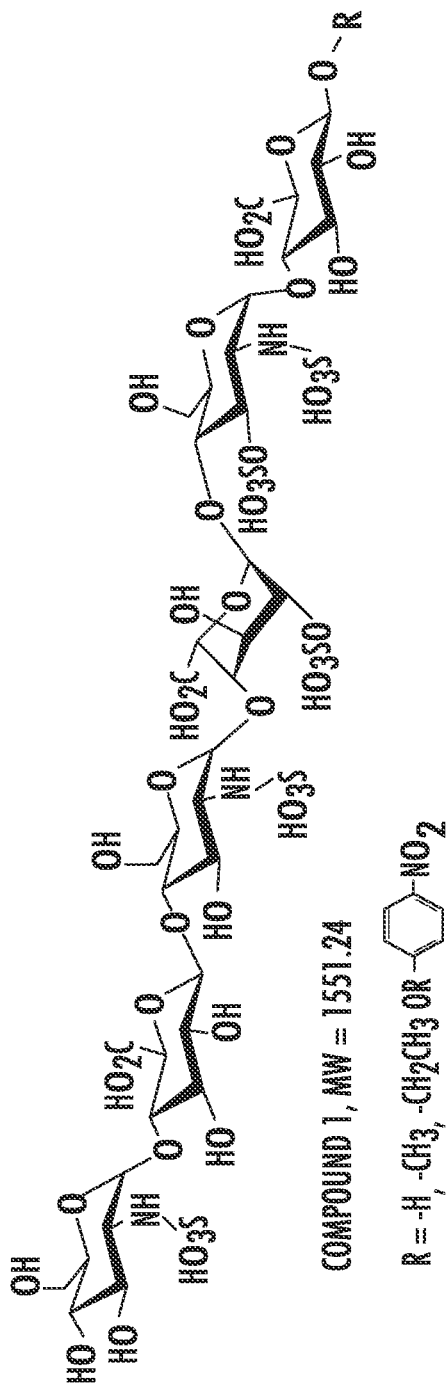
FIGS. 6A through 6F are schematics of the chemical structures of compounds 1, 2, 3, 4, 5 and 6, respectively.
Figure 6B:
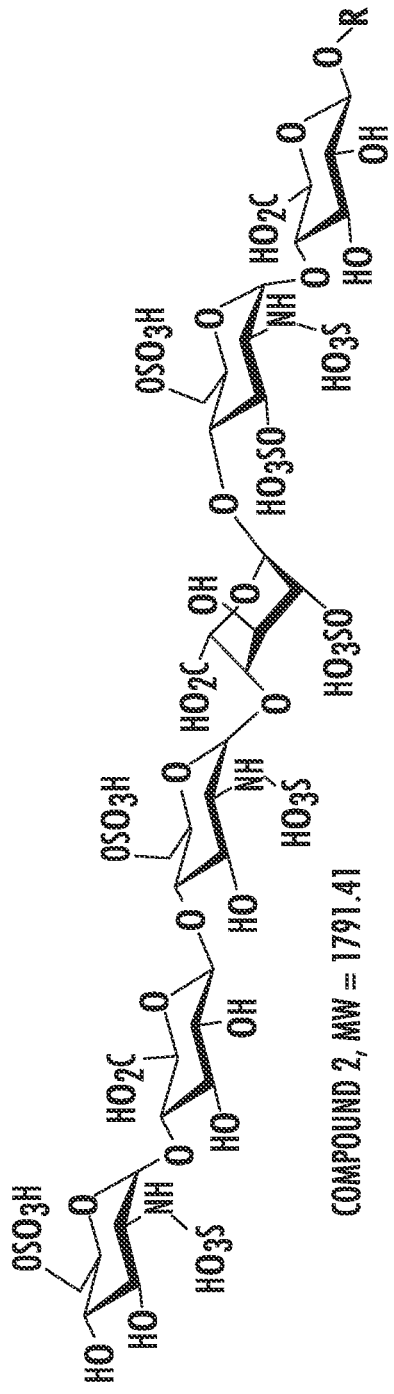
Figure 6C:
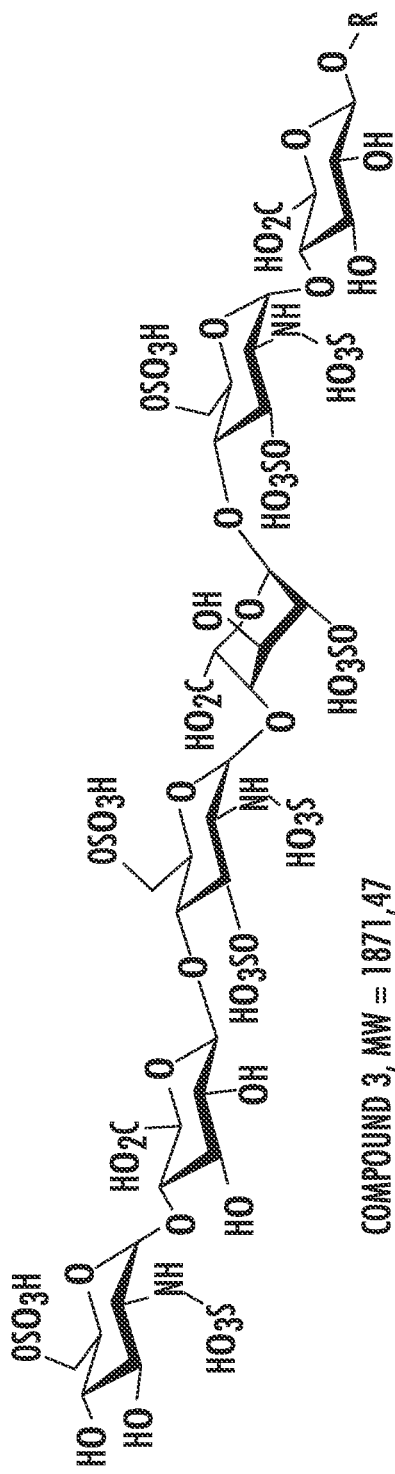
Figure 6C:
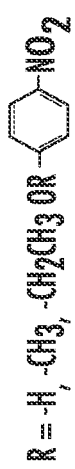
Figure 6D:
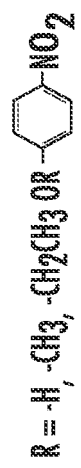
Figure 6E:
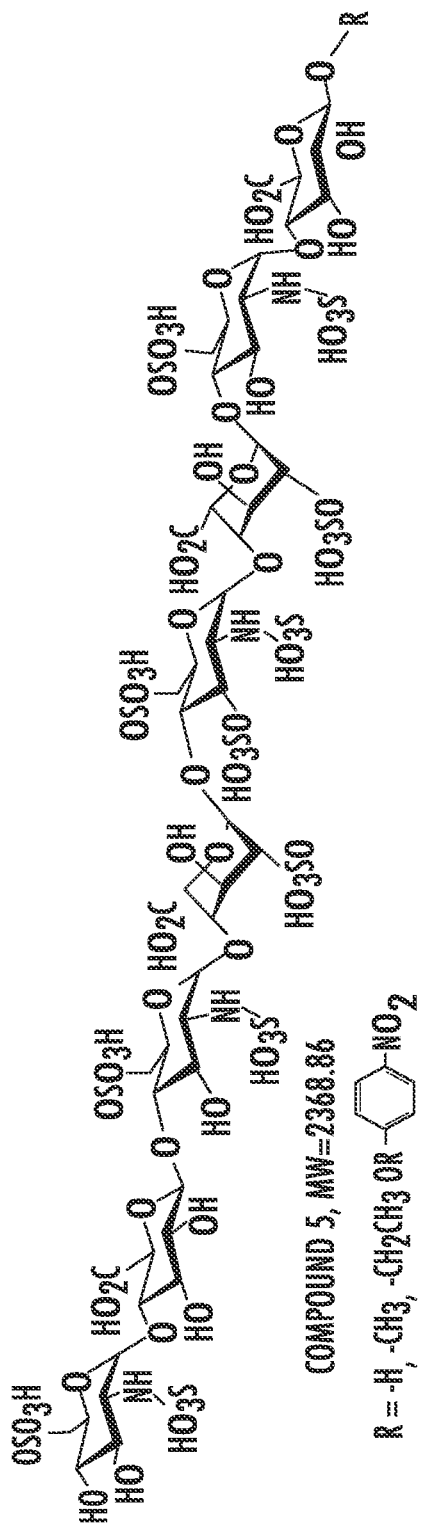
Figure 6F:
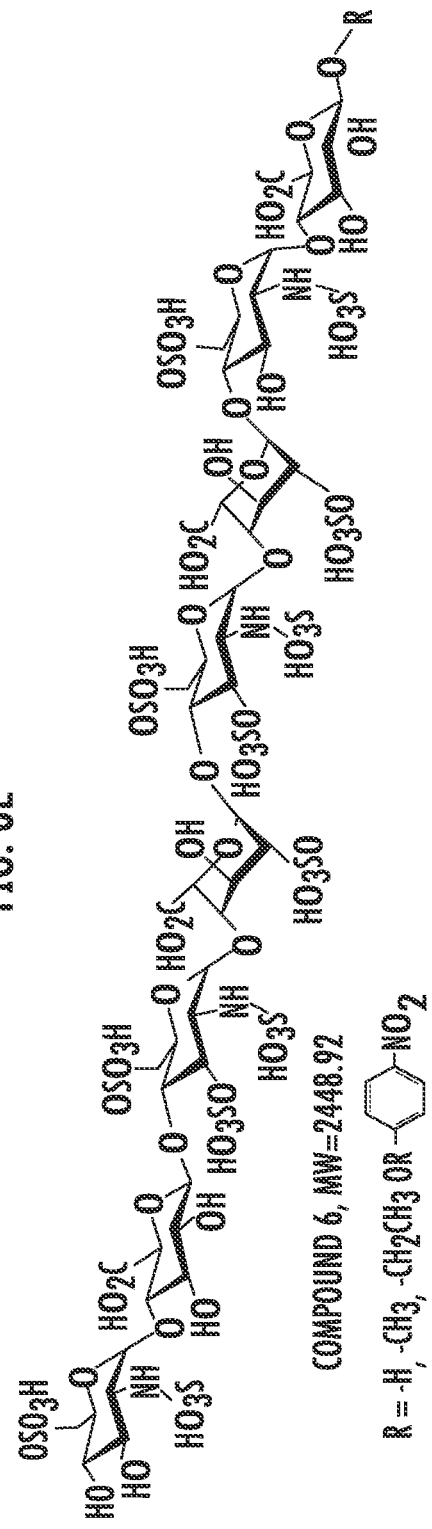

The purity and structural analysis of compound 1 to 6 was conducted, representative data for the analysis of compound 6, depicted in FIG. 6E, are shown in FIGS. 2A and 2B. Compound 6 was eluted as a single peak from high resolution anion exchange HPLC, suggesting that the compound is pure (FIG. 2A). The molecular mass of compound 6 was determined to be 2449.43±0.74 by electrospray ionization mass spectrometry (ESI-MS), which is very close to the calculated molecular mass of 2448.92 (FIG. 2B). The 1H-NMR spectrum of compound 6 clearly shows eight anomeric protons, confirming that the product is an octasaccharide. The 13C-NMR and full NMR assignment for compound 6 are shown in Supplementary FIG. and Supplementary Table 1, respectively. To locate the 3-O-sulfo group in compound 4, tandem MS analysis was carried out. In this analysis, a stable isotopically labeled [34S]sulfo group was introduced by the 3-OST-3 enzyme, allowing us to unambiguously identify the presence of the 3-O-sulfo group at residue d in compound 4. As compound 4 was the intermediate for compound 5 and 6, the tandem MS analysis of compound 4 also helped to locate the IdoA2S-GlcNS3S6S disaccharide unit in compound 5 and 6.

Figure 1C:
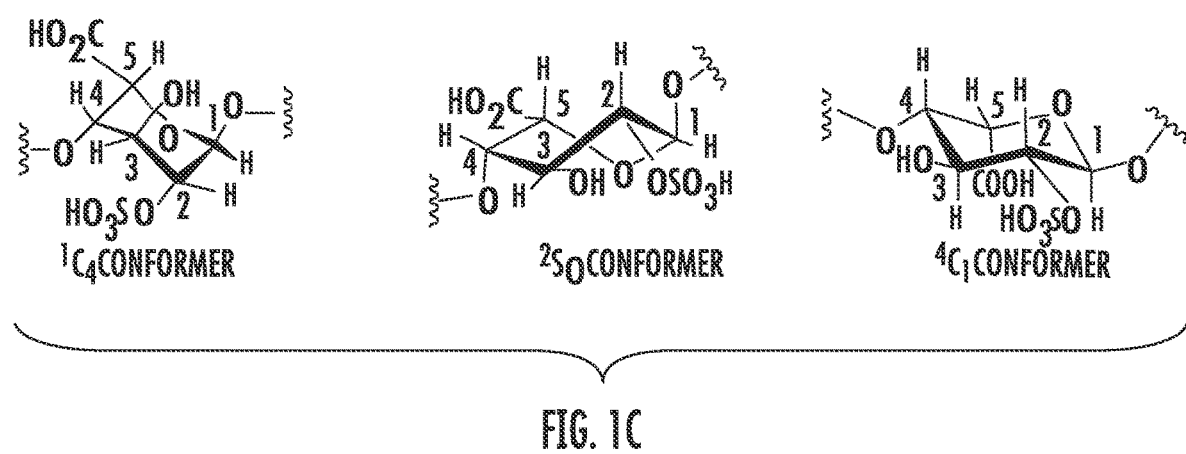

The pyranose rings of IdoA2S residues interconvert between different conformations, including chair forms (1C4 and 4C1) and the skew boat form (2SO) (FIG. 1C). The impact of 3-O-sulfation on the conformation of neighboring IdoA2S residues was investigated. The conformational analysis was completed by NMR through measuring the three bond proton-proton coupling constants $(^3J_{H-H})^3$. The 3-O-sulfation increases the population of 2SO conformer of the IdoA2S residue in hexasaccharides (compound 1 to 3, Table 2 and FIG. 1A), compared that of the IdoA2S residue in a hexasaccharide without the GlcNS3S6S residue (compound 7). In compound 3, the IdoA2S residue almost exclusively displays the 2SO conformation. For octasaccharides (compound 4 to 6, Table 2 and FIG. 1A), two IdoA2S residues exist, designated as residue c and e. The effect of 3-O-sulfation on the 2SO population varies. For example, 3-O-sulfation increases the 2SO population for both flanked IdoA2S residues as displayed in compound 5, compared with those of IdoA2S residues in an octasaccharide without the GlcNS3S6S residue (compound 10). In compound 11, the 3-O-sulfation on residue f increases 2SO population of the adjacent IdoA2S residue (residue e), but has no effect on a distant IdoA2S residue (residue c), compared with corresponding residues in compound 10. In compound 6, 3-O-sulfation on residue d and f increases the 2SO population of residue e, but decreases 2SO population of residue c to 58% from 71% (Table 2), compared with the corresponding residues from compound 5. These observations suggest that 3-O-sulfation could regulate the structure of HS through its effect on the conformation of IdoA2S residues.

TABLE 2

Effects of the GlcNS3S6S or GlcNS3S residue on the population of conformers for IdoA2S in oligosaccharides

| Compounds: Abbreviated oligosaccharide structures | Site of IdoA2S residue | Measured $^3J_{H-H}$ couplings (Hz) (Calculated $^3J_{H-H}$ couplings) | | | | Population of conformers[b] | | | Sum of square difference[c] |
|---|---|---|---|---|---|---|---|---|---|
| | | $^3J_{H1-H2}$ | $^3J_{H2-H3}$ | $^3J_{H3-H4}$ | $^3J_{H4-H5}$ | $^1C4$ | $^2SO$ | $^4C1$ | |
| Hexa-saccharides | | | | | | | | | |
| Comp 7: GlcNS-GlcA-GlcNS-IdoA2S-GlcNS-GlcA-pNP[d] | c | 2.2 (2.7)[a] | 4.3 (4.1) | 3.2 (3.0) | 2.3 (2.2) | 68% | 32% | — | 0.34 |
| Comp 1: GlcNS-GlcA-GlcNS-IdoA2S-GlcNS3S-GlcA-pNP[e] | c | 2.6 (3.1) | 5.0 (4.7) | 3.3 (3.3) | 2.5 (2.3) | 58% | 42% | — | 0.38 |
| Comp 2: GlcNS6S-GlcA-GlcNS6S-IdoA2S-GlcNS3S6S-GlcA-pNP | c | 4.1 (4.8) | 7.8 (7.3) | 3.9 (4.3) | 3.2 (2.9) | 19% | 81% | — | 0.99 |
| Comp 3: GlcNS6S-GlcA-GlcNS3S6S-idoA2S-GlcNS3S6S-GlcA-pNP | c | 4.8 (5.5) | 9.0 (8.4) | 4.3 (4.8) | 3.5 (3.1) | — (1%) | 99% | — | 1.26 |
| Octa-saccharides | | | | | | | | | |
| Comp 9: GlcNAc-GlcA-GlcNS-IdoA2S-GlcNS-IdoA2S-GlcNS-GlcA-pNP | c | 2.5 (3.0) | 4.7 (4.6) | 3.5 (3.3) | 2.5 (2.3) | 62% | 37% | — (2%) | 0.34 |
| | e | 2.1 (2.5) | 4.0 (3.7) | 3.3 (3.0) | 2.3 (2.1) | 72% | 24% | — (3%) | 0.38 |
| Comp 4: GlcNS-GlcA-GlcNS-IdoA2S-GlcNS3S-IdoA2S-GlcNS-GlcA-pNP | c | 2.8 (3.3) | 5.3 (5.1) | 3.5 (3.4) | 2.7 (2.4) | 53% | 47% | — | 0.39 |
| | e | 2.2 (2.7) | 4.4 (4.2) | 3.3 (3.1) | 2.5 (2.2) | 67% | 33% | — | 0.42 |
| Comp 10: GlcNS6S-GlcA-GlcNS6S-IdoA2S-GlcNS6S-IdoA2S-GlcNS6S-GlcA-pNP | c | 3.1 (3.8) | 6.1 (5.8) | 3.8 (3.7) | 2.8 (2.5) | 42% | 58% | — | 0.68 |
| | e | 3.2 (3.8) | 6.1 (5.8) | 3.8 (3.7) | 2.9 (2.5) | 41% | 59% | — | 0.62 |
| Comp 5: GlcNS6S-GlcA-GlcNS6S-IdoA2S-GlcNS3S6S-IdoA2S-GlcNS6S-GlcA-pNP | c | 3.6 (4.3) | 7.0 (6.6) | 4.0 (4.1) | 3.1 (2.7) | 29% | 71% | — | 0.82 |
| | e | 3.9 (4.5) | 7.3 (6.9) | 4.0 (4.2) | 3.0 (2.8) | 25% | 75% | — | 0.60 |
| Comp 6: GlcNS6S-GlcA-GlcNS3S6S-IdoA2S-GlcNS3S6S-IdoA2S-GlcNS6S-GlcA-pNP | c | 3.0 (3.8) | 6.1 (5.8) | 3.9 (3.7) | 2.9 (2.5) | 42% | 58% | — | 0.93 |
| | e | 4.1 (4.8) | 7.8 (7.3) | 3.9 (4.3) | 3.2 (2.9) | 19% | 81% | — | 0.99 |
| Comp 11: GlcNAc6S-GlcA-GlcNS3S6S-IdoA2S-GlcNS6S-IdoA2S-GlcNS6S-GlcA-pNP | c | 3.1 (3.7) | 6.1 (5.7) | 3.7 (3.7) | 2.8 (2.5) | 43% | 57% | — | 0.61 |
| | e | 3.6 (4.4) | 7.2 (6.7) | 4.1 (4.1) | 3.1 (2.7) | 27% | 73% | — | 1.05 | a. The calculated values (presented in parentheses) were obtained using Amber 14 with GLYCAM06 parameters [45].
b. The conversion of the measured values of coupling constant to population of different conformers was described in a previous publication [30].
c. The residual sum of squares (RSS) was used to determine how well the calculated population ratios fit the experimental data.
d. The population of conformation of comp 7 was reported in a paper published previously [30].
e. The position of 3-O-sulfated glucosamine (GlcNS3S or GlcNS3S6S) is bolded and underlined.

Example 3

The Presence of the -GlcNS3S6S-IdoA2S-Disaccharide Unit Impacts Anticoagulant Activity.

Figure 3A:
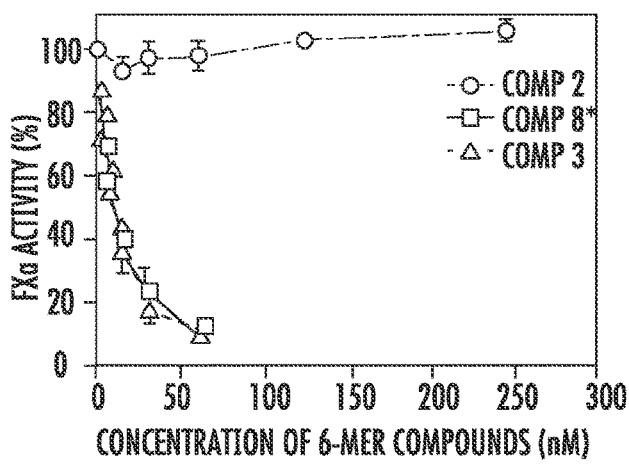
FIGS. 3A through 3D are graphical summaries of results illustrating the effects of the presence of the GlcNS3S6S-IdoA2S- disaccharide unit on anticoagulant activity.

HS oligosaccharides achieve their anticoagulant activity by interacting with AT, therefore oligosaccharides displaying anti-FXa activity should bind to AT. The effects of saccharide residues surrounding the GlcNS3S6S residue on the AT-binding as well as anti-FXa activity were examined. These data reveal that the presence of a -GlcNS3S6S-IdoA2S- disaccharide unit, i.e. an IdoA2S located at the reducing end of the GlcNS3S6S residue, can play a role in determining anticoagulant activity (Table 3). Compound 2 and 8 have six residues, eight sulfo groups, one IdoA2S and two GlcA residues, but only compound 8 displayed anti-FXa activity (FIG. 3A and Table 3). As expected, AT binds to compound 8 tightly with a Kd value of 7±2 nM, but not to compound 2 (Table 3). Structurally, the compounds differ in the location of the IdoA2S residue. In compound 8, the 3-O-sulfated glucosamine (GlcNS3S6S) residue is flanked by an IdoA2S residue at the reducing end such that it possesses the -GlcNS3S6S-IdoA2S- disaccharide unit, whereas the GlcNS3S6S in compound 2 is flanked by a GlcA residue at the reducing end such that it possesses the -GlcNS3S6S-GlcA-disaccharide unit.

TABLE 3

Correlation between the disaccharide domain (-GlcNS3S6S-IdoA2S-) and AT-binding constant ($K_d$) as well as anti-FXa activity ($IC_{50}$)

|  | Abbreviated structures | Binding affinity (Kd) to AT (nM) | Anti-FXa activity (IC50, nM) |
|---|---|---|---|
| Fondaparinux, 5-mer | GlcNS6S-GlcA-GlcNS3S6S-IdoA2S-GlcNS6S-OMe[a] | 14.8 ± 1.4 nM | 12.2 nM |
| *Hexasaccharides* | | | |
| Comp 8[b] | GlcNS6S-GlcA-GlcNS3S6S-IdoA2S-GlcNS6S-GlcA-pNP | 7 ± 2 nM[b] | 9.1 nM |
| Comp 2 | GlcNS6S-GlcA-GlcNS6S-IdoA2S-GlcNS3S6S-GlcA-pNP | No binding | No inhibition |
| Comp 3 | GlcNS6S-GlcA-GlcNS3S6S-IdoA2S-GlcNS3S6S-GlcA-pNP | Not measured | 11.0 nM |
| IdoA-containing 6-mer | GlcNS6S-GlcA-GlcNS3S6S-IdoA-GlcNS6S-GlcA-pNP[c] | 32.6 ± 5.3 nM[d] | 29.2 nM[d] |
| GlcA2S-containing 6-mer | GlcNS6S-GlcA-GlcNS3S6S-GlcA2S-GlcNS6S-GlcA-pNP[d] | No binding[d] | Not measured |
| *Octasaccharides* | | | |
| Comp 4 | GlcNS-GlcA-GlcNS-IdoA2S-GlcNS3S-IdoA2S-GlcNS-GlcA-pNP | No binding[c] | No inhibition |
| Comp 5 | GlcNS6S-GlcA-GlcNS6S-IdoA2S-GlcNS3S6S-IdoA2S-GlcNS6S-GlcA-pNP | 5.1 ± 1.4 nM | 7.7 nM |
| Comp 6 | GlcNS6S-GlcA-GlcNS3S6S-IdoA2S-GlcNS3S6S-IdoA2S-GlcNS6S-GlcA-pNP | 5.6 ± 2.6 nM | 10.9 nM |
| Comp 11 | GlcNAc6S-GlcA-GlcNS3S6S-IdoA2S-GlcNS6S-IdoA2S-GlcNS6S-GlcA-pNP | 8 ± 3 nM[1] | 9.4 nM |

[a]Fondaparinux, an FDA-approved anticoagulant, was used as a positive control for anti-FXa activity measurement and the binding to AT. The -GlcNS3S6S-IdoA2S-disaccharide units are presented in bold face and underlined.
[b]The binding constants for comp 8 and comp 11 were determined by affinity coelectrophoresis as reported in a previous publication[17].
[c]Comp 4 did not bind to AT nor display anti-FXa activity, due to the fact that it does not contain 6-O-sulfo groups at the GlcNS residues at the nonreducing end[29].
[d]The IdoA-containing 6-mer was reported in a previous publication[30]. IdoA also displays both $^1C_4$ and $^2S_O$ conformations. The GlcA2S-containing 6-mer was reported in a previous publication[8].

The findings herein are consistent with the previously published conclusion that the $^2SO$ conformation impacts anticoagulant activity[9]. The IdoA2S residue in compound 8 displays the $^2SO$ conformation; whereas in compound 2, this position is occupied by a GlcA residue that adopts the $^4C1$ conformation. The X-ray crystal structure and NMR solution structure of the complex of AT and fondaparinux demonstrate that the IdoA2S residue is present in $^2SO$ conformation in the complex[31,32]. An IdoA-containing 6-mer, where the IdoA2S residue was substituted with an IdoA residue displaying $^2SO$ conformation, exhibited anti-FXa activity[30] (Table 3). However, a GlcA2S-containing 6-mer, where the IdoA2S residue was substituted with a GlcA2S residue displaying $^4C1$ conformation, did not display anti-FXa activity (Table 2). Compound 3 displayed strong anti-FXa activity as the 6-mer consists of two GlcNS3S6S residues (FIG. 3A and Table 3), consistent with previously published results for an octasaccharide consisting a similar pentasaccharide domain[32]. Residues d and c in compound 3 constitute the -GlcNS3S6S-IdoA2S- disaccharide unit.

Example 4

The GlcA Residue in the AT-Binding Domain is Substitutable by an IdoA2S Residue

Figure 3B:
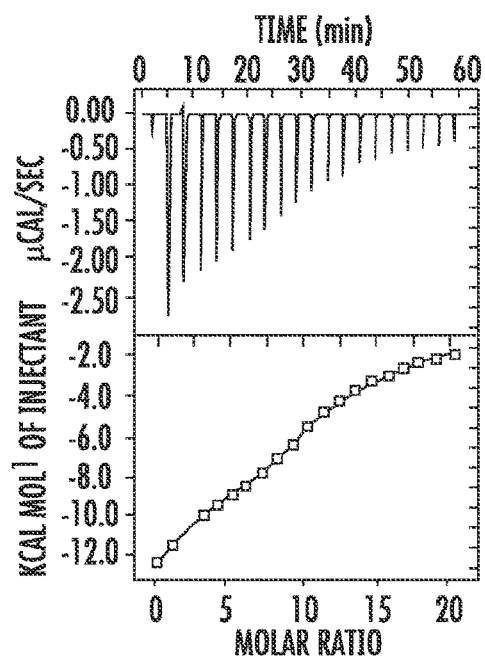

These studies uncovered a new AT-binding saccharide sequence. The currently known AT-binding sequence comprises a disaccharide -GlcA-GlcNS3S±6S- unit[33]. The substitution of the -GlcA-GlcNS3S6S- disaccharide unit with the -IdoA2S-GlcNS3S6S- disaccharide unit in HS was perceived to abolish AT-binding affinity[34,35]. The data from the anti-FXa activity and AT-binding analysis of the 8-mers clearly challenged this assertion. Compound 5, which contains the -IdoA2S-GlcNS3S6S- (but not -GlcA-GlcNS3S6S-) disaccharide unit, displays strong anti-FXa activity (Table 3). The AT-binding affinity analysis using isothermal titration calorimetry (ITC) also demonstrated that compound 5 binds to AT tightly (FIG. 3B and Table 3). Compound 6 displays anti-FXa activity and high AT-binding affinity (Table 3), as this 8-mer contains the -GlcA-GlcNS3S6S- disaccharide unit.

Figure 3C:
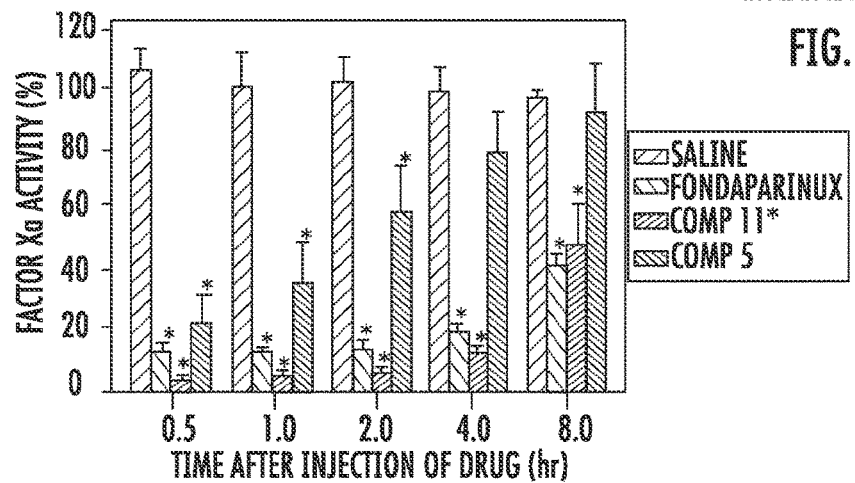
Figure 3D:
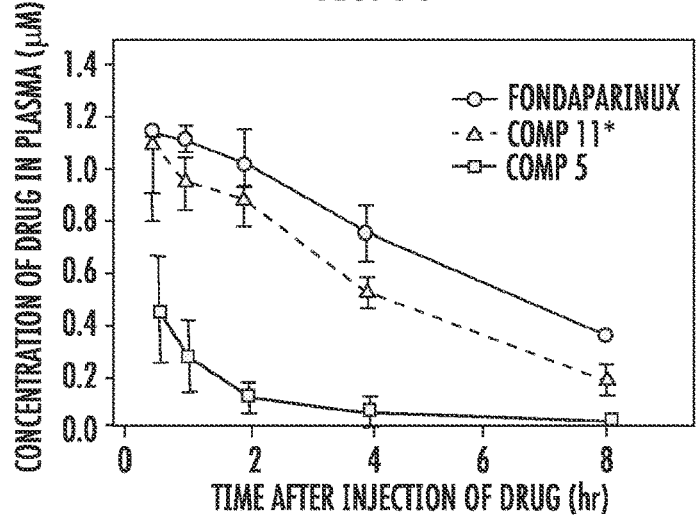

The anticoagulant activity of compound 5 was further confirmed in an in vivo experiment using a rat model. To this end, compound 5 was administered and compared the anti-FXa effect with fondaparinux and compound 11, an anticoagulant octasaccharide reported previously[7]. The results demonstrated that compound 5 has comparable anti-FXa potency to that of fondaparinux and compound 11 (FIG. 3C) within 30 min after the drug was administered. However, the anti-FXa effect from compound 5 diminished after 4 hours, while the anti-FXa effect from fondaparinux and compound 11 persisted after 8 hours (FIG. 3C). The drug concentrations in the blood sample were also obtained to determine the clearance rate of each compound in vivo (FIG. 3D). In comparison with fondaparinux and compound 11, compound 5 was cleared faster from the animal in the first 2 hours.

Figure 4B:
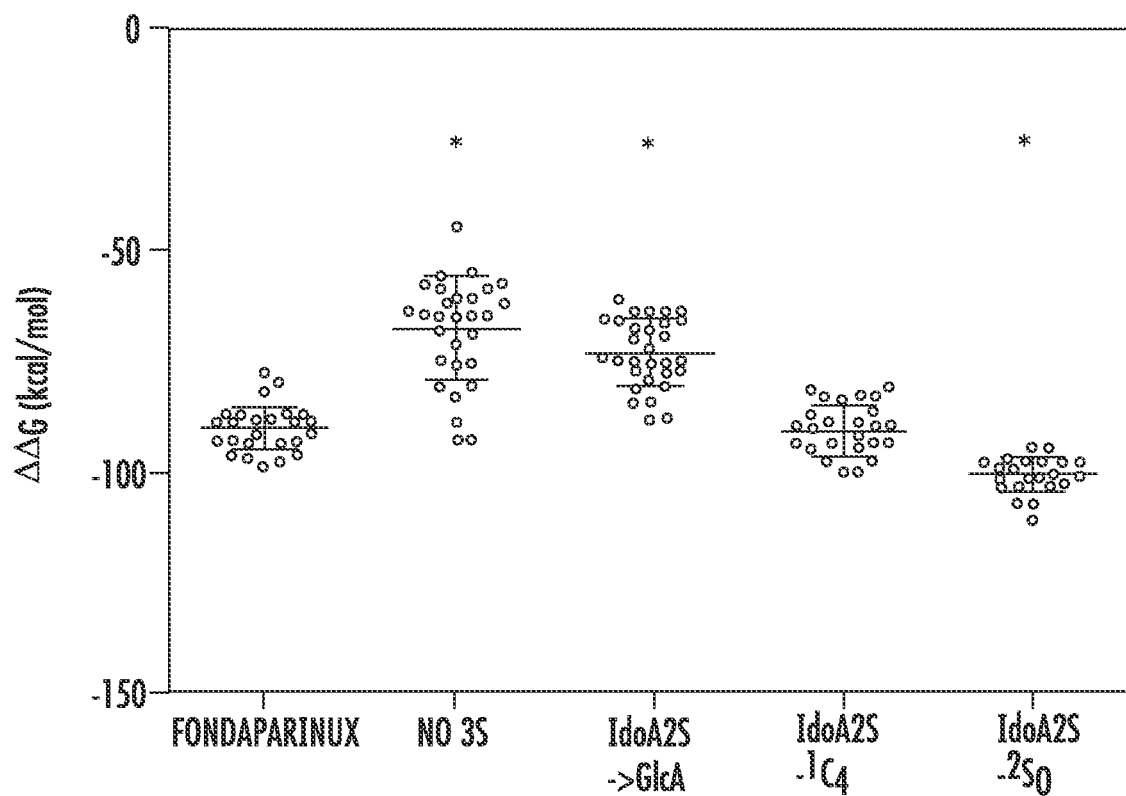

The structural promiscuity for residue d in the AT-binding site (FIG. 4A) is supported by molecular dynamics (MD) simulations of AT in complex with variously modified HS pentasaccharides. The computational technique was first validated by substituting moieties that are known to be essential for AT-binding within an existing co-crystal structure of AT and fondaparinux[24,36]. Calculations for the free energy of binding confirmed that removal of the 3-O-sulfate on residue c or substitution of residue b with GlcA destabilized the complex, indicated by significantly weakened interaction energy by 29% and 17%, respectively, qualitatively consistent with experimental data. In contrast, substitution of GlcA (residue d) with an IdoA2S in $^1C4$ conformation had no effect on free energy (FIG. 4B). Interestingly, substitution with an IdoA2S residue in 2SO conformation modestly enhanced the binding energy by 12% (FIG. 4B), suggesting the possibility of a more stable AT/pentasaccharide complex if residue d is IdoA2S in $^2$SO conformer. IdoA2S in both conformations were capable of maintaining a similar position of the carboxyl moiety with respect to the protein as was found for the GlcA residue in the simulation of fondaparinux. Collectively, the MD data support the conclusion that substitution of residue d with an IdoA2S residue does not diminish the binding affinity to AT, and explain how Compound 5 acts as an active anticoagulant despite lacking the canonical pentasaccharide sequence for AT.

Example 5

Analysis of 7-Mer HS Compound

Figure 7A:
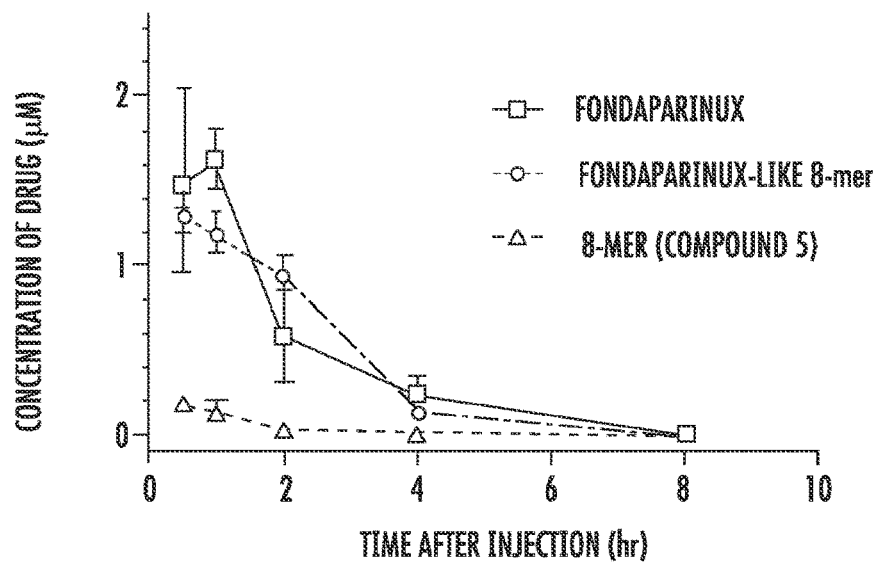
FIG. 7A is a graphical summary of data demonstrating that heparin compounds disclosed herein have faster clearance than fondaparinux in a C57BL/6J mouse model.
Figure 7B:
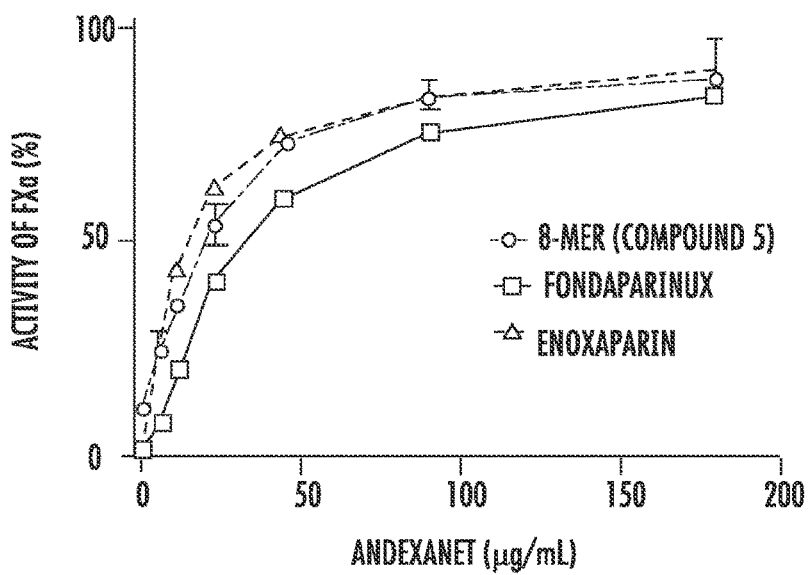
FIG. 7B is a graphical summary of data demonstrating that the anti-Fxa activity of heparin compounds disclosed herein is reversible by andexanet alfa (AndexXa®, Portola Pharmaceuticals, South San Francisco, Calif., United States of America)
Figure 8A:
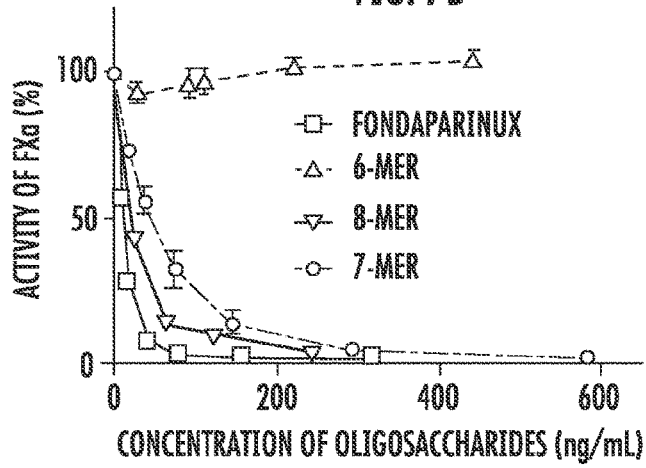
Figure 8C:
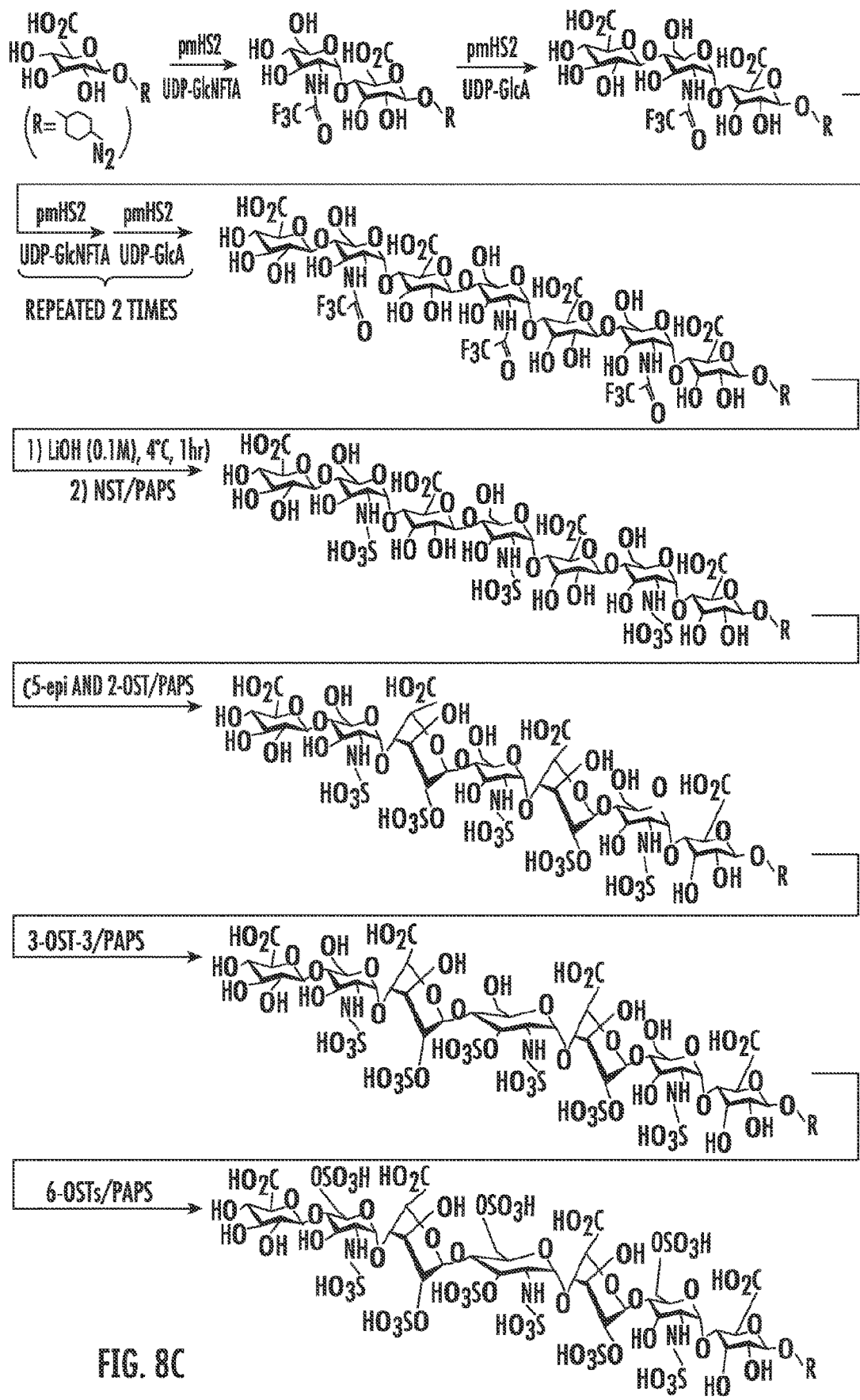

A 7-mer HS compound or heparin analogue was developed using the disclosed synthesis methods. The 7-mer, the structure of which is shown in FIG. 8B, was tested for and demonstrates anti-Xa activity (FIG. 8A). FIG. 8B schematically compares the chemical structural of the 7-mer to a 6-mer and 8-mer as disclosed herein. By way of example and not limitation, at least one synthetic pathway for synthesizing the 7-mer is shown in FIG. 7C. In some embodiments, it can be preferable to have a relatively shorter oligosaccharide, such as a 7-mer, since this can allow for a reduction in costs associated with synthesis.

Example 6

Discussion of Results

Disclosed herein are schemes using the chemoenzymatic approach to prepare a 3-O-sulfated oligosaccharide library. It is demonstrated herein that the 3-OST-3 modification, to synthesize oligosaccharides comprising the -IdoA2S-GlcNS3S- or -IdoA2S-GlcNS3S6S- disaccharide unit, must precede the 6-O-sulfation step, whereas 3-OST-1 modification can occur only after 6-O-sulfation in order to generate the -GlcA-GlcNS3S6S- disaccharide unit. This finding is supported by the ternary cocrystal structures of 3-OST-1/heptasaccharide/PAP[37] and 3-OST-3/tetrasaccharide/PAP[88]. There were no interactions between 3-OST-3 and the 6-O-sulfo groups from the tetrasaccharide substrate, consistent with the conclusion that oligosaccharide substrates for 3-OST-3 do not require 6-O-sulfation. In contrast, interactions between 3-OST-1 and the 6-O-sulfo groups from the heptasaccharide substrate were observed, suggesting that 6-O-sulfation is required to bind to 3-OST-1. The distinct and unique substrate requirements between 3-OST-1 and 3-OST-3 raise a possibility that 3-O-sulfated HS modified by different isoforms of 3-OST are biosynthesized through different pathways.

It was widely accepted that the 3-OST-1 enzyme is responsible for synthesizing anticoagulant HS, whereas the 3-OST-3 enzyme is not[34,35]. The AT-binding sequences isolated so far all consist of the -GlcA-GlcNS3S6S- disaccharide repeating unit, which is a product of 3-OST-1 enzyme modification[33,39]. Although Compound 5, which is a product of 3-OST-3 enzyme modification, does not contain the -GlcA-GlcNS3S6S- disaccharide unit, it binds to AT and displays anticoagulant activity. These findings suggest that 3-OST-3 is capable of synthesizing anticoagulant HS, as long as the HS comprises the structural domain similar to that of compound 5.

The fast clearance of compound 5 offers a potential new short-acting anticoagulant drug candidate with reduced bleeding risk. A short-acting anticoagulant drug, which can be cleared from the circulation quickly before major bleeding effects developed, would be particularly beneficial to those patients with high bleeding risk[41]. Although unfractionated heparin is an anticoagulant with a short half-life, the concern is that the drug causes heparin-induced thrombocytopenia (HIT), a life-threatening side effect[42]. It has been found that short oligosaccharides smaller than 12-mers[43] do not bind to platelet factor 4, and thus display no risk of HIT. As an octasaccharide, compound 5 is hence expected to have very low risk of HIT. The availability of 3-O-sulfated oligosaccharides also opens the opportunity to investigate the casual relationship between saccharide sulfation/conformation and biological functions, a major step forward in dissecting the structure and function relationship of HS. HS 3-OST exists in seven different isoforms. In the present study, we demonstrate that different chemoenzymatic schemes are required for 3-OST-1 and 3-OST-3 to prepare different 3-O-sulfated oligosaccharide sequences. The conclusion from this study will guide others to develop the chemoenzymatic method using different 3-OST isoforms, allowing the preparation of more complex HS saccharides with more extensive sulfation patterns involving 3-O-sulfated glucosamine residues. These studies will enrich the HS oligosaccharide library to assist HS-related research.

REFERENCES (1) Xu, D.; Esko, J. *Annu Rev Biochem.* 2014, 83, 129.
(2) Xu, D.; Olson, J.; Cole, J. N.; van Wijk, X. M.; Brinkmann, V.; Zychlinsky, A.; Nizet, V.; Esko, J. D.; Chang, Y. C. *Infect. Immun.* 2015, 83, 3648.
(3) Patel, V. N.; Lombaert, I. M. A.; Cowherd, S. N.; Shworak, N.; Xu, Y.; Liu, J.; Hoffman, M. P. *Developmental cell* 2014, 29, 662.
(4) Liu, J.; Linhardt, R. *J. Nat Prod Rep* 2014, 31, 1676.
(5) Kreuger, J.; Spillmann, D.; Li, J.-p.; Lindahl, U. *J. Cell Biol.* 2006, 174, 323.
(6) Sattelle, B. M.; Hansen, S. U.; Gardiner, J. M.; Almond, A. *J Am Chem Soc* 2010, 132, 13132.
(7) Sattelle, B. M.; Almond, A. *Glycobiology* 2011, 21, 1651.
(8) Hsieh, P.; Xu, Y.; Keire, D. A.; Liu, J. *Glycobiology* 2014, 24, 681.
(9) Das, S.; Mallet, J.; J, E.; Driguez, P.; Duchaussoy, P.; Sizun, P.; Herault, J.; Herbert, J.; M, P.; P, S. *Chemistry* 2001, 7, 4821.
(10) Raman, R.; Venkataraman, G.; Ernst, S.; Sasisekharan, R. *Proc. Natl. Acad. Sci.* 2003, 100, 2357.
(11) Hu, Y.-P.; Lin, S.-Y.; Huang, C.-Y.; Zulueta, M. M. L.; Liu, J.-Y.; Chang, W.; Hung, S.-C. *Nat Chem* 2011, 3, 557.
(12) Arungundram, S.; A-Mafraji, K.; Asong, J.; Leach III, F. E.; Amster, I. J.; Venot, A.; JE, T.; Boons, G. J. *J. Am. Chem. Soc.* 2009, 131, 17394.
(13) Schworer, R.; Zubkova, O. V.; Turnbull, J. E.; Tyler, P. C. *Chem. Eur. J.* 2013, 19, 6817.
(14) Zong, C.; Huang, R.; Condac, E.; Chiu, Y.; Xiao, W.; Li, Z. Q.; Lu, W.; Ishihara, M.; Wang, S.; Ramiah, A.; Stickney, M.; Azadi, P.; Amster, I. J.; Moremen, K. W.; Wang, L.; Sharp, J. S.; Boons, G.-J. *J. Am. Chem. Soc.* 2016, 138, 13059.
(15) Hansen, S. U.; Miller, G. J.; Cole, C.; Rushton, G.; Avizienyte, E.; Jayson, G. C.; Gardiner, J. M. *Nat Commun* 2013, 4:2016, doi: 10.1038/ncomms3016.
(16) Xu, Y.; Masuko, S.; Takieddin, M.; Xu, H.; Liu, R.; Jing, J.; Mousa, S. A.; Linhardt, R. J.; Liu, J. *Science* 2011, 334, 498.

(17) Xu, Y.; Cai, C.; Chandarajoti, K.; Hsieh, P.; Lin, Y.; Pham, T. Q.; Sparkenbaugh, E. M.; Sheng, J.; Key, N. S.; Pawlinski, R. L.; Harris, E. N.; Linhardt, R. J.; Liu, *J. Nat Chem Biol* 2014, 10, 248.

(18) Thacker, B. E.; Seamen, E.; Lawrence, R.; Parker, M. W.; Xu, Y.; Liu, J.; Vander, K. C. W.; Esko, J. D. *ACS Chem. Biol.* 2016, 11, 971.

(19) Lindahl, U.; Backstrom, G.; Thunberg, L.; Leder, I. G. *Proc. Natl. Acad. Sci.* 1980, 77, 6551.

(20) Shukla, D.; Liu, J.; Blaiklock, P.; Shworak, N. W.; Bai, X.; Esko, J. D.; Cohen, G. H.; Eisenberg, R. J.; Rosenberg, R. D.; Spear, P. G. *Cell* 1999, 99, 13.

(21) Kamimura, K.; Rhodes, J. M.; Ueda, R.; McNeely, M.; Shukla, D.; Kimata, K.; Spear, P. G.; Shworak, N. W.; Nakato, H. *J. Cell Biol.* 2004, 166, 1069.

(22) Tecle, E.; Diaz-Balzac, C. A.; Bulow, H. E. *G3 (Bethesda)* 2013, 3, 541.

(23) Tsau, C.; Ito, M.; Gromova, A.; Hoffman, M. P.; Meech, R.; Makarenkova, H. P. Development 2011, 138, 3307.

(24) Petitou, M.; van Boeckel, C. A. A. *Angew. Chem. Int. Ed.* 2004, 43, 3118.

(25) Liu, J.; Shriver, Z.; Pope, R. M.; Thorp, S. C.; Duncan, M. B.; Copeland, R. J.; Raska, C. S.; Yoshida, K.; Eisenberg, R. J.; Cohen, G.; Linhardt, R. J.; Sasisekharan, R. *J. Biol. Chem.* 2002, 277, 33456.

(26) Liu, J.; Pedersen, L. C. *Appl. Microbiol. Biotechnol.* 2007, 74, 263.

(27) Chen, J.; Avci, F. Y.; Muñoz, E. M.; McDowell, L. M.; Chen, M.; Pedersen, L. C.; Zhang, L.; Linhardt, R. J.; Liu, J. *J. Biol. Chem.* 2005, 280, 42817.

(28) Zhang, Z.; McCallum, S. A.; Xie, J.; Nieto, L.; Corzana, F.; Jiménez-Barbero, J.; Chen, M.; Liu, J.; Linhardt, R. J. *J Am Chem Soc* 2008, 130, 12998.

(29) Atha, D. H.; Lormeau, J.-C.; Petitou, M.; Rosenberg, R. D.; Choay, J. *Biochemistry* 1985, 24, 6723.

(30) Hsieh, P.-H.; Thieker, D. F.; Guerrini, M.; Woods, R. J.; Liu, J. *Sci Rep* 2016, 6, 29602; doi: 10.1038/srep29602.

(31) Jin, L.; Abrahams, P.; Skinner, R.; Petitou, M.; Pike, R. N.; Carrell, R. W. *Proc. Natl. Acad. Sci.* 1997, 94, 14683.

(32) Guerrini, M.; Elli, S.; Mourier, P.; Rudd, T. R.; Gaudesi, D.; Casu, B.; Boudier, C.; Torri, G.; Viskov, C. *Biochem. J.* 2013, 449, 343.

(33) Guerrini, M.; Mourier, P. A.; Torri, G.; Viskov, C. *Glycoconj. J.* 2014, 31, 409.

(34) Liu, J.; Shworak, N. W.; Sinaÿ, P.; Schwartz, J. J.; Zhang, L.; Fritze, L. M. S.; Rosenberg, R. D. *J. Biol. Chem.* 1999, 274, 5185.

(35) Xu, D.; Moon, A.; Song, D.; Pedersen, L. C.; Liu, J. *Nat Chem Biol* 2008, 4, 200.

(36) Langdown, J.; Belzar, K. J.; Savory, W. J.; Baglin, T. P.; Huntington, J. A. *J. Mol. Biol.* 2009, 386, 1278.

(37) Moon, A. F.; Xu, Y.; Woody, S.; Krahn, J. M.; Linhardt, R. J.; Liu, J.; Pedersen, L. C. *Proc. Natl. Acad. Sci.* USA 2012, 109, 5256.

(38) Moon, A.; Edavettal, S. C.; Krahn, J. X.; Munoz, E. M.; Negishi, M.; Linhardt, R. J.; Liu, J.; Pedersen, L. C. *J. Biol. Chem.* 2004, 279, 45185.

(39) deAgostini, A. I.; Dong, J.-C.; de Vantery Arrighi, C.; Ramus, M.-A.; Dentand-Quadri, I.; Thanlmann, S.; Ventura, P.; Ibecheole, V.; Monge, F.; Fischer, A.-M.; Haj-Mohammadi, S.; Shworak, N.; Zhang, L.; Zhang, Z.; Linhardt, R. J. *J. Biol. Chem.* 2008, 283, 28115.

(40) HajMohammadi, S.; Enjyoji, K.; Princivalle, M.; Christi, P.; Lech, M.; Beeler, D. L.; Rayburn, H.; Schwartz, J. J.; Barzegar, S.; de Agostini, A. I.; Post, M. J.; Rosenberg, R. D.; Shworak, N. W. *J. Clin. Invest.* 2003, 111, 989.

(41) Mahe, I.; Chidac, J.; Helfer, H.; Nobel, S. *J. Thromb. Haemost.* 2016, 14, 2017.

(42) McGowan, K. E.; Makari, J.; Diamantouros, A.; Bucci, C.; Rempel, P.; Selby, R.; Geerts, W. *Blood* 2016, 127, 1954.

(43) Kreimann, M.; Brandt, S.; Krauel, K.; Block, S.; Helm, C.; Weitschies, W.; Greinacher, A.; Delcea, M. *Blood* 2014, in press.

(44) Yang, J.; Hsieh, P.; Liu, X.; Zhou, W.; Zhang, X.; Zhao, J.; Xu, Y.; Zhang, F.; Linhardt, R. J.; Liu, *J. Chem Comm* 2017, 53, 1743.

(45) Kirschner, K. N.; Yongye, A. B.; Tschampel, S. M.; González-Outeiriño, J.; Daniels, C. R.; Foley, B. L.; Woods, R. J. *J. Comput. Chem.* 2008, 29, 622.

(46) Xu, Y.; Cai, C.; Chandarajoti, K.; Hsieh, P.; Lin, Y.; Pham, T. Q.; Sparkenbaugh, E. M.; Sheng, J.; Key, N. S.; Pawlinski, R. L.; Harris, E. N.; Linhardt, R. J.; Liu, J. *Nat Chem Biol* 2014, 10, 248.

(47) Langdown, J.; Belzar, K. J.; Savory, W. J.; Baglin, T. P.; Huntington, J. A. *J. Mol. Biol.* 2009, 386, 1278.

(48) Pettersen, E. F.; Goddard, T. D.; Huang, C. C.; Couch, G. S.; Greenblatt, D. M.; Meng, E. C.; Ferrin, T. E. *J. Comp. Chem.* 2004, 25, 1605.

(49) Fiser, A.; Sali, A. *Methods Enzymol* 2003, 374, 461.

(50) Huang, C. C.; Meng, E. C.; Morris, J. H.; Pettersen, E. F.; Ferrin, T. E. *Nucleic Acids Res.* 2014, 42, w478.

(51) Yang, Z.; Lasker, K.; Schneidman-Duhovny, D.; Webb, B.; Huang, C. C.; Pettersen, E. F.; Goddard, T. D.; Meng, E. C.; Sali, A.; Ferrin, T. E. *J. Struct. Biol.* 2012, 179, 269.

(52) Case, D. A.; Darden, T. A.; Cheatham III, T. E.; Simmerling, C. L.; Wang, J.; Duke, R. E.; Luo, R.; Walker, R. C.; Zhang, W.; Merz, K. M.; Roberts, B.; Hayik, S.; Roitberg, A.; Seabra, G.; Swails, J.; Goetz, A. W.; Kolossvery, I.; Wong, K. F.; Paesani, F.; Vanicek, J.; Wolf, R. M.; Liu, J.; Wu, X.; Brozell, S. R.; Steinbrecher, T.; Gohlke, H.; Cai, Q.; Ye, X.; Wang, J.; Hsieh, M.-J.; Cui, G.; Roe, D. R.; Mathews, D. H.; Seetin, M. G.; Salomon-Ferrer, R.; Sagui, C.; Babin, V.; Luchko, T.; Gusarov, S.; Kovalenko, A.; Kollman, P. A. 2014, University of California.

(53) Kirschner, K. N.; Yongye, A. B.; Tschampel, S. M.; González-Outeiriño, J.; Daniels, C. R.; Foley, B. L.; Woods, R. J. *J. Comput. Chem.* 2008, 29, 622.

(54) Singh, A.; Tessier, M. B.; Pederson, K.; Wang, X.; Venot, A. P.; Boons, G.-J.; Prestegard, J. H.; Woods, R. J. *Can. J. Chem.* 2016, 10.1139/cjc.

(55) Hsieh, P.-H.; Thieker, D. F.; Guerrini, M.; Woods, R. J.; Liu, *J. Sci Rep* 2016, 6, 29602; doi: 10.1038/srep29602.

(56) Darden, T.; York, D.; Pedersen, L. C. *J. Chem. Phys.* 1993, 98, 10089.

(57) Kollman, P. A.; Massova, I.; Reyes, C.; Kuhn, B.; Huo, S.; Chong, L.; Lee, M.; Lee, T.; Duan, Y.; Wang, W.; Donini, O.; Cieplak, P.; Srinivasan, J.; Case, D. A.; Cheatham, T. E. r. *Acc. Chem. Res.* 2000, 33, 889.

(58) Onufriev, A.; Bashford, D.; Case, D. A. *Proteins* 2004, 55, 383.

(59) Humphrey, W.; Dalke, A.; Schulten, K. *J. Mol. Graph.* 1996, 14, 33.

What is claimed is:
1. A synthetic heparin analogue which comprises disaccharide units of a glucuronic acid (GlcA) residue linked to a glucosamine (GlcN) residue modified by sulfation and an iduronic acid (IdoA) residue linked to a GlcN residue modified by sulfation, comprising:
  a 3-O-sulfated oligosaccharide comprising six to eight saccharide units;

at least one disaccharide unit sulfated by a 3-OST-3 enzyme;
at least one IdoA2S-GlcNS3 S or at least one IdoA2S-GlcNS3 S6S disaccharide unit, and is devoid of a GlcA-GlcNS3S6S disaccharide unit; and
at least one disaccharide unit comprising a GlcNS6S residue.

2. The synthetic heparin analogue of claim 1, wherein the synthetic heparin analogue has anticoagulant activity.

3. The synthetic heparin analogue of claim 1, wherein the synthetic heparin analogue has a binding affinity to antithrombin ranging from about 5 Nm to about 30 Nm.

4. The synthetic heparin analogue of claim 1, wherein the synthetic heparin analogue has anti-Xa activity ranging from about 10 ngml$^{-1}$ to about 40 ngml$^{-1}$ IC$_{50}$.

5. A synthetic heparin analogue, wherein the synthetic heparin analogue comprises a structure selected from the group consisting of:

8. The synthetic heparin analogue of claim 1, wherein the synthetic heparin analogue does not cause heparin-induced thrombocytopenia (HIT).

9. The synthetic heparin analogue of claim 1, wherein the anticoagulant activity of the synthetic heparin analogue is reversible by andexanet alfa at a rate of 50% or more in the presence of 20 ug/ml or less of andexanet alfa.

10. The method of claim 5, wherein the alkyl is —CH$_3$ or —CH$_2$CH$_3$ or the substituted aryl is a p-nitrophenyl group.

11. The method of claim 6, wherein the alkyl is —CH$_3$ or —CH$_2$CH$_3$ or the substituted aryl is a p-nitrophenyl group.

12. A pharmaceutical composition comprising a synthetic heparin compound of claim 1.

13. A pharmaceutical composition comprising a synthetic heparin compound of claim 5.

14. A pharmaceutical composition comprising a synthetic heparin compound of claim 6.

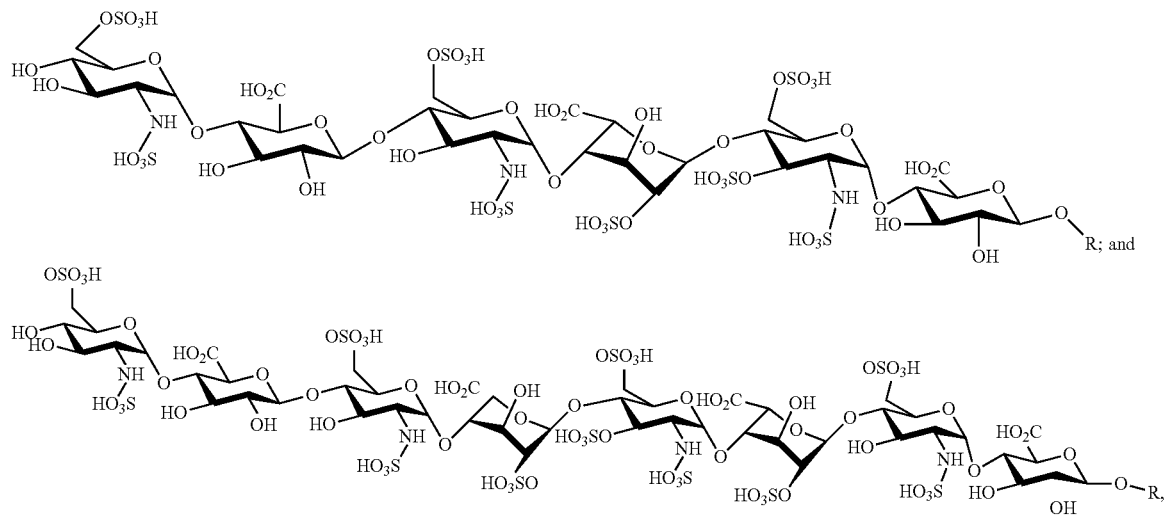

wherein R is selected from the group consisting of —H, alkyl, substituted alkyl, aryl, and substituted aryl.

6. The synthetic heparin analogue of claim 5, wherein the synthetic heparin analogue consists of the following structure:

15. A method of synthesizing a synthetic heparin analogue of claim 1, comprising:
providing a saccharide substrate;
elongating the saccharide substrate to a saccharide of a desired or predetermined length; and

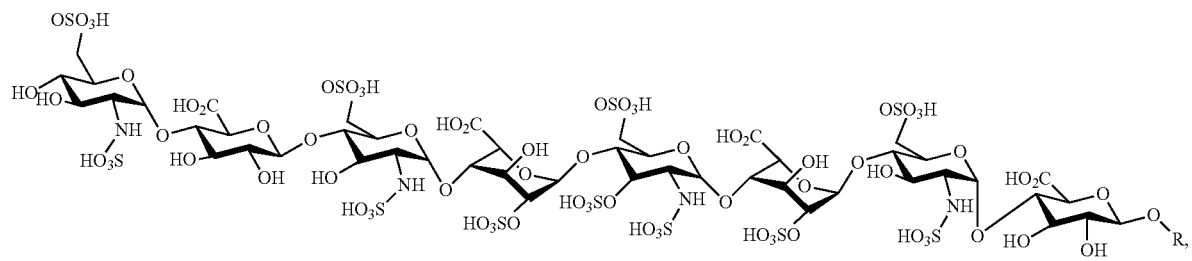

wherein R is selected from the group consisting of —H, alkyl, substituted alkyl, aryl, and substituted aryl.

7. The synthetic heparin analogue of claim 1, wherein the synthetic heparin analogue has a clearance rate about 50% to about 100% faster than that of fondaparinux.

performing at least one sulfation reaction using a 3-OST-3 isoform of a 3-O-sulfotransferase (3-OST) enzyme, whereby a synthetic heparin analogue is synthesized.

16. The method of claim 15, wherein the saccharide substrate comprises at least one IdoA2S-GlcNS3S disaccharide unit.

17. The method of claim 15, wherein the saccharide substrate comprises a IdoA2S-GlcNS3 S±6S disaccharide unit, wherein the method further comprises a 6-O-sulfation step using a 6-O-sulfotransferase (6-OST), wherein a 3-O-sulfation by 3-OST-3 occurs prior to the 6-O-sulfation step.

18. The method of claim 15, wherein the elongation step comprises employing a glycosyl transferase.

19. The method of claim 18, wherein the glycosyl transferase is selected from the group consisting of N-acetyl glucosaminyl transferase of *E. coli* K5 (KfiA) and/or heparosan synthase-2 (pmHS2) from *Pasteurella multocida*.

20. The method of claim 16, wherein the elongation step comprises employing one or more monosaccharides selected from the group consisting of: glucuronic acid (GlcUA), N-acetylated glucosamine (GlcNAc), and N-trifluoroacetyl glucosamine (GlcNTFA).

21. The method of claim 15, wherein the method of synthesizing the synthetic heparin analogue has a yield of greater than about 20% to about 50%.

22. A synthetic heparin analogue produced by the method of claim 15, wherein the synthetic heparin analogue has anticoagulant activity and comprises disaccharide units of a glucuronic acid (GlcA) residue linked to a glucosamine (GlcN) residue modified by sulfation and an iduronic acid (IdoA) residue linked to a GlcN residue modified by sulfation, comprising:
  a 3-O-sulfated oligosaccharide comprising six to eight saccharide units;
  at least one disaccharide unit sulfated by a 3-OST-3 enzyme;
  at least one IdoA2S-GlcNS3 S or at least one IdoA2S-GlcNS3 S6S disaccharide unit, and is devoid of a GlcA-GlcNS3S6S disaccharide unit; and
at least one disaccharide unit comprising a GlcNS6S residue.

23. A synthetic heparin analogue produced by the method of claim 15, wherein the synthetic heparin analogue has a binding affinity to antithrombin ranging from about 5 Nm to about 30 Nm and comprises disaccharide units of a glucuronic acid (GlcA) residue linked to a glucosamine (GlcN) residue modified by sulfaction and an iduronic acid (IdoA) residue linked to a GlcN residue modified by sulfation, comprising:
  a 3-O-sulfated oligosaccharide comprising six to eight saccharide units;
  at least one disaccharide unit sulfated by a 3-OST-3 enzyme;
  at least one IdoA2S-GlcNS3 S or at least one IdoA2S-GlcNS3 S6S disaccharide unit, and is devoid of a GlcA-GlcNS3S6S disaccharide unit; and
at least one disaccharide unit comprising a GlcNS6S residue.

24. A synthetic heparin analogue produced by the method of claim 15, wherein the synthetic heparin analogue has anti-Xa activity ranging from about 10 ngml$^{-1}$ to about 40 ngml$^{-1}$ IC$_{50}$ and comprises disaccharide units of a glucuronic acid (GlcA) residue linked to a glucosamine (GlcN) residue modified by sulfation and an iduronic acid (IdoA) residue linked to a GlcN) residue modified by sulfation, comprising:
  a 3-O-sulfated oligosaccharide comprising six to eight saccharide units;
  at least one disaccharide unit sulfated by a 3-OST-3 enzyme;
  at least one IdoA2S-GlcNS3 S or at least one IdoA2S-GlcNS3 S6S disaccharide unit, and is devoid of a GlcA-GlcNS3S6S disaccharide unit; and
at least one disaccharide unit comprising a GlcNS6S residue.

25. A synthetic heparin analogue produced by the method of claim 15, comprising disaccharide repeating units of a glucuronic acid (Gch) and iduronic acid (IdoA) residue linked to a glucosamine (GlcN) residue modified by sulfation; comprising:
  a 3-O-sulfated oligosaccharide comprising six to eight saccharide units;
  at least one disaccharide unit sulfated by a 3-OST-3 enzyme;
  at least one IdoA2S-GlcNS3S or at least one IdoA2S-GlcNS3 S6S disaccharide unit; and is devoid of a Gch-GlcNS3S6S disaccharide unit; and
at least one GlcNS6S disaccharide unit, and wherein the synthetic heparin analogue comprises a structure selected from the group consisting of:

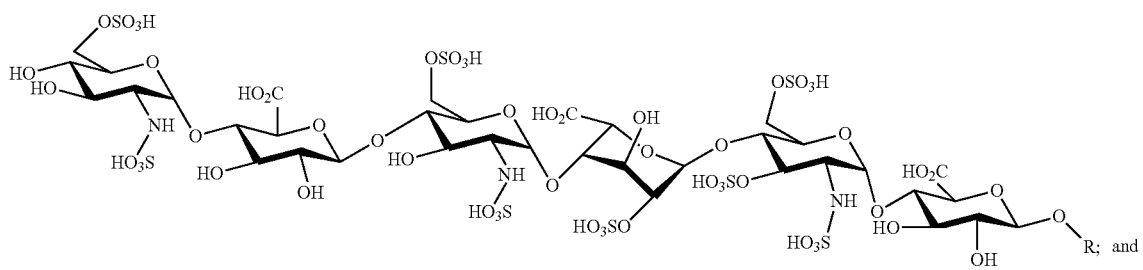

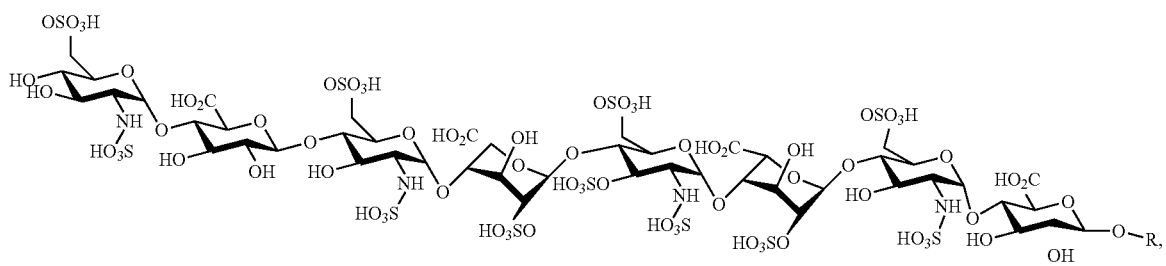

wherein R is selected from the group consisting of —H, alkyl, substituted alkyl, aryl, and substituted aryl.

26. A synthetic heparin analogue produced by the method of claim 15, wherein the synthetic heparin analogue consists of the following structure:

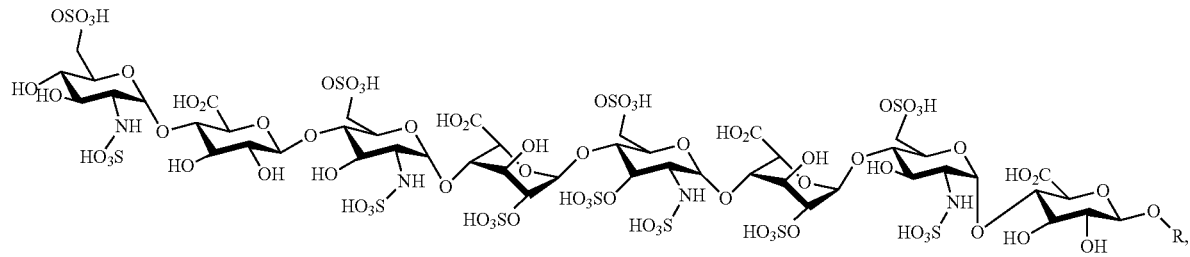

wherein R is selected from the group consisting of —H, alkyl, substituted alkyl, aryl, and substituted aryl.

27. A synthetic heparin analogue produced by the method of claim 15, comprising disaccharide units of a glucuronic acid (GlcA) residue linked to a glucosamine (GlcN) residue modified by sulfation and an iduronic acid (IdoA) residue linked to a GlcN residue modified by sulfation, comprising:
 a 3-O-sulfated oligosaccharide comprising six to eight saccharide units;
 at least one disaccharide unit sulfated by a 3-OST-3 enzyme;
 at least one IdoA2S-GlcNS3 S or at least one IdoA2S-GlcNS3 S6S disaccharide unit, and is devoid of a GlcA-GlcNS3S6S disaccharide unit; and
at least one disaccharide unit comprising a GlcNS6S residue.

28. A synthetic heparin analogue produced by the method of claim 15, wherein the synthetic heparin analogue has a clearance rate about 50% to about 100% faster than that of fondaparinux and comprising disaccharide units of a glucuronic acid (GlcA) residue linked to a glucosamine (GlcN) residue modified by sulfaction and an iduronic acid (IdoA) residue linked to a GlcN residue modified by sulfation, comprising:
 a 3-O-sulfated oligosaccharide comprising six to eight saccharide units;
 at least one disaccharide unit sulfated by a 3-OST-3 enzyme;
 at least one IdoA2S-GlcNS3 S or at least one IdoA2S-GlcNS3 S6S disaccharide unit, and is devoid of a GlcA-GlcNS3S6S disaccharide unit; and
at least one disaccharide unit comprising a GlcNS6S residue.

29. A synthetic heparin analogue produced by the method of claim 15, wherein the synthetic heparin analogue does not cause heparin-induced thrombocytopenia (HIT) and comprising disaccharide units of a glucuronic acid (GlcA) residue linked to a glucosamine (GlcN) residue modified by sulfation and an iduronic acid (IdoA) residue linked to a GlcN residue modified by sulfation, comprising:
 a 3-O-sulfated oligosaccharide comprising six to eight saccharide units;
 at least one disaccharide unit sulfated by a 3-OST-3 enzyme;
 at least one IdoA2S-GlcNS3 S or at least one IdoA2S-GlcNS3 S6S disaccharide unit, and is devoid of a GlcA-GlcNS3S6S disaccharide unit; and
at least one disaccharide unit comprising a GlcNS6S residue.

30. A synthetic heparin analogue produced by the method of claim 15, wherein the anticoagulant activity of the synthetic heparin analogue is reversible by andexanet alfa a rate of 50% or more in the presence of 20 ug/ml or less of andexanet alfa and comprising disaccharide repeating units of a glucuronic acid (GlcA) residue linked to a glucosamine (GlcN) residue modified by sulfation and an iduronic acid (IdoA) residue linked to a GlcN residue modified by sulfation, comprising:
 a 3-O-sulfated oligosaccharide comprising six to eight saccharide units;
 at least one disaccharide unit sulfated by a 3-OST-3 enzyme;
 at least one IdoA2S-GlcNS3 S or at least one IdoA2S-GlcNS3 S6S disaccharide unit, and is devoid of a GlcA-GlcNS3S6S disaccharide unit; and
at least one disaccharide unit comprising a GlcNS6S residue.

31. A method of treating a subject in need of anticoagulant therapy, the method comprising:
 providing a subject in need of anticoagulant therapy;
 administering to the subject a synthetic heparin analogue which comprises disaccharide units of a glucuronic acid (GlcA) residue linked to a glucosamine (GlcN) residue modified by sulfaction and an iduronic acid (IdoA) residue to a GlcN residue modified by sulfation and has anticagulant activity comprising:
 a 3-O-sulfated oligosaccharide comprising six to eight saccharide units;
 at least one disaccharide unit sulfated by a 3-OST-3 enzyme;
 at least one IdoA2S-GlcNS3 S or at least one IdoA2S-GlcNS3 S6S disaccharide unit, and is devoid of a GlcA-GlcNS3S6S disaccharide unit; and
at least one disaccharide unit comprising a GlcNS6S residue.

32. The method of claim 31, further comprising monitoring the subject for heparin-induced thrombocytopenia, and administering to the subject an antidote to reverse the anticoagulant activity of the synthetic heparin analogue if the subject suffers from heparin-induced thrombocytopenia.

33. The method of claim 31, wherein the antidote to reverse the anticoagulant activity of the synthetic heparin analogue is andexanet alfa.

34. The method of claim 31, wherein the subject is a human subject.

35. The method of claim 31, wherein the synthetic heparin analogue has a clearance rate about 50% to about 100% faster than that of fondaparinux.

36. The method of claim 31, wherein the synthetic heparin analogue comprises an anticoagulant activity of less than about 10% at 4 hours post-administration.

37. The method of claim 31, wherein the subject has an elevated risk of bleeding.

38. A method of treating a subject in need of anticoagulant therapy, the method comprising:
providing a subject in need of anticoagulant therapy;
administering to the subject a synthetic heparin analgue, wherein the synthetic heparin analogue comprises a structure selected from the group consisting of:

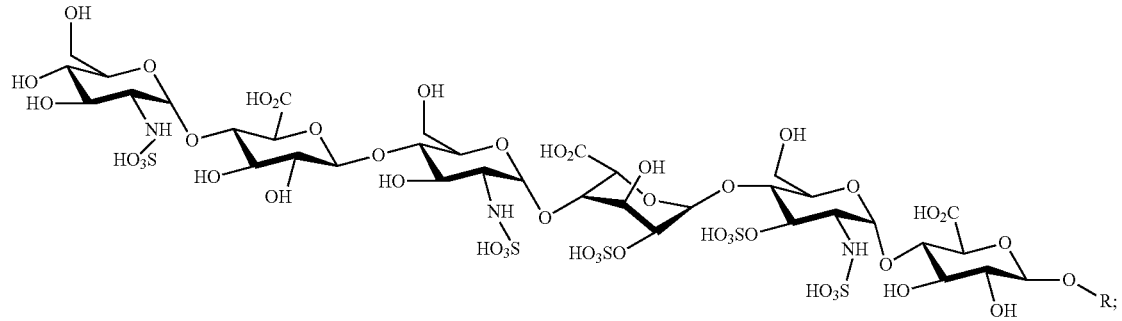

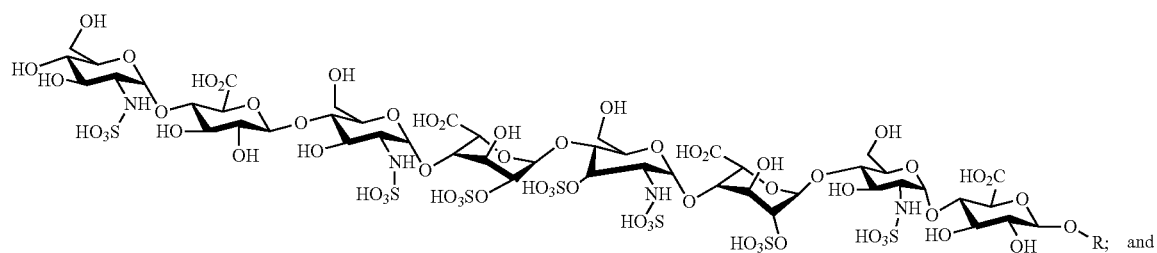

wherein R is selected from the group consisting of —H, alkyl, substituted alkyl, aryl, and substituted aryl.

39. The method of claim 38, wherein the synthetic heparin analogue consists of the following structure:

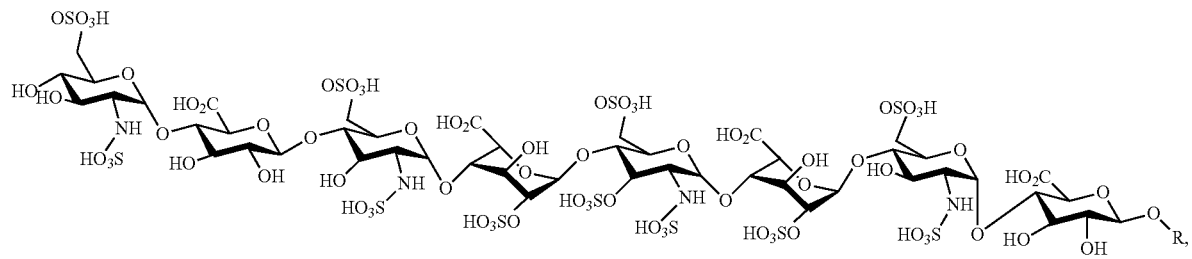

wherein R is selected from the group consisting of —H, alkyl, substituted alkyl, aryl, and substituted aryl.

40. A method of treating a subject in need of anticoagulant therapy, the method comprising:
providing a subject in need of anticoagulant therapy;
administering to the subject a synthetic heparin analogue which comprises disaccharide units of a glucuronic acid (GlcA) residue linked to a glucosamine (GlcN) residue modified by sulfation and an iduronic acid (IdoA) residue linked to a GlcN residue modified by sulfation and has anticoagulant activity, comprising:
a 3-O-sulfated oligosaccharide comprising six to eight saccharide units;
at least one disaccharide unit sulfated by a 3-OST-3 enzyme;
at least one IdoA2S-GlcNS3 S or at least one IdoA2S-GlcNS3 S6S disaccharide unit, and is devoid of a GlcA-GlcNS3S6S disaccharide unit; and
at least one disaccharide unit comprising a GlcNS6S residue.

41. The method of claim 25, wherein the alkyl is —CH$_3$ or —CH$_2$CH$_3$ or the substituted aryl is a p-nitrophenyl group.

42. The synthetic heparin analogue of claim 26, wherein the alkyl is —CH$_3$ or —CH$_2$CH$_3$ or the substituted aryl is a p-nitrophenyl group.

43. The synthetic heparin analogue of claim 38, wherein the alkyl is —CH$_3$ or —CH$_2$CH$_3$ or the substituted aryl is a p-nitrophenyl group.

44. The synthetic heparin analogue of claim 39, wherein the alkyl is —CH$_3$ or —CH$_2$CH$_3$ or the substituted aryl is a p-nitrophenyl group.

* * * * *